(12) United States Patent
Lahm et al.

(10) Patent No.: US 8,623,875 B2
(45) Date of Patent: *Jan. 7, 2014

(54) ISOXAZOLINE INSECTICIDES

(75) Inventors: George Philip Lahm, Wilmington, DE (US); Ty Wagerle, Bear, DE (US); Ming Xu, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 517 days.

This patent is subject to a terminal disclaimer.

(21) Appl. No.: 12/602,821

(22) PCT Filed: Jun. 10, 2008

(86) PCT No.: PCT/US2008/066381
§ 371 (c)(1),
(2), (4) Date: Dec. 3, 2009

(87) PCT Pub. No.: WO2008/154528
PCT Pub. Date: Dec. 18, 2009

(65) Prior Publication Data
US 2010/0179195 A1  Jul. 15, 2010

Related U.S. Application Data

(60) Provisional application No. 60/934,496, filed on Jun. 13, 2007.

(51) Int. Cl.
*A61K 31/496* (2006.01)
*A61K 31/454* (2006.01)
*A61K 31/4439* (2006.01)
*A61K 31/422* (2006.01)
*A61K 31/42* (2006.01)
*C07D 413/12* (2006.01)
*C07D 261/04* (2006.01)

(52) U.S. Cl.
USPC ...... 514/254.04; 514/319; 514/340; 514/378; 544/367; 546/205; 546/272.1; 548/240

(58) Field of Classification Search
None
See application file for complete search history.

(56) References Cited

U.S. PATENT DOCUMENTS

| | | | |
|---|---|---|---|
| 3,879,532 A | 4/1975 | Hass et al. | |
| 4,129,568 A | 12/1978 | Howe | |
| 6,645,984 B2 | 11/2003 | Braun et al. | |
| 7,662,972 B2 | 2/2010 | Mita et al. | |
| 7,897,630 B2 | 3/2011 | Lahm et al. | |
| 7,947,715 B2 | 5/2011 | Mita et al. | |
| 7,951,828 B1 | 5/2011 | Mita et al. | |
| 7,964,204 B2 | 6/2011 | Lahm et al. | |
| 8,022,089 B2 | 9/2011 | Mita et al. | |
| 8,138,213 B2 | 3/2012 | Mita et al. | |
| 8,217,180 B2 | 7/2012 | Annis et al. | |
| 8,231,888 B2 | 7/2012 | Lahm et al. | |
| 8,410,153 B2 | 4/2013 | Lahm et al. | |
| 2005/0250822 A1 | 11/2005 | Mita et al. | |
| 2007/0066617 A1 | 3/2007 | Mita et al. | |
| 2009/0023923 A1 | 1/2009 | Mizukoshi et al. | |
| 2009/0133319 A1 | 5/2009 | Lahm et al. | |
| 2009/0143410 A1 | 6/2009 | Patel | |
| 2010/0137612 A1 | 6/2010 | Yaosaka et al. | |
| 2010/0173948 A1 | 7/2010 | Lahm et al. | |
| 2010/0179195 A1 | 7/2010 | Lahm et al. | |
| 2010/0249424 A1 | 9/2010 | Annis et al. | |
| 2010/0254959 A1 | 10/2010 | Lahm et al. | |
| 2010/0254960 A1 | 10/2010 | Long et al. | |
| 2011/0059988 A1 | 3/2011 | Heckeoth et al. | |

FOREIGN PATENT DOCUMENTS

| | | |
|---|---|---|
| CA | 2252543 | 11/1997 |
| CA | 2558848 | 9/2005 |
| CN | 101346336 | 1/2009 |
| EA | 000924 | 6/2000 |
| EP | 1538138 | 6/2005 |
| EP | 1731512 | 12/2006 |
| EP | 1975149 | 10/2008 |
| EP | 2172462 | 4/2010 |

(Continued)

OTHER PUBLICATIONS

Notice of allowance dated Jan. 11, 2011 received in copending U.S. Appl. No. 12/086,935.

(Continued)

*Primary Examiner* — Alicia L Otton
(74) *Attorney, Agent, or Firm* — Pepper Hamilton LLP

(57) ABSTRACT

Disclosed are compounds of Formula 1, including all geometric and stereoisomers, N-oxides, and salts thereof,

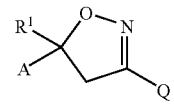

wherein
A is a 6-membered aromatic ring containing carbon atoms and 0-3 nitrogen atoms as ring members, said ring optionally substituted with 1-5 substituents independently selected from $R^2$;
$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{21}$;
$R^{21}$ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$; and
Q is as defined in the disclosure.
Also disclosed are compositions containing the compounds of Formula 1 and methods for controlling an invertebrate pest comprising contacting the invertebrate pest or its environment with a biologically effective amount of a compound or a composition of the invention.

25 Claims, No Drawings

(56) References Cited

FOREIGN PATENT DOCUMENTS

| | | |
|---|---|---|
| EP | 1973888 | 1/2011 |
| GB | 2351081 | 12/2000 |
| JP | 199859944 | 3/1998 |
| JP | 1999503114 | 3/1999 |
| JP | 2004529130 | 9/2004 |
| JP | 2005272452 | 10/2005 |
| JP | 2007016017 | 1/2007 |
| JP | 2007106756 | 4/2007 |
| KZ | 13246 | 7/2003 |
| KZ | 16356 | 10/2005 |
| RU | 99101948 | 10/2001 |
| RU | 2433123 | 11/2011 |
| TW | 200738696 | 10/2007 |
| WO | 9854122 | 12/1998 |
| WO | 2004099197 | 11/2004 |
| WO | 2005085216 | 9/2005 |
| WO | 2005094329 | 10/2005 |
| WO | 2006135640 | 12/2006 |
| WO | 2007026965 | 3/2007 |
| WO | 2007070606 | 6/2007 |
| WO | WO2007070606 | 6/2007 |
| WO | 2007074789 | 7/2007 |
| WO | 2007075459 | 7/2007 |
| WO | 2007079162 | 7/2007 |
| WO | WO 2007/079162 * 7/2007 ........... C07D 261/04 |
| WO | 2007105814 | 9/2007 |
| WO | 2007123855 | 11/2007 |
| WO | 2007125984 | 11/2007 |
| WO | 2008019760 | 2/2008 |
| WO | 2008108448 | 9/2008 |
| WO | 2008122375 | 10/2008 |
| WO | 2008154528 | 12/2008 |
| WO | 2009001942 | 12/2008 |
| WO | 2009002809 | 12/2008 |
| WO | 2009003075 | 12/2008 |
| WO | 2009025983 | 2/2009 |
| WO | 2009035004 | 3/2009 |
| WO | 2009045999 | 4/2009 |

OTHER PUBLICATIONS

U.S. Appl. No. 12/083,943, filed Apr. 21, 2008, now abandoned.
Office Action dated Sep. 21, 2011 received in copending U.S. Appl. No. 13/156,653.
Non-final Office Action dated Nov. 28, 2011 received in copending U.S. Appl. No. 12/663,751.
Lahm et al (2007): STN International HCAPLUS database, Columbus (OH), accession No. 2007:755410.
Motoki et al., "Copper(I) alkoxide-catalyzed alkynylation of trifluoromethyl ketones," Organic Letters (2007) 9(16):2997-3000.
Mita et al. (2007): STN International HCAPLUS database, (Columbus, Ohio), Accession No. 2009:740002.
Office Action dated Jan. 23, 2012 received in copending U.S. Appl. No. 12/677,927.
Notice of Allowance dated Feb. 6, 2012 received in copending U.S. Appl. No. 12/663,848.
Notice of Allowance and Fee(s) due Mar. 18, 2012 received in copending U.S. Appl. No. 12/679,382.
Notice of Allowance and Fee(s) due Mar. 21, 2012 received in copending U.S. Appl. No. 13/156,653.
Konno et al., "Palladium-Catalyzed Regio- and Stereoselective Formate Reduction of Fluorine-Containing Allylic Mesylates. A New Entry for the Construction of a Tertiary Carbon Attached with a Fluoroalkyl Group," Journal of Organic Chemistry (2006) 71(9):3545-3550.
Carey et al., "Advanced Organic Chemistry," 2ed., Part B: Reactions and Synthesis, (1983) Pelenum Press, New York.
Sosnovskii et al., "Ketone-ketone condensation with participation of polyhaloalkyl phenyl ketones," Journal of Organic Chemistry of the USSR, (1992) 28:420-426.
Kamble et al., "An efficient synthesis of pharmacologically active derivatives 1,3,4-Oxadiazoles," Journal of Heterocyclic Chemistry (2006) 43(345):345-352.
Database Chemical Abstracts Service (1988) XP002516318, Database accession No. 111:115084.
Ragaila et al., "Newer heterocycles and carbamates from naphthyl," Egyptian Journal of Pharmaceutical Sciences (1988) 29(1-4):71-87.
Database Chemical Abstracts Service (1996) XP002516333, Database Accession No. 126:31303.
Kuznetsova et al., "Synthesis of fluorine-containing functionalized isoxazolines," Russian Chemical Bulletin (1996) 45(5):1245-1246.
Notice of Allowance dated Jan. 1, 2011 received in copending U.S. Appl. No. 12/086,935.
Notice of Allowance dated Sep. 28, 2010 received in copending U.S. Appl. No. 12/086,935.
Notice of Allowance dated Oct. 21, 2010 received in copending U.S. Appl. No. 12/083,944.
Non-final Office Action dated May 19, 2010 received in copending U.S. Appl. No. 12/083,944.
Non-final Office Action dated Dec. 16, 2009 received in copending U.S. Appl. No. 12/083,944.
Non-final Office Action dated Aug. 3, 2009 received in copending U.S. Appl. No. 12/083,944.
Dighade et al,. "Effect of solvents in synthesis of new 4-(2-hydroxy-5-methylphenyl)-6-aryl-2-imino-6H-2,3-dihydro-1,3-thiazines," Asian Journal of Chemistry (2001) 13(4):1560-1564.
International Search Report dated Feb. 24, 2011 received in copending International Application No. PCT/US2009/039832.
Office Action Aug. 14, 2012 received in copending U.S. Appl. No. 12/933,493.
Notice of Allowance dated Sep. 24, 2012 received in copending U.S. Appl. No. 12/677,927.
Office Action dated Nov. 23, 2012 received in counterpart U.S. Appl. No. 13/561,546.
Notice of Allowance dated Nov. 14, 2012 received in counterpart U.S. Appl. No. 12/663,751.
Office Action dated Jul. 2, 2012 received in copending U.S. Appl. No. 12/677,927.
Office Action dated Jun. 8, 2012 received in copending U.S. Appl. No. 12/663,848.
Mita et al. (2007): STN International HCAPLUS database, Columbus (OH), accession No. 2007:330406.
Office Action dated Jun. 8, 2012 received in copending U.S. Appl. No. 12/663,751.
[Kuznetsova et al., "Synthesis of fluorine-containing functionalized isoxazolines," Proceedings of the Academy of Sciences (1996) 5:1306-1307]. English Translation of Russian Office Action received Jul. 3, 2012 attached.
Advisory Action dated Sep. 6, 2012 received in copending U.S. Appl. No. 12/677,927.
Notice of Allowance dated Apr. 15, 2013 received in copending U.S. Appl. No. 13/544,113.
Notice of Allowance dated May 14, 2013 received in copending U.S. Appl. No. 12/933,493.
Notice of Allowance dated Jun. 7, 2013 received in copending U.S. Appl. No. 13/561,546.
Final Office Action dated Jan. 28, 2013 received in copending U.S. Appl. No. 12/663,848.

* cited by examiner

ISOXAZOLINE INSECTICIDES

FIELD OF THE INVENTION

This invention relates to certain isoxazolines, their N-oxides, salts and compositions suitable for agronomic, nonagronomic and animal health uses, methods of their use for controlling invertebrate pests such as arthropods in both agronomic and nonagronomic environments, and for treatment of parasite infections in animals or infestations in the general environment.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

The control of animal parasites in animal health is essential, especially in the areas of food production and companion animals. Existing methods of treatment and parasite control are being compromised due to growing resistance to many current commercial parasiticides. The discovery of more effective ways to control animal parasites is therefore imperative.

PCT Patent Publication WO 05/085216 discloses isoxazoline derivatives of Formula i as insecticides

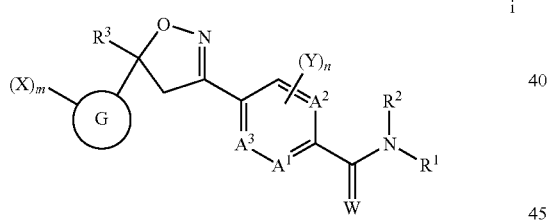

wherein, inter alia, each of $A^1$, $A^2$ and $A^3$ are independently C or N; G is a benzene ring; W is O or S; and X is halogen or $C_1$-$C_6$ haloalkyl.

The isoxazolines of the present invention are not disclosed in this publication.

SUMMARY OF THE INVENTION

This invention is directed to compounds of Formula 1 including all geometric and stereoisomers, N-oxides, and salts thereof, and compositions containing them and their use for controlling invertebrate pests:

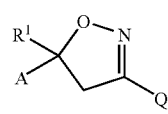

wherein

A is a 6-membered aromatic ring containing carbon atoms and 0-3 nitrogen atoms as ring members, said ring optionally substituted with 1-5 substituents independently selected from $R^2$;

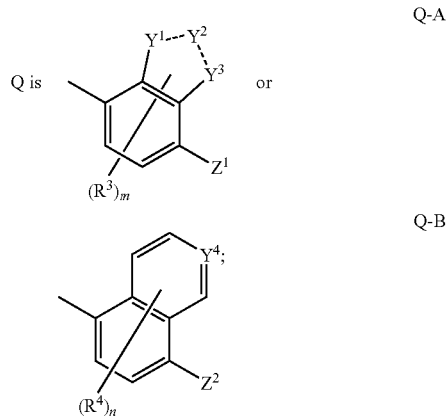

$Y^1$—$Y^2$—$Y^3$ is —CH=CH—S—, —CH=CH—O—, —CH=CH—NH—, —CH=N—NH—, —S—CH=CH—, —O—CH=CH—, —NH—CH=CH— or —NH—N=CH—;

$Y^4$ is $CR^4$ or N;

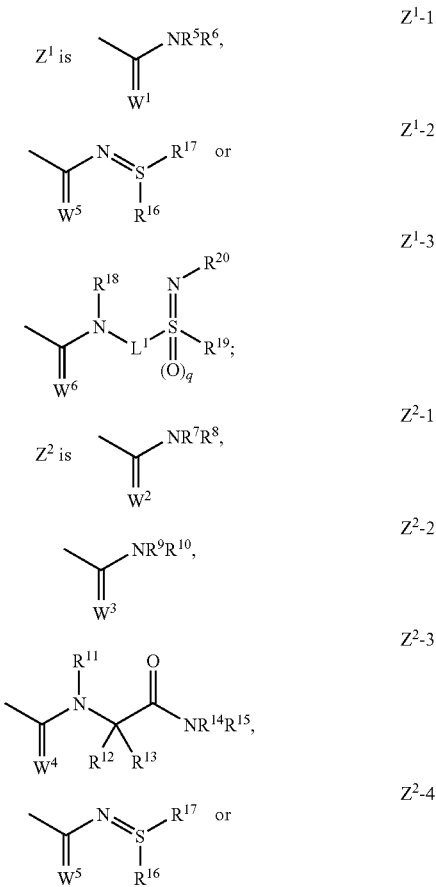

-continued

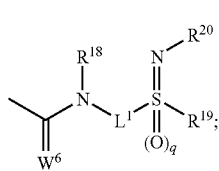

Z²-5 each W¹, W², W³, W⁴, W⁵ and W⁶ is independently O or S;
L¹ is $C_2$-$C_6$ alkylene optionally substituted with one or more substituents independently selected from $R^{22}$;
R¹ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{21}$;
each R² is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;
each R³ and R⁴ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;
R⁵ is H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{22}$; or $C(=O)R^{23}$, $CO_2R^{24}$, $C(=O)NR^{25}R^{26}$, $OR^{27}$, $SR^{28}$, $S(=O)R^{29}$, $SO_2R^{30}$, $NR^{31}R^{32}$ or $Q^1$;
R⁶ is H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{33}$; or $C(=O)R^{23}$, $CO_2R^{24}$, $C(=O)NR^{25}R^{26}$ or $Q^1$; or
R⁵ and R⁶ are taken together with the nitrogen atom to which they are attached to form a ring containing as ring members in addition to the attaching nitrogen atom from 2 to 6 carbon atoms and optionally one additional ring member selected from the group consisting of O, N and $S(=O)_u$, said ring optionally substituted with 1 to 4 substituents independently selected from the group consisting of halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C(=O)R^{23}$, $CO_2R^{24}$, $C(=O)NR^{25}R^{26}$; CN and $NO_2$;
R⁷ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;
R⁸ is $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{18}$ alkylcycloalkyl or $C_4$-$C_{18}$ cycloalkylalkyl, each substituted with one or more substituents independently selected from $R^{34}$ and optionally substituted with one or more substituents independently selected from $R^{35}$; or
R⁷ and R⁸ are taken together with the nitrogen atom to which they are attached to form a ring containing as ring members in addition to the attaching nitrogen atom from 2 to 6 carbon atoms and optionally one additional ring member selected from the group consisting of O, N and $S(=O)_u$, said ring optionally substituted with 1 to 4 substituents independently selected from the group consisting of halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C(=O)R^{23}$, $CO_2R^{24}$ and $C(=O)NR^{25}R^{26}$;
each R⁹ and R¹⁸ is independently H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{35}$;
R¹⁰ is $C_1$-$C_{12}$ alkyl substituted with one or more $R^{35}$; or CN, SCN, $S(=O)_uR^{37}$, $SO_2NR^{37}R^{38}$, $N=CR^{38}R^{39}$, $N=CR^{38}OR^{39}$, $NR^{37}C(=O)R^{38}$, $NR^{37}C(=O)OR^{38}$, $SiR^{41}R^{42}R^{43}$, $CO_2R^{36}$; $C(=O)R^{36}$, $C(=O)NR^{37}R^{38}$, $C(=S)SR^{39}$, $C(=S)OR^{39}$, $C(=S)R^{38}$, $C(=S)NR^{37}R^{38}$, $P(=O)(OR^{39})_2$ or $P(=S)(OR^{39})_2$; provided that when R⁹ is H or an unsubstituted group of $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, then R¹⁰ is CN, SCN, $S(=O)_uR^{37}$, $SO_2NR^{37}R^{38}$, $N=CR^{38}R^{39}$, $N=CR^{38}OR^{39}$, $SiR^{41}R^{42}R^{43}$, $CO_2R^{36}$, $C(=O)R^{36}$, $C(=O)NR^{37}R^{38}$, $C(=S)SR^{39}$, $C(=S)OR^{39}$, $C(=S)R^{38}$, $C(=S)NR^{37}R^{38}$, $P(=O)(OR^{39})_2$ or $P(=S)(OR^{39})_2$;
R¹¹ is H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{35}$; or CN, $C(=O)R^{23}$, $CO_2R^{24}$, $C(=O)NR^{25}R^{26}$, $OR^{27}$, $SR^{28}$, $S(=O)R^{29}$, $SO_2R^{30}$, $NR^{31}R^{32}$, $C(=S)SR^{37}$, $C(=S)OR^{37}$, $C(=S)R^{37}$, $C(=S)NR^{37}R^{38}$, $SO_2NR^{37}R^{38}$, $NR^{37}C(=O)R^{38}$, $NR^{37}SO_2R^{29}$ or $Q^1$;
R¹² is H; or $C_1$-$C_{12}$ alkyl, $C_3$-$C_7$ cycloalkyl, $C_4$-$C_{12}$ alkylcycloalkyl, $C_4$-$C_{12}$ cycloalkylalkyl, each optionally substituted with one or more substituents independently selected from $R^{35}$; or $Q^1$;
R¹³ is H; or $C_1$-$C_{12}$ alkyl, $C_3$-$C_7$ cycloalkyl, $C_4$-$C_{12}$ alkylcycloalkyl or $C_4$-$C_{12}$ cycloalkylalkyl, each optionally substituted with one or more substituents independently selected from $R^{35}$; or CN, $C(=O)R^{36}$, $C(=O)OR^{37}$, $C(=S)SR^{37}$, $C(=S)OR^{37}$, $C(=S)R^{37}$, $C(=S)NR^{37}R^{38}$ or $Q^1$; or
R¹² and R¹³ are taken together with the carbon atom to which they are attached to form a carbocyclic ring containing as ring members from 3 to 6 carbon atoms, said ring optionally substituted with one or more substituents independently selected from $R^{35}$;
R¹⁴ and R¹⁵ are independently H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{35}$; or CN, $C(=O)R^{23}$, $CO_2R^{24}$, $C(=O)NR^{25}R^{26}$, $OR^{27}$, $SR^{28}$, $S(=O)R^{29}$, $SO_2R^{30}$, $NR^{31}R^{32}$, $C(=S)SR^{37}$, $C(=S)OR^{37}$, $C(=S)R^{37}$, $C(=S)NR^{37}R^{38}$, $SO_2NR^{37}R^{38}$, $NR^{37}C(=O)R^{38}$, $NR^{37}SO_2R^{29}$ or $Q^1$; or
R¹⁴ and R¹⁵ are taken together with the nitrogen atom to which they are attached to form a ring containing as ring members in addition to the attaching nitrogen atom from 2 to 6 carbon atoms and optionally one additional ring member selected from the group consisting of O, N and $S(=O)_u$, said ring optionally substituted with 1 to 4 substituents independently selected from the group consisting of halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C(=O)R^{23}$, $CO_2R^{24}$, $C(=O)NR^{25}R^{26}$, CN and $NO_2$; provided that R¹⁴ and $R^{15}$ are other than $C_1$-$C_6$ alkyl or $C_1$-$C_6$ haloalkyl when $R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

each $R^{16}$ and $R^{17}$ is independently $C_1$-$C_6$ alkyl optionally substituted with one or more substituents independently selected from $R^{35}$; or $R^{16}$ and $R^{17}$ are taken together with the sulfur atom to which they are attached to form a ring containing as ring members in addition to the attaching sulfur atom from 3 to 6 carbon atoms, said ring optionally substituted with one or more substituents independently selected from $R^{35}$;

$R^{19}$ is $C_1$-$C_6$ alkyl optionally substituted with one or more substituents independently selected from $R^{35}$;

$R^{20}$ is H; or $C_1$-$C_6$ alkyl optionally substituted with one or more substituents independently selected from $R^{35}$; or CN, C(=O)$R^{24}$, $CO_2R^{24}$ or $NO_2$;

$R^{21}$ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

each $R^{22}$, $R^{33}$ and $R^{35}$ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN, $NO_2$, SCN, C(=O)$R^{37}$, $CO_2R^{37}$, C(=S)S$R^{37}$, C(=S)O$R^{37}$, C(=S)$R^{37}$, C(=O)$NR^{37}R^{38}$, C(=S)$NR^{37}R^{38}$, $SO_2NR^{37}R^{38}$, $NR^{37}R^{38}$, $SiR^{41}R^{42}R^{43}$ or $Q^1$;

each $R^{23}$, $R^{25}$, $R^{26}$, $R^{27}$, $R^{28}$, $R^{31}$ and $R^{32}$ is independently H; or $C_1$-$C_{18}$ alkyl, $C_2$-$C_8$ alkenyl, $C_2$-$C_8$ alkynyl, $C_3$-$C_9$ cycloalkyl, $C_4$-$C_{10}$ alkylcycloalkyl or $C_4$-$C_{10}$ cycloalkylalkyl, each optionally substituted with one or more substituents independently selected from $R^{35}$; or $Q^1$;

each $R^{24}$, $R^{29}$ and $R^{30}$ is independently H; or $C_1$-$C_{18}$ alkyl, $C_2$-$C_8$ alkenyl, $C_2$-$C_8$ alkynyl, $C_3$-$C_9$ cycloalkyl, $C_4$-$C_{10}$ alkylcycloalkyl or $C_4$-$C_{10}$ cycloalkylalkyl, each optionally substituted with one or more substituents independently selected from $R^{35}$; or $Q^1$;

$R^{34}$ is O$R^{36}$, OC(=O)$R^{37}$, OC(=O)$NR^{37}R^{38}$, $OCO_2R^{37}$, $OSO_2R^{39}$, SH, S$R^{36}$, S(=O)$R^{36}$, $SO_2R^{36}$, $SO_2NR^{37}R^{38}$, $NR^{36}R^{37}$, N=C$R^{37}R^{40}$; N=C$R^{40}OR^{37}$, $NR^{37}$C(=O)$R^{38}$, SCN, $SiR^{41}R^{42}R^{43}$; $CO_2$H, $CO_2R^{46}$, C(=O)$R^{46}$, C(=S)S$R^{40}$, C(=S)O$R^{40}$, C(=O)S$R^{40}$, C(=S)$R^{37}$, C(=S)$NR^{37}R^{38}$, P(=O)(O$R^{37})_2$ or P(=S)(O$R^{37})_2$;

$R^{36}$ is $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each substituted with one or more substituents independently selected from halogen, CN, $NO_2$, O$R^{44}$, S$R^{44}$, S(=O)$R^{44}$, $SO_2R^{44}$; $CO_2R^{44}$ and C(=O)$NR^{44}R^{45}$;

each $R^{37}$ and $R^{38}$ is independently H; or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each optionally substituted with one of more substituents independently selected from the group consisting of halogen, CN, $NO_2$, O$R^{44}$, S$R^{44}$, S(=O)$R^{44}$; $SO_2R^{44}$, $CO_2R^{44}$, C(=O)$NR^{44}R^{45}$ and $Q^1$;

$R^{39}$ is $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each optionally substituted with one or more substituents independently selected from the group consisting of halogen, CN, $NO_2$, O$R^{44}$, S$R^{44}$, S(=O)$R^{44}$, $SO_2R^{44}$, $CO_2R^{44}$, C(=O)$NR^{44}R^{45}$ and $Q^1$;

$R^{40}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl or a phenyl ring, each optionally substituted with one of more substituents independently selected from the group consisting of halogen, $C_1$-$C_6$ alkoxy, $C_1$-$C_6$ haloalkoxy, CN and $NO_2$;

each $R^{41}$, $R^{42}$ and $R^{43}$ is independently $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or a phenyl ring, each optionally substituted with one of more substituents selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN and $NO_2$;

each $R^{44}$ and $R^{45}$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more substituents selected from $R^{35}$; or $Q^1$;

$R^{46}$ is $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each substituted with one or more substituents selected from CN, $NO_2$, O$R^{44}$, S$R^{44}$, S(=O)$R^{44}$, $SO_2R^{44}$, $CO_2R^{44}$ and C(=O)$NR^{44}R^{45}$;

each $Q^1$ is a 3- to 10-membered ring or 7- to 10-membered bicyclic ring system containing as ring members from 2 to 10 carbon atoms and from 0 to 5 heteroatoms selected from the group consisting of carbon, sulfur and nitrogen atoms, of which up to two of the carbon or sulfur atoms are present as C(=O), S(=O) or $SO_2$, said ring or ring system optionally substituted with one or more substituents independently selected from $R^2$;

m is an integer from 0 to 5;

n is an integer from 0 to 4;

q is 0 or 1; and u is 0, 1 or 2.

This invention also provides a composition comprising a compound of Formula 1, an N-oxide or a salt thereof, and at least one additional component selected from the group consisting of surfactants, solid diluents and liquid diluents. In one embodiment, this invention also provides a composition for controlling an invertebrate pest comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This invention further provides a spray composition for controlling an invertebrate pest comprising a biologically effective amount of a compound of Formula 1, an N-oxide or a salt thereof, or the composition described above, and a propellant. This invention also provides a bait composition for controlling an invertebrate pest comprising a biologically effective amount of a compound of Formula 1, an N-oxide or a salt thereof, or the compositions described in the embodiments above, one or more food materials, optionally an attractant, and optionally a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

This invention provides a method for controlling an invertebrate pest comprising contacting the invertebrate pest or its environment with a biologically effective amount of a compound of Formula 1, an N-oxide or a salt thereof, (e.g., as a composition described herein). This invention also relates to such method wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This invention also provides a method for protecting a seed from an invertebrate pest comprising contacting the seed with a biologically effective amount of a compound of Formula 1, an N-oxide or a salt thereof, (e.g., as a composition described herein). This invention also relates to the treated seed.

This invention further provides a method for protecting an animal from an invertebrate parasitic pest comprising administering to the animal a parasiticidally effective amount of a compound of Formula 1, an N-oxide or a salt thereof, (e.g., as a composition described herein). This invention further provides a method for treating, preventing, inhibiting and/or killing ecto- and/or endoparasites comprising administering to and/or on the animal a parasiticidally effective amount of a compound of Formula 1 (e.g., as a composition described herein). This invention also relates to such method wherein a parasiticidally effective amount of a compound of Formula 1 (e.g., as a composition described herein) is administered to the environment (e.g., a stall or blanket) in which an animal resides.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as roundworms, heartworms, and phytophagous nematodes (Nematoda), flukes (Tematoda), Acanthocephala, and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives). The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

A parasite "infestation" refers to the presence of parasites in numbers that pose a risk to humans or animals. The infestation can be in the environment (e.g., in human or animal housing, bedding, and surrounding property or structures), on agricultural crops or other types of plants, or on the skin or fur of an animal. When the infestation is within an animal (e.g., in the blood or other internal tissues), the term infestation is also intended to be synonymous with the term "infection" as that term is generally understood in the art, unless otherwise stated.

In the present disclosure and claims, the radical "$SO_2$" means sulfonyl, "CN" means cyano, and "$NO_2$" means nitro.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)-$, $CH_3CH_2S(=O)-$, $CH_3CH_2CH_2S(=O)-$, $(CH_3)_2CHS(=O)-$ and the different butylsulfinyl, pentylsulfinyl and hexylsulfinyl isomers. Examples of "alkylsulfonyl" include $CH_3SO_2-$, $CH_3CH_2SO_2-$, $CH_3CH_2CH_2SO_2-$, $(CH_3)_2CHSO_2-$, and the different butylsulfonyl, pentylsulfonyl and hexylsulfonyl isomers.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C-$, $ClCH_2-$, $CF_3CH_2-$ and $CF_3CCl_2-$. The terms "haloalkoxy" and "haloalkylthio" and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(=O)-$, $CCl_3S(=O)-$, $CF_3CH_2S(=O)-$ and $CF_3CF_2S(=O)-$. Examples of "haloalkylsulfonyl" include $CF_3SO_2-$, $CCl_3SO_2-$, $CF_3CH_2SO_2-$ and $CF_3CF_2SO_2-$.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3OC(=O)-$, $CH_3CH_2OC(=O)-$, $CH_3CH_2CH_2OC(=O)-$, $(CH_3)_2CHOC(=O)-$ and the different butoxy- or pentoxycarbonyl isomers.

The total number of carbon atoms in a substituent group is indicated by the "$C_i$-$C_j$" prefix where i and j are numbers from 1 to 18. For example, $C_1$-$C_4$ alkylsulfonyl designates methylsulfonyl through butylsulfonyl.

When a compound is substituted with a substituent bearing a subscript that indicates the number of said substituents can exceed 1, said substituents (when they exceed 1) are independently selected from the group of defined substituents, e.g., $(R^3)_m$ or $(R^4)_n$, m is 0, 1, 2, 3, 4 or 5 and n is 0, 1, 2, 3 or 4. As $(R^3)_m$ or $(R^4)_n$ are optional substituents on bicyclic rings, Q-A and Q-B respectively, each may substitute any available carbon or nitrogen ring member(s) of the bicyclic ring. For example, when Q is Q-A and $Y^1$—$Y^2$—$Y^3$ is —CH=CH—S—, then the $(R^3)_m$ substituents can also be attached to the two available carbon atoms of the —CH=CH—S— moiety (e.g., —$C(R^3)$=CH—S—, —CH=$C(R^3)$—S— or —$C(R^3)$=$C(R^3)$—S—. When a group contains a substituent which can be hydrogen, for example $R^3$ or $R^4$, then when this substituent is taken as hydrogen, it is recognized that this is equivalent to said group being unsubstituted. When a variable group is shown to be optionally attached to a position, for example $(R^3)_m$ wherein m may be 0, then hydrogen may be at the position even if not recited in the variable group definition. When one or more positions on a group are said to be "not substituted" or "unsubstituted", then hydrogen atoms are attached to take up any free valency.

The orientation of the $Y^1$—$Y^2$—$Y^3$ substitutents is as depicted in Q-A. For example, when $Y^1$—$Y^2$—$Y^3$ is —CH=CH—S—, then $Y^1$ is CH, $Y^2$ is CH and $Y^3$ is S.

The attachment point of a substituent to a structure is represented by a wavy line bisecting the bond joining the substituent to the remainder of the structure. For example, a benzyl substituent can be represented as

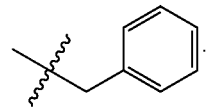 [SMILES: *Cc1ccccc1]

Unless otherwise indicated, a "ring" or "ring system" as a component of Formula 1 (e.g., substituent A or $Q^1$) is carbocyclic or heterocyclic. The term "ring system" denotes two or more fused rings. The term "bicyclic ring system" denotes a ring system consisting of two fused rings, in which either ring can be saturated, partially unsaturated, or fully unsaturated unless otherwise indicated. The term "ring member" refers to an atom or other moiety (e.g., $C(=O)$, $C(=S)$, $S(=O)$ or $SO_2$) forming the backbone of a ring or ring system.

The terms "carbocyclic ring" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which $(4n+2)\pi$ electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" denotes a carbocyclic ring in which no ring in the ring system is aromatic. The term "nonaromatic heterocyclic ring system" denotes a heterocyclic ring system in which no ring in the ring system is aromatic.

As is generally known in the art, the chemical name "pyridyl" is synonymous with "pyridinyl".

The term "optionally substituted" is used herein interchangeably with the phrase "substituted or unsubstituted" or with the term "(un)substituted". Unless otherwise indicated, an optionally substituted group may have a substituent at each substitutable position of the group, and each substitution is independent of the other. An optionally substituted group also may have no substituents. Therefore the phrase "optionally substituted with one or more substituents" means that the number of substituents may vary from zero up to the number of available positions for substitution. Similarly the phrase "optionally substituted with 1-5 substituents" means that the number of substituents may vary from zero up to the number of available position but not exceeding 5.

As already defined, $Q^1$ is a 3- to 10-membered ring or 7- or 10-membered bicyclic ring system containing as ring members from 2 to 10 carbon atoms and from 0 to 5 heteroatoms selected from the group consisting of carbon, sulfur and nitrogen atoms, of which up to two of the carbon or sulfur atoms are present as C(=O), S(=O) or $SO_2$, said ring or ring system optionally substituted with one or more substituents independently selected from $R^2$. Therefore the ring or bicyclic ring system of $Q^1$ may be saturated, partially saturated or fully unsaturated (including aromatic if Hückel's rule is satisfied). Furthermore the ring or bicyclic ring system may contain only carbon atoms as ring members (i.e. carbocyclic) or a combination of carbon atoms and heteroatoms (i.e. heterocyclic). In particular, the ring members of $Q^1$ may include up to 5 heteroatoms selected from C, S and N as ring members. The possible number of heteroatoms is limited by the number of ring members in the ring or ring system. Up to two of the carbon or sulfur atom ring members (including combinations thereof) may be present as C(=O), S(=O) or $SO_2$ (including combinations thereof).

As defined above, A is a 6-membered aromatic ring containing carbon atoms and 0-3 nitrogen atoms as ring members, said ring optionally substituted with 1-5 substituents independently selected from $R^2$. Examples of these rings optionally substituted by 1 to 5 substituents include the rings A-1 through A-14 illustrated in Exhibit 1 wherein $R^v$ is any substituent as defined in the Summary of the Invention for A (i.e. $R^2$) and r is an integer from 0 to 5, limited by the number of available positions on each A group.

Exhibit 1

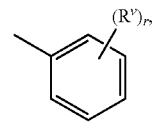
A-1

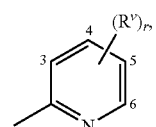
A-2

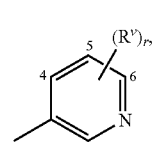
A-3

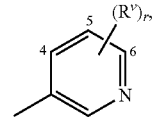
A-4

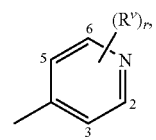
A-5

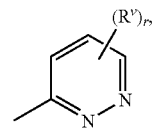
A-6

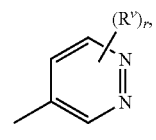
A-7

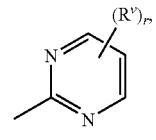
A-8

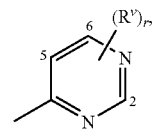
A-9

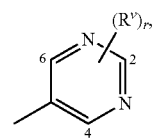
A-10

-continued

A-11
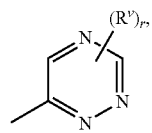

A-12
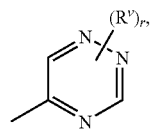

A-13
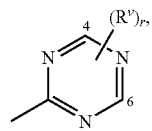

A-14
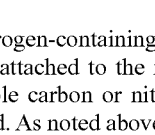

When $Q^1$ is a nitrogen-containing heterocyclic ring or ring system, it may be attached to the remainder of Formula 1 though any available carbon or nitrogen ring atom, unless otherwise described. As noted above, $Q^1$ can be (among others) phenyl optionally substituted with one or more substituents selected from a group of substituents as defined in the Summary of Invention. An example of phenyl optionally substituted with one to five substituents is the ring illustrated as U-1 in Exhibit 1, wherein $R^v$ is $R^2$ as defined in the Summary of the Invention for $Q^1$ and r is an integer from 0 to 5.

As noted above, $Q^1$ can be (among others) a 5- or 6-membered heterocyclic ring, which may be saturated or unsaturated, optionally substituted with one or more substituents selected from a group of substituents as defined in the Summary of Invention. Examples of a 5- or 6-membered aromatice unsaturated heterocyclic ring optionally substituted with one or more substituents include the rings U-2 through U-61 illustrated in Exhibit 2 wherein $R^v$ is any substituent as defined in the Summary of the Invention for $Q^1$ (i.e. $R^2$) and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 2

U-1
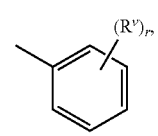

U-2
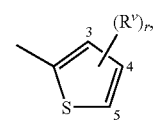

-continued

U-3
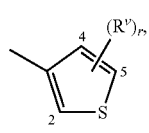

U-4
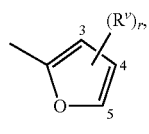

U-5
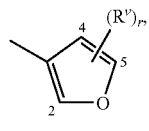

U-6
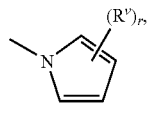

U-7
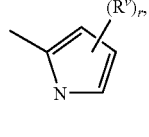

U-8
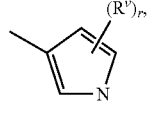

U-9
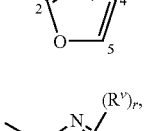

U-10
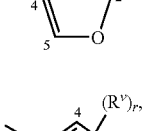

U-11
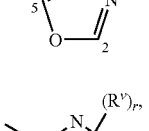

U-12
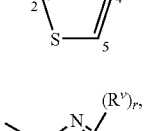

U-13
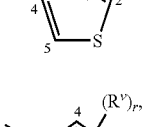

U-14
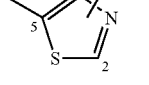

-continued
U-15 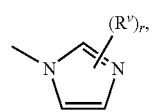
U-16 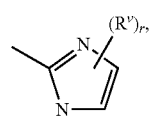
U-17 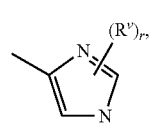
U-18 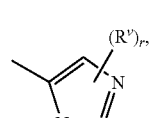
U-19 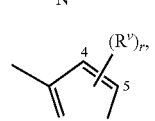
U-20 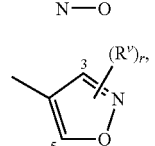
U-21 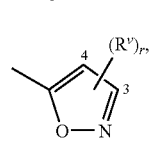
U-22 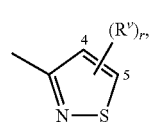
U-23 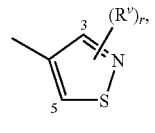
U-24 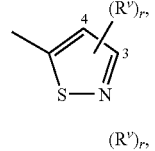
U-25 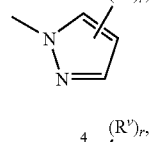
U-26 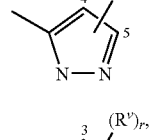
U-27 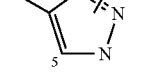
-continued
U-28 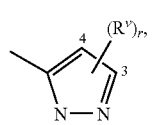
U-29 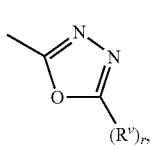
U-30 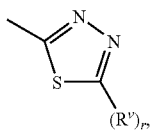
U-31 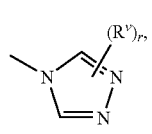
U-32 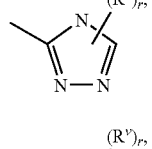
U-33 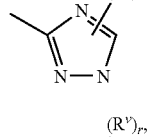
U-34 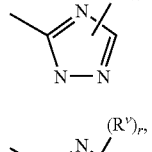
U-35 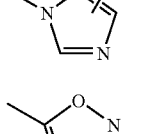
U-36 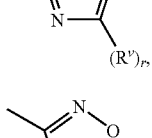
U-37 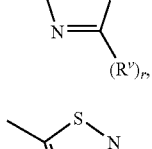
U-38 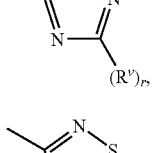
U-39

Note that when $Q^1$ is a 5- or 6-membered saturated or non-aromatic unsaturated heterocyclic ring optionally substituted with one or more substituents selected from the group of substituents as defined in the Summary of Invention for $Q^1$, one or two carbon ring members of the heterocycle can optionally be in the oxidized form of a carbonyl moiety.

Examples of a 5- or 6-membered saturated or non-aromatic unsaturated heterocyclic ring include the rings G-1 through G-35 as illustrated in Exhibit 3. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when $Q^1$ comprises a ring selected from G-28 through G-35, $G^2$ is selected from O, S or N. Note that when $G^2$ is N, the nitrogen atom can complete its valence by substitution with either H or the substituents corresponding to $R^v$ as defined in the Summary of Invention for $Q^1$ (i.e. $R^2$).

Exhibit 3

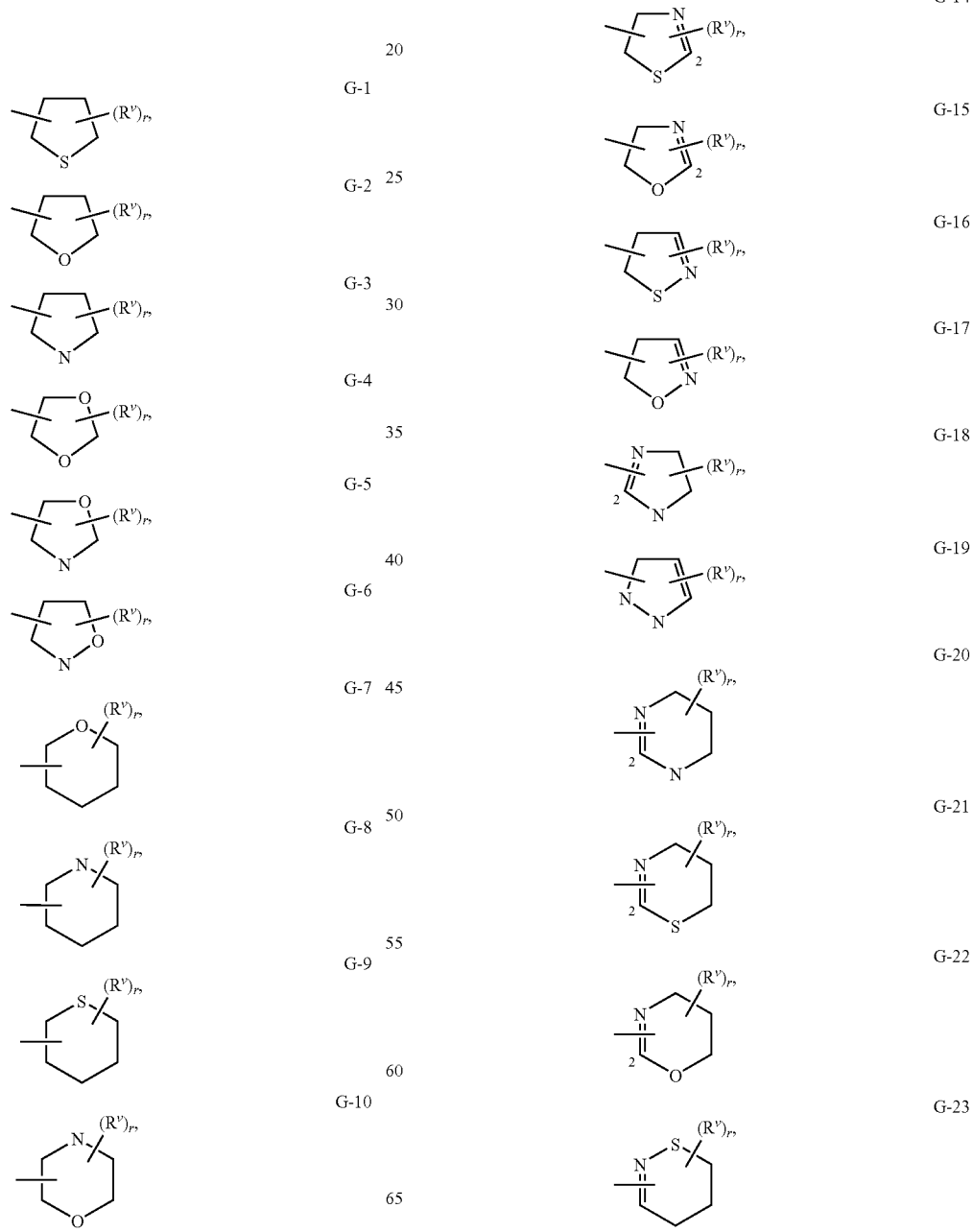

-continued

G-24 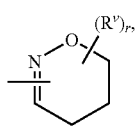

G-25 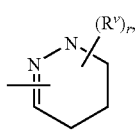

G-26 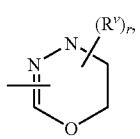

G-27 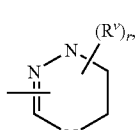

G-28 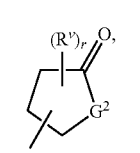

G-29 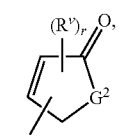

G-30 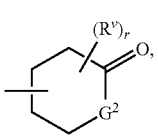

G-31 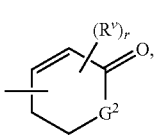

G-32 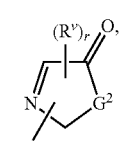

G-33 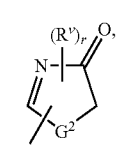

G-34 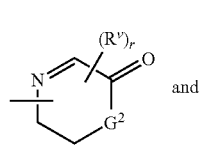 and

G-35 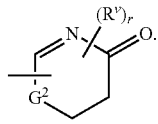

As noted above, $Q^1$ can be (among others) an 8-, 9- or 10-membered fused bicyclic ring system optionally substituted with one or more substituents selected from a group of substituents as defined in the Summary of Invention (i.e. $R^2$). Examples of 8-, 9- or 10-membered fused bicyclic ring system optionally substituted with from one or more substituents include the rings U-81 through U-123 illustrated in Exhibit 4 wherein $R^v$ is any substituent as defined in the Summary of the Invention for $Q^1$ (i.e. $R^2$), and r is typically an integer from 0 to 4.

Exhibit 4

U-81 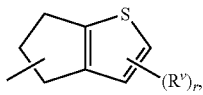

U-82 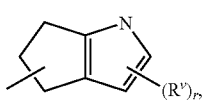

U-83 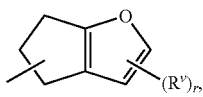

U-84 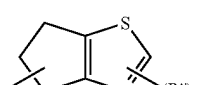

U-85 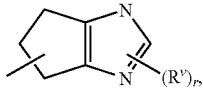

U-86 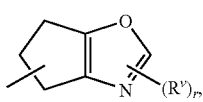

U-87 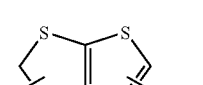

U-88 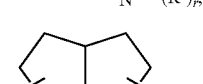

U-89 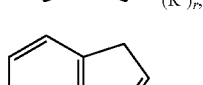

U-90 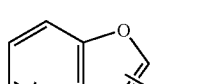

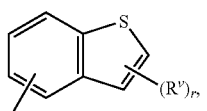 U-91
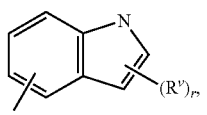 U-92
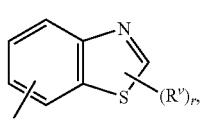 U-93
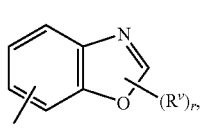 U-94
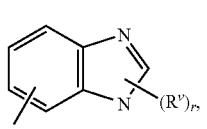 U-95
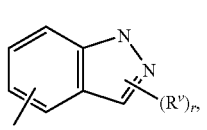 U-96
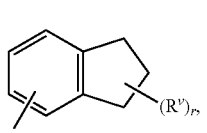 U-97
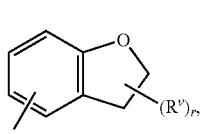 U-98
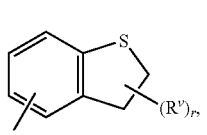 U-99
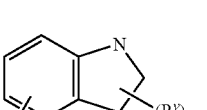 U-100
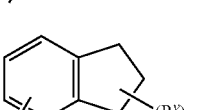 U-101
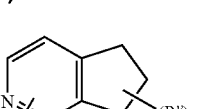 U-102
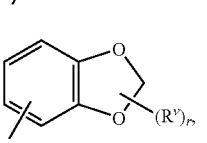 U-103
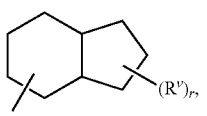 U-104
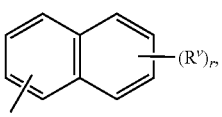 U-105
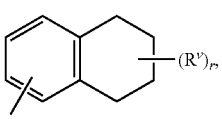 U-106
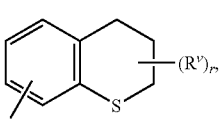 U-107
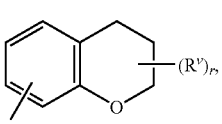 U-108
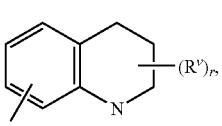 U-109
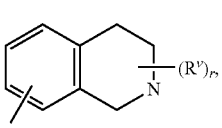 U-110
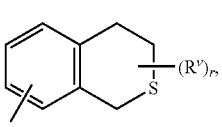 U-111
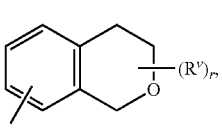 U-112
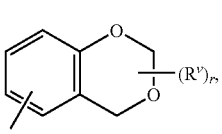 U-113
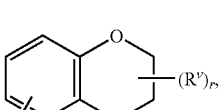 U-114
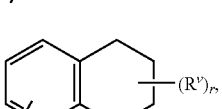 U-115
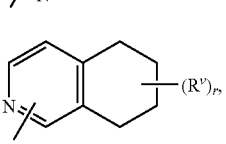 U-116

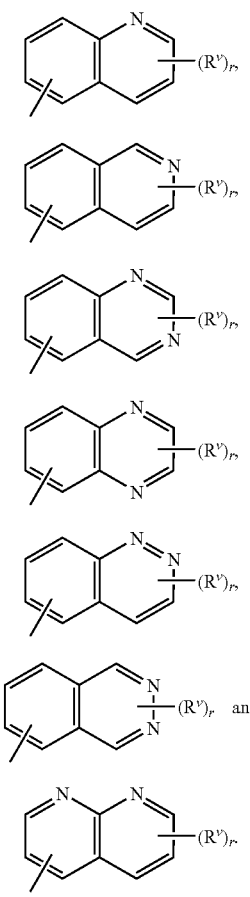

U-117
U-118
U-119
U-120
U-121
U-122 and
U-123

Although $R^v$ groups are shown in the structures U-1 through U-123, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For example, two possible enantiomers of Formula 1 are depicted as Formula 1' and Formula 1" involving the isoxazoline chiral center identified with an asterisk (*). Analogously, other chiral centers are possible at, for example, $R^5$.

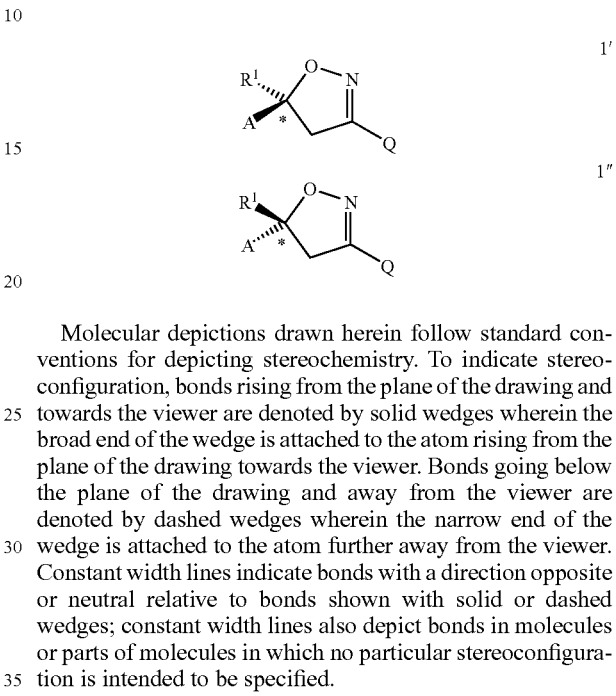

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

The more biologically active enantiomer is believed to be Formula 1'. Formula 1' often has the (S) configuration at the chiral carbon and Formula 1" often has the (R) configuration at the chiral carbon (e.g., when Q is phenyl and $R^1$ is trifluoromethyl).

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^5$ may themselves contain chiral centers. This invention comprises racemic mixtures as well as enriched and essentially pure stereo configurations at these additional chiral centers.

Compounds of this invention can exist as one or more conformational isomers due to restricted rotation about the amide bond linking Q-A to $Z^1$ and Q-B to $Z^2$. This invention comprises mixtures of conformational isomers. In addition, this invention includes compounds that are enriched in one conformer relative to others.

Compounds of this invention may exist as one or more crystalline polymorphs. This invention comprises both individual polymorphs and mixtures of polymorphs, including mixtures enriched in one polymorph relative to others.

One skilled in the art will appreciate that not all nitrogen-containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. As is well known in the art, when a compound containing a carboxylic acid group (i.e. $CO_2H$) is contacted with a base, the carboxylic acid group is converted to its salt derivative, also known as a carboxylate salt. For example, when a carboxylic acid group is reacted with sodium hydroxide, a sodium salt derivative is formed (i.e. $CO_2{}^\ominus Na^\oplus$). Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1. A compound of Formula 1 wherein Q is Q-A.

Embodiment 2. A compound of Embodiment 1 wherein $Z^1$ is $Z^1$-1.

Embodiment 3. A compound of Embodiment 1 wherein $Z^1$ is $Z^1$-2.

Embodiment 4. A compound of Embodiment 1 wherein $Z^1$ is $Z^1$-3.

Embodiment 5. A compound of Embodiment 1 wherein $Y^1$—$Y^2$—$Y^3$ is —CH=CH—S—, —CH=CH—O—, —S—CH=CH— or —O—CH=CH—.

Embodiment 6. A compound of Formula 1 wherein Q is Q-B.

Embodiment 7. A compound of Embodiment 6 wherein $Z^2$ is $Z^2$-1.

Embodiment 8. A compound of Embodiment 6 wherein $Z^2$ is $Z^2$-2.

Embodiment 9. A compound of Formula 1 wherein when Q is Q-B, $Z^2$ is $Z^2$-2, $R^{10}$ is $C_1$ alkyl substituted with one $R^{35}$, and $R^{35}$ is $CO_2H$ or a sodium salt derivative thereof, then $R^9$ is other than H.

Embodiment 10. A compound of Formula 1 wherein when Q is Q-B, $Z^2$ is $Z^2$-2, $R^{10}$ is $C_1$ alkyl substituted with one $R^{35}$, and $R^{35}$ is $CO_2H$ or a salt derivative thereof, then $R^9$ is other than H.

Embodiment 11. A compound of Embodiment 6 wherein $Z^2$ is $Z^2$-3.

Embodiment 12. A compound of Embodiment 11 wherein
$R^{11}$ is H;
$R^{12}$ is H or $C_1$-$C_3$ alkyl;
$R^{13}$ is H or $C_1$-$C_3$ alkyl;
$R^{14}$ is $C_1$-$C_6$ alkyl, $C_3$-$C_6$ cycloalkyl or $C_4$-$C_7$ alkylcycloalkyl optionally substituted with one or more substituents independently selected from $R^{35}$;
$R^{35}$ is H, halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$; and
$Y^4$ is CH.

Embodiment 12a. A compound of Embodiment 12 wherein
$R^{12}$ is H;
$R^{13}$ is H or $CH_3$;
$R^{14}$ is cyclopropyl or methylcyclopropyl optionally substituted with one or more substituents independently selected from $R^{35}$;
$R^{15}$ is H; and
$R^{35}$ is H or halogen.

Embodiment 13. A compound of Embodiment 6 wherein $Z^2$ is $Z^2$-4.

Embodiment 14. A compound of Embodiment 6 wherein $Z^2$ is $Z^2$-5.

Embodiment 15. A compound of Formula 1 wherein $R^1$ is $C_1$-$C_3$ haloalkyl.

Embodiment 16. A compound of Embodiment 15 wherein $R^1$ is $CF_3$.

Embodiment 17. A compound of Formula 1 wherein A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN.

Embodiment 17a. A compound of Embodiment 17 wherein A is a phenyl ring substituted with 2 substituents independently selected from the group consisting of halogen, $C_1$-$C_2$ haloalkyl and $C_1$-$C_2$ haloalkoxy.

Embodiment 18. A compound of Embodiment 17 wherein A is a phenyl ring substituted with 1 to 3 substituents independently selected from the group consisting of halogen, $CH_3$, $CF_3$, $OCF_3$, $OCF_2H$ and CN.

Embodiment 19. A compound of Formula 1 wherein A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN.

Embodiment 20. A compound of Embodiment 19 wherein A is a pyridyl ring substituted with 1 to 3 substituents independently selected from the group consisting of halogen, $CH_3$, $CF_3$, $OCF_3$, $OCF_2H$ and CN.

Embodiment 21. A compound of Formula 1 wherein $W^1$, $W^2$, $W^3$, $W^4$, $W^5$ and $W^6$ are O.

Embodiment 22. A compound of Embodiment 2 wherein
$R^5$ is H; or $C_1$-$C_6$ alkyl substituted with one or more substituents independently selected from $R^{22}$; and
$R^6$ is $C_1$-$C_6$ alkyl or $C_3$-$C_7$ alkylcycloalkyl, each optionally substituted with one or more substituents independently selected from $R^{33}$.

Embodiment 23. A compound of Embodiment 22 wherein $R^{22}$ and $R^{33}$ are independently selected from the group consisting of halogen, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN, $NO_2$, $CO_2R^{37}$, $C(=O)NR^{37}R^{38}$ and $Q^1$.

Embodiment 24. A compound of Embodiment 3 wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment 25. A compound of Embodiment 4 wherein
$L^1$ is $C_2$-$C_6$ alkylene optionally substituted with halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1.

Embodiment 26. A compound of Embodiment 13 wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment 27. A compound of Embodiment 14 wherein
$L^1$ is $C_2$-$C_6$ alkylene optionally substituted with one or more halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1.

Embodiments of this invention, including Embodiments 1-27 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-27 above as well as any other embodiments described herein, and any combination thereof, pertain to the compositions and methods of the present invention.

Combinations of Embodiments 1-27 are illustrated by:
Embodiment A. A compound of Formula 1 wherein
Q is Q-A;
$Z^1$ is $Z^1$-1;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN; and
$R^1$ is $C_1$-$C_3$ haloalkyl.

Embodiment B. A compound of Embodiment A wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment C. A compound of Formula 1 wherein
Q is Q-A;
$Z^1$ is $Z^1$-1;
A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN; and
$R^1$ is $C_1$-$C_3$ haloalkyl.

Embodiment D. A compound of Embodiment C wherein
A is a pyridyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment E. A compound of Embodiment A wherein
$R^5$ is H; or $C_1$-$C_6$ alkyl substituted with one or more substituents independently selected from $R^{22}$; and
$R^6$ is $C_1$-$C_6$ alkyl or $C_3$-$C_7$ alkylcycloalkyl, each optionally substituted with one or more substituents independently selected from $R^{33}$.

Embodiment F. A compound of Embodiment B wherein
$R^5$ is H; or $C_1$-$C_6$ alkyl substituted with one or more substituents independently selected from $R^{22}$; and
$R^6$ is $C_1$-$C_6$ alkyl or $C_3$-$C_7$ alkylcycloalkyl, each optionally substituted with one or more substituents independently selected from $R^{33}$.

Embodiment G. A compound of Embodiment C wherein
$R^5$ is H; or $C_1$-$C_6$ alkyl substituted with one or more substituents independently selected from $R^{22}$; and
$R^6$ is $C_1$-$C_6$ alkyl or $C_3$-$C_7$ alkylcycloalkyl, each optionally substituted with one or more substituents independently selected from $R^{33}$.

Embodiment H. A compound of Embodiment D wherein
$R^5$ is H; or $C_1$-$C_6$ alkyl substituted with one or more substituents independently selected from $R^{22}$; and
$R^6$ is $C_1$-$C_6$ alkyl or $C_3$-$C_7$ alkylcycloalkyl, each optionally substituted with one or more substituents independently selected from $R^{33}$.

Embodiment I. A compound of Embodiment E wherein $R^{22}$ and $R^{33}$ are independently selected from the group consisting of halogen, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN, $NO_2$, $CO_2R^{37}$, $C(=O)NR^{37}R^{38}$ and $Q^1$.

Embodiment J. A compound of Embodiment F wherein $R^{22}$ and $R^{33}$ are independently selected from the group consisting of halogen, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN, $NO_2$, $CO_2R^{37}$, $C(=O)NR^{37}R^{38}$ and $Q^1$.

Embodiment K. A compound of Embodiment G wherein $R^{22}$ and $R^{33}$ are independently selected from the group consisting of halogen, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN, $NO_2$, $CO_2R^{37}$, $C(=O)NR^{37}R^{38}$ and $Q^1$.

Embodiment L. A compound of Embodiment H wherein
$R^{22}$ and $R^{33}$ are independently selected from the group consisting of halogen, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN, $NO_2$, $CO_2R^{37}$, C(=O) $NR^{37}R^{38}$ and $Q^1$.

Embodiment M. A compound of Formula 1 wherein
Q is Q-A;
$Z^1$ is $Z^1$-2;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN; and
$R^1$ is $C_1$-$C_3$ haloalkyl.

Embodiment N. A compound of Embodiment M wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment O. A compound of Formula 1 wherein
Q is Q-A;
$Z^1$ is $Z^1$-2;
A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN; and
$R^1$ is $C_1$-$C_3$ haloalkyl.

Embodiment P. A compound of Embodiment O wherein
A is a pyridyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment Q. A compound of Embodiment M wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment R. A compound of Embodiment N wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment S. A compound of Embodiment O wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment T. A compound of Embodiment P wherein
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment U. A compound of Formula 1 wherein
Q is Q-A;
$Z^1$ is $Z^1$-3;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$L^1$ is $C_2$-$C_6$ alkylene optionally substituted with halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1

Embodiment V. A compound of Embodiment U wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment W. A compound of Formula 1 wherein
Q is Q-A;
$Z^1$ is $Z^1$-3;
A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$L^1$ is $C_2$-$C_6$ alkylene optionally substituted with halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1.

Embodiment X. A compound of Embodiment W wherein
A is a pyridyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment Y. A compound of Formula 1 wherein
Q is Q-B;
$Z^2$ is $Z^2$-3;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$R^{11}$ is H;
$R^{12}$ is H or $C_1$-$C_3$ alkyl;
$R^{13}$ is H or $C_1$-$C_3$ alkyl;
$R^{14}$ is $C_1$-$C_6$ alkyl, $C_3$-$C_6$ cycloalkyl or $C_4$-$C_7$ alkylcycloalkyl optionally substituted with one or more substituents independently selected from $R^{35}$; and
$R^{35}$ is H, halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$; and
$Y^4$ is CH.

Embodiment Z. A compound of Embodiment Y wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment AA. A compound of Formula 1 wherein
Q is Q-B;
$Z^2$ is $Z^2$-3;
A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$R^{11}$ is H;
$R^{12}$ is H or $C_1$-$C_3$ alkyl;
$R^{13}$ is H or $C_1$-$C_3$ alkyl;
$R^{14}$ is $C_1$-$C_6$ alkyl, $C_3$-$C_6$ cycloalkyl or $C_4$-$C_7$ alkylcycloalkyl optionally substituted with one or more substituents independently selected from $R^{35}$; and
$R^{35}$ is H, halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$.

Embodiment AB. A compound of Embodiment AA wherein
A is a pyridyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment AC. A compound of Formula 1 wherein
Q is Q-B;
$Z^2$ is $Z^2$-4;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment AD. A compound of Embodiment AC wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment AE. A compound of Formula 1 wherein
Q is Q-B;
$Z^2$ is $Z^2$-4;
A is a pyridyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$R^{16}$ and $R^{17}$ are independently $C_1$-$C_3$ alkyl optionally substituted with one or more substituents independently selected from $R^{35}$; and
$R^{35}$ is halogen, $C_1$-$C_3$ alkoxy, $C_1$-$C_3$ alkylthio or CN.

Embodiment AF. A compound of Embodiment AE wherein
A is a pyridyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment AG. A compound of Formula 1 wherein
Q is Q-B;
$Z^2$ is $Z^5$-5;
A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$L^1$ is $C_2$-$C_6$ alkylene optionally substituted with halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1.

Embodiment AH. A compound of Embodiment AG wherein
A is a phenyl ring substituted with 1 to 3 substituents independently selected from the group consisting of halogen, $CH_3$, $CF_3$, $OCF_3$, $OCF_2H$ and CN; and
$R^1$ is $CF_3$.

Embodiment AI. A compound of Formula 1 wherein
Q is Q-B;
$Z^2$ is $Z^2$-5;
A is a pyridyl ring substituted with 1 to 3 substituents independently selected from the group halogen, $C_1$-$C_3$ alkyl, $C_1$-$C_3$ haloalkyl, $C_1$-$C_3$ haloalkoxy and CN;
$R^1$ is $C_1$-$C_3$ haloalkyl;
$L^1$ is $C_2$-$C_6$ alkylene optionally substituted with halogen;
$R^{19}$ is $C_1$-$C_3$ alkyl optionally substituted with one or more substituents independently selected from $R^{35}$;
$R^{20}$ is H, CN, $NO_2$ or $CO_2R^{24}$;
$R^{35}$ is halogen, $C_1$-$C_3$ alkoxy, $C_1$-$C_3$ alkylthio or CN; and
q is 1.

Embodiment AJ. A compound of Embodiment AI wherein
A is a pyridyl ring substituted with 1 to 3 substituents independently selected from the group halogen, $CH_3$, $CF_3$, $OCF_3$, $OCF_2H$ and CN; and
$R^1$ is $CF_3$.

Embodiment AK. A compound of Embodiment Y wherein
A is a phenyl ring substituted with 2 substituents independently selected from the group consisting of halogen, $C_1$-$C_2$ haloalkyl and $C_1$-$C_2$ haloalkoxy;
$R^1$ is $CF_3$;
$R^{12}$ is H;
$R^{13}$ is H or $CH_3$;
$R^{14}$ is cyclopropyl or methylcyclopropyl optionally substituted with one or more substituents independently selected from $R^{35}$;
$R^{15}$ is H;
$R^{35}$ is H or halogen.

Specific embodiments include compounds of Formula 1 selected from the group consisting of:

N-[2-[(cyclopropylmethyl)amino]-2-oxoethyl]-4-[5-(3,5-dichlorophenyl)-4,5-dihydro-5-(trifluoromethyl)-3-isoxazolyl]-1-naphthalenecarboxamide, 4-[5-(3,5-dichlorophenyl)-4,5-dihydro-5-(trifluoromethyl)-3-isoxazolyl]-N-[2-[(2-methoxyethyl)amino]-2-oxoethyl]-1-naphthalenecarboxamide, 4-[5-(3,5-dichlorophenyl)-4,5-dihydro-5-(trifluoromethyl)-3-isoxazolyl]-N-[2-(S-methylsulfonimidoyl)ethyl]-1-naphthalenecarboxamide, N-[2-[(cyclopropyl-1-methylethyl)amino]-2-oxoethyl]-4-[5-(3,5-dichlorophenyl)-4,5-dihydro-5-(trifluoromethyl)-3-isoxazolyl]-1-naphthalenecarboxamide, 4-[5-(3,5-dichlorophenyl)-4,5-dihydro-5-(trifluoromethyl)-3-isoxazolyl]-N-[2-oxo-2-[(2-pyridinylmethyl)amino]ethyl]-1-naphthalenecarboxamide, N-[2-(cyclopropylamino)-2-oxoethyl]-4-[5-(3,5-dichlorophenyl)-4,5-dihydro-5-(trifluoromethyl)-3-isoxazolyl]-1-naphthalenecarboxamide, 1,1-dimethylethyl N-[2-[[[4-[5-(3,5-dichlorophenyl)-4,5-dihydro-5-(trifluoromethyl)-3-isoxazolyl]-1-naphthalenyl]carbonyl]amino]ethyl]carbamate, 1,1-dimethylethyl N-[3-[[[4-[5-(3,5-dichlorophenyl)-4,5-dihydro-5-(trifluoromethyl)-3-isoxazolyl]-1-naphthalenyl]carbonyl]amino]propyl]-N-methylcarbamate, N-[3-(acetylmethylamino)propyl]-4-[5-(3,5-dichlorophenyl)-4,5-dihydro-5-(trifluoromethyl)-3-isoxazolyl]-1-naphthalenecarboxamide, 4-[5-(3,5-dichlorophenyl)-4,5-dihydro-5-(trifluoromethyl)-3-isoxazolyl]-N-[2-[[2-(methylthio)ethyl]amino]-2-oxoethyl]-1-naphthalenecarboxamide, 4-[4,5-dihydro-5-(3,4,5-trichlorophenyl)-5-(trifluoromethyl)-3-isoxazolyl]-N-[2-[[2-(methylthio)ethyl]amino]-2-oxoethyl]-1-naphthalenecarboxamide, N-[2-(cyclopentylamino)-2-oxoethyl]-4-[5-(3,5-dichlorophenyl)-4,5-dihydro-5-(trifluoromethyl)-3-isoxazolyl]-1-naphthalenecarboxamide, 4-[5-(3,5-dichlorophenyl)-4,5-dihydro-5-(trifluoromethyl)-3-isoxazolyl]-N-[2-oxo-2-(1-piperidinyl)ethyl]-1-naphthalenecarboxamide, 4-[5-(3,5-dichlorophenyl)-4,5-dihydro-5-(trifluoromethyl)-3-isoxazolyl]-N-[2-(3,3-difluoro-1-pyrrolidinyl)-2-oxoethyl]-1-naphthalenecarboxamide, and 4-[5-(3,5-dichlorophenyl)-4,5-dihydro-5-(trifluoromethyl)-3-isoxazolyl]-N-[2-[S-methyl-N-(2,2,2-trifluoroacetyl)sulfonimidoyl]ethyl]-1-naphthalenecarboxamide.

Further specific embodiments include compounds of Formula 1 selected from Table A. The following abbreviations are used in Table A: c-Pr is cyclopropyl and entry a) is

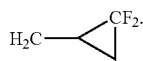

TABLE A

| $R^a$ | $R^b$ | $R^c$ | $R^d$ |
|---|---|---|---|
| Cl | Cl | H | c-Pr |
| Cl | Cl | H | $CH_2$-c-Pr |
| Cl | Cl | H | a) |
| Cl | Cl | $CH_3$ | c-Pr |
| Cl | Cl | $CH_3$ | $CH_2$-c-Pr |
| Cl | Cl | $CH_3$ | a) |
| Cl | $CF_3$ | H | c-Pr |
| Cl | $CF_3$ | H | $CH_2$-c-Pr |
| Cl | $CF_3$ | H | a) |
| Cl | $CF_3$ | $CH_3$ | c-Pr |
| Cl | $CF_3$ | $CH_3$ | $CH_2$-c-Pr |
| Cl | $CF_3$ | $CH_3$ | a) |
| Cl | $OCH_2CF_3$ | H | c-Pr |
| Cl | $OCH_2CF_3$ | H | $CH_2$-c-Pr |
| Cl | $OCH_2CF_3$ | H | a) |
| Cl | $OCH_2CF_3$ | $CH_3$ | c-Pr |
| Cl | $OCH_2CF_3$ | $CH_3$ | $CH_2$-c-Pr |
| Cl | $OCH_2CF_3$ | $CH_3$ | a) |
| Br | $CF_3$ | H | c-Pr |
| Br | $CF_3$ | H | $CH_2$-c-Pr |
| Br | $CF_3$ | H | a) |
| Br | $CF_3$ | $CH_3$ | c-Pr |
| Br | $CF_3$ | $CH_3$ | $CH_2$-c-Pr |
| Br | $CF_3$ | $CH_3$ | a) |
| $CF_3$ | $CF_3$ | H | c-Pr |
| $CF_3$ | $CF_3$ | H | $CH_2$-c-Pr |
| $CF_3$ | $CF_3$ | H | a) |
| $CF_3$ | $CF_3$ | $CH_3$ | c-Pr |
| $CF_3$ | $CF_3$ | $CH_3$ | $CH_2$-c-Pr |
| $CF_3$ | $CF_3$ | $CH_3$ | a) |

Further noteworthy as embodiments of the present invention are compositions for controlling an invertebrate pest comprising a compound of any of the preceding Embodiments (i.e. in a biologically effective amount), as well as any other embodiments described herein, and any combinations thereof, and at least one additional component selected from the group consisting of a surfactant, a solid diluent and a liquid diluent, said compositions optionally further comprising at least one additional biologically active compound or agent.

Further Embodiments of the present invention include:

Embodiment A1. A composition for protecting an animal from an invertebrate parasitic pest comprising a compound of Formula 1 or any one of Embodiments 1-27 or A-AK and at least one veterinarily acceptable carrier, said composition optionally further comprising at least one additional parasiticidally active compound.

Embodiment A2. The composition of Embodiment A1 wherein at least one additional parasiticidally active compound is an anthelmintic.

Embodiment A3. The composition of Embodiment A1 wherein at least one additional parasiticidally active compound is selected from the group consisting of macrocyclic lactones, benzimidazoles, salicylamides, substituted phenols, pyrimidines, cyclic depsipeptides, piperazine salts, nitroscanate, praziquantel and imidazothiazoles.

Embodiment A4. The composition of Embodiment A3 wherein at least one additional parasiticidally active compound is selected from the group consisting of avermectins, milbemycins and spinosyns.

Embodiment A5. The composition of Embodiment A1 wherein at least one additional parasiticidally active compound is selected from the group consisting of abamectin, doramectin, emamectin, eprinomectin, ivermectin, selamectin, milbemycin, moxidectin and pyrantel.

Embodiment A6. The composition of Embodiment A1 in a form for oral administration.

Embodiment A7. The composition of Embodiment A1 in a form for topical administration.

Embodiment A8. The composition of Embodiment A1 in a form for parenteral administration.

Embodiments of the invention further include methods for controlling an invertebrate pest comprising contacting the invertebrate pest or its environment with a biologically effective amount of a compound of any of the preceding Embodiments (e.g., as a composition described herein). Of particular note is a method for protecting an animal comprising administering to the animal a parasiticidally effective amount of a compound of any of the preceding Embodiments (e.g., as a composition described herein).

Further Embodiments of the present invention include:

Embodiment B1. The method for protecting an animal from an invertebrate parasitic pest comprising administering to the animal a parasiticidally effective amount of a compound of Formula 1 as described in the Summary of the Invention or any one of Embodiments 1-27 or A-AK.

Embodiment B3. The method of Embodiment B1 wherein the parasiticidally effective amount of the compound of Formula 1 is administered orally.

Embodiment B4. The method of Embodiment B1 wherein the parasiticidally effective amount of the compound of Formula 1 is administered parenterally.

Embodiment B5. The method of Embodiment B1 wherein the parasiticidally effective amount of the compound of Formula 1 is administered by injection.

Embodiment B6. The method of Embodiment B1 wherein the parasiticidally effective amount of the compound of Formula 1 is administered topically.

Embodiment B7. The method of Embodiment B1 wherein the animal to be protected is a vertebrate.

Embodiment B8. The method of Embodiment B7 wherein the animal to be protected is a mammal, avian or fish.

Embodiment B9. The method of Embodiment B8 wherein the animal to be protected is a human.

Embodiment B10. The method of Embodiment B8 wherein the animal to be protected is livestock.

Embodiment B11. The method of Embodiment B8 wherein the animal to be protected is a canine.

Embodiment B11a. The method of Embodiment B8 wherein the animal to be protected is a dog.

Embodiment B12. The method of Embodiment B8 wherein the animal to be protected is a feline.

Embodiment B12a. The method of Embodiment B8 wherein the animal to be protected is a cat.

Embodiment B13. The method of Embodiment B1 wherein the invertebrate parasitic pest is an ectoparasite.

Embodiment B14. The method of Embodiment B1 wherein the invertebrate parasitic pest is an endoparasite or helminth.

Embodiment B15. The method of Embodiment B1 wherein the invertebrate parasitic pest is an arthropod.

Embodiment B16. The method of Embodiment B1 wherein the invertebrate parasitic pest is a fly, mosquito, mite, tick, louse, flea, maggot, bed bug or kissing bug.

Embodiment B17. The method of Embodiment B16 wherein the invertebrate parasitic pest is a mosquito.

Embodiment B18. The method of Embodiment B16 wherein the invertebrate parasitic pest is a tick or mite.

Embodiment B19. The method of Embodiment B16 wherein the invertebrate parasitic pest is a louse.

Embodiment B20. The method of Embodiment B16 wherein the invertebrate parasitic pest is a flea.

Embodiment B21. The method of Embodiment B16 wherein the invertebrate parasitic pest is a bed bug or kissing bug.

Embodiment B22. The method of Embodiment B16 wherein the animal is a cat or dog and the invertebrate parasitic pest is a flea, tick or mite.

Embodiment B23. The method of Embodiment B1 wherein the parasiticidally effective amount of a compound of Formula 1 is administered monthly or at a longer interval.

Embodiment B24. The method of Embodiment B23 wherein the parasiticidally effective amount of a compound of Formula 1 is administered once a month.

Embodiment B25. The method of Embodiment B23 wherein the parasiticidally effective amount of a compound of Formula 1 is administered once every six months.

The compounds of Formula 1 or any of Embodiments 1-27 or Embodiments A-AK can be used for the protection of an animal from an invertebrate parasitic pest by oral, topical or parenteral administration of the compound.

Therefore, the invention is understood to include the compounds of Formula 1 or any of Embodiments 1-27 or Embodiments A-AK (and compositions containing them) for use as an animal medicament, or more particularly a parasiticidal animal medicament. The animals to be protected are as defined in any of Embodiments B7-B12a. The invertebrate parasitic pests are as defined in any of Embodiments B13-B21. The medicament may be in oral, topical or parenteral dosage forms.

The invention is also understood to include the use of compounds of Formula 1 or any of Embodiments 1-27 or Embodiments A-AK in the manufacture of medicaments for the protection of an animal from a an invertebrate parasitic pest. The animals to be protected are as defined in any of Embodiments B7-B12a. The invertebrate parasitic pests are as defined in any of Embodiments B13-B21. The medicament may be in oral, topical or parenteral dosage forms.

The invention is also understood to include compounds of Formula 1 or any of Embodiments 1-27 or Embodiments A-AK for use in the manufacture of medicaments for the protection of an animal from an invertebrate parasitic pest. The animals to be protected are as defined in any of Embodiments B7-B12a. The invertebrate parasitic pests are as defined in any of Embodiments B13-B21. The medicament may be in oral, topical or parenteral dosage forms.

The invention is also understood to include compounds of Formula 1 or any of Embodiments 1-27 or Embodiments A-AK packaged and presented for the protection of an animal from an invertebrate parasitic pest. The animals to be protected are as defined in any of Embodiments B7-B12a. The invertebrate parasitic pests are as defined in any of Embodiments B13-B21. The compounds of the invention may be packaged and presented as oral, topical or parenteral dosage forms.

The invention is also understood to include a process for manufacturing a composition for protecting an animal from an invertebrate parasitic pest characterized in that a compound of claim 1 is admixed with at least one pharmaceutically or veterinarily acceptable carrier. The animals to be protected are as defined in any of Embodiments B7-B12a. The invertebrate parasitic pests are as defined in any of Embodiments B13-B21. The compositions of the invention may be packaged and presented as oral, topical or parenteral dosage forms.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a biologically effective amount of a compound of any of the preceding Embodiments, as well as any other embodiments described herein, and any combinations thereof, and at least one additional component selected from the group consisting of a surfactant, a solid diluent and a liquid diluent, said compositions optionally further comprising a biologically effective amount of at least one additional biologically active compound or agent. Embodiments of the invention further include methods for controlling an invertebrate pest comprising contacting the invertebrate pest or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a biologically effective amount of a compound of any of the preceding Embodiments and a propellant. Embodiments of the invention further include a bait composition for controlling an invertebrate pest comprising a biologically effective amount of a compound of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

One or more of the following methods and variations as described in Schemes 1-30 can be used to prepare the compounds of Formula 1. The definitions of $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, A, $L^1$, $W^1$, $W^4$, $W^5$, $Y^1$, $Y^2$, $Y^3$, $Y^4$, m and n in the compounds of Formulae 1-33 below are as defined above in the Summary of the Invention unless otherwise noted. Formulae 1a-1j are various subsets of Formula 1, and all substituents for Formulae 1a-1j are as defined above for Formula 1.

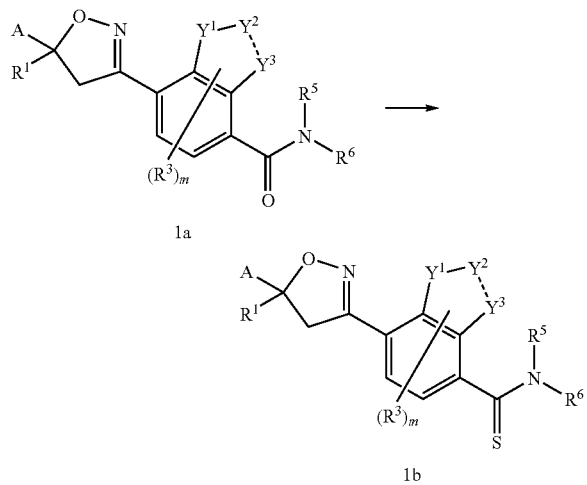

As shown in Scheme 1, compounds of Formula 1b (Formula 1 wherein Q is Q-A, $Z^1$ is $Z^1$-1 and $W^1$ is S) can be prepared by treatment of corresponding amide compounds of Formula 1a (compounds of Formula 1 wherein Q is Q-A, $Z^1$ is $Z^1$-1 and $W^1$ is O) with a thio transfer reagent, such as $P_2S_5$ (see for example, E. Klingsberg et al., *J. Am. Chem. Soc.* 1951, 72, 4988; E. C. Taylor Jr. et al., *J. Am. Chem. Soc.* 1953, 75, 1904; R. Crossley et al., *J. Chem. Soc. Perkin Trans. 1* 1976, 977) or Lawesson's reagent (2,5-bis(4-methoxyphenyl)-1,3-dithia-2,4-diphosphetane-2,4-disulfide; see, for example, S. Prabhakar et al. *Synthesis,* 1984, 829). The method of Scheme 1 can be conducted over a wide range of temperatures, including from about 50 to about 150° C. Of note are temperatures from about 70 to about 120° C., which typically provide fast reaction rates and high product yields.

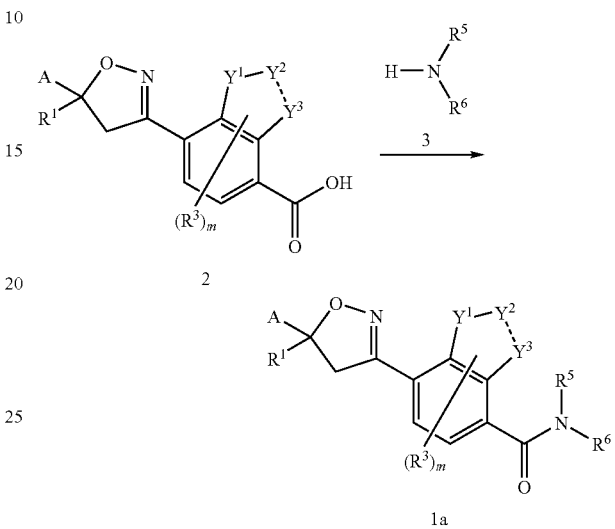

As shown in Scheme 2, compounds of Formula 1a can be prepared by coupling carboxylic acids of Formula 2 with appropriately substituted amino compounds of Formula 3. This reaction is generally carried out in the presence of a dehydrating coupling reagent, such as dicyclohexyl carbodiimide (DCC), 1-(3-dimethylaminopropyl)-3-ethylcarbodiimide, 1-propanephosphonic acid cyclic anhydride or carbonyl diimidazole, in the presence of a base such as triethylamine, pyridine, 4-(dimethylamino)pyridine or N,N-diisopropylethylamine in an anhydrous aprotic solvent such as dichloromethane or tetrahydrofuran at a temperature typically between room temperature and 70° C.

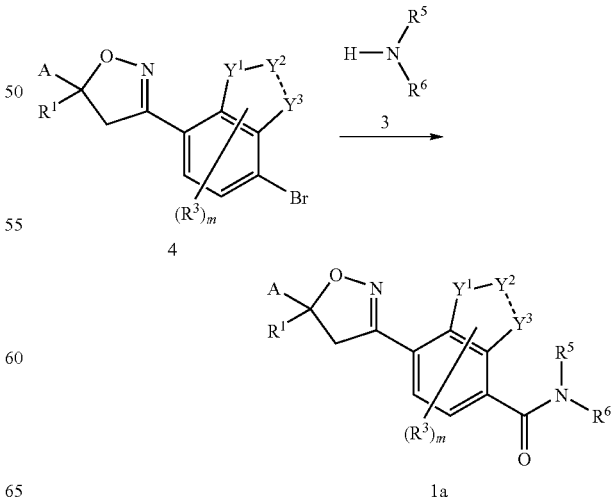

As shown in Scheme 3, compounds of Formula 1a can also be prepared by aminocarbonylation of aryl bromides of Formula 4 with appropriately substituted amino compounds of Formula 3. This reaction is typically carried out with an aryl bromide of Formula 4 in the presence of a palladium catalyst under CO atmosphere. The palladium catalysts used for the present method typically comprises palladium in a formal oxidation state of either 0 (i.e. Pd(0)) or 2 (i.e. Pd(II)). A wide variety of such palladium-containing compounds and complexes are useful as catalysts for the present method. Examples of palladium-containing compounds and complexes useful as catalysts in the method of Scheme 3 include $PdCl_2(PPh_3)_2$ (bis(triphenylphosphine)palladium (II) dichloride), $Pd(PPh_3)_4$ (tetrakis(triphenylphosphine)palladium(0)), $Pd(C_5H_7O_2)_2$ (palladium(II) acetyl-acetonate), $Pd_2(dba)_3$ (tris(dibenzylideneacetone)dipalladium(0)), and [1,1'-bis(diphenyl-phosphino)ferrocene]dichloropalladium(II). The method of Scheme 3 is generally conducted in a liquid phase, and therefore to be most effective the palladium catalyst preferably has good solubility in the liquid phase. Useful solvents include, for example, ethers such as 1,2-dimethoxyethane, amides such as N,N-dimethylacetamide, and non-halogenated aromatic hydrocarbons such as toluene.

The method of Scheme 3 can be conducted over a wide range of temperatures, ranging from about 25 to about 150° C. Of note are temperatures from about 60 and about 110° C., which typically provide fast reaction rates and high product yields. The general methods and procedures for aminocarbonylation with an aryl bromide and an amine are well known in the literature; see, for example, H. Horino et al., *Synthesis* 1989, 715; and J. J. Li, G. W. Gribble, editors, *Palladium in Heterocyclic Chemistry: A Guide for the Synthetic Chemist*, Elsevier Science Ltd, 2000.

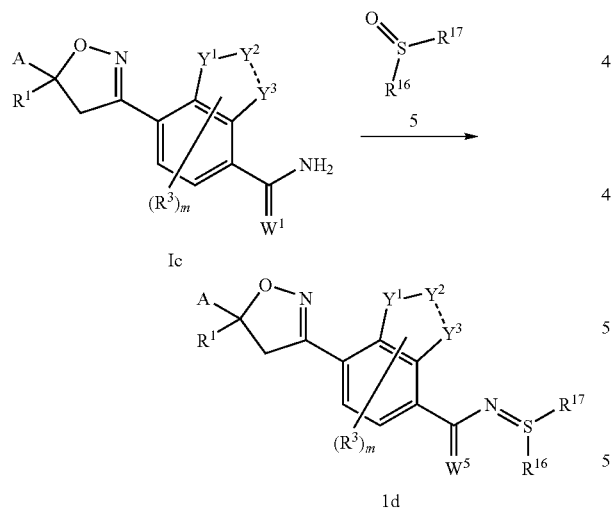

As shown in Scheme 4, compounds of Formula 1d (compounds of Formula 1 wherein Q is Q-A and $Z^1$ is $Z^1$-2) wherein $W^5$ is the same as $W^1$ can be prepared by the condensation of compounds of Formula 1c (Formula 1 wherein Q is Q-A, $Z^1$ is $Z^1$-1, and $R^5$ and $R^6$ are H) wherein $W^1$ is O or S with compounds of Formula 5 in the presence of condensing agents. The reaction conditions are well illustrated in previous art; for example, see, T. Schmidt et al., WO2007/006670. Suitable condensing agents include carboxylic acid anhydrides, dicyclohexylcarbodiimide, sulfuryl chloride, phosphorus(V) oxide and phosphorus oxychloride.

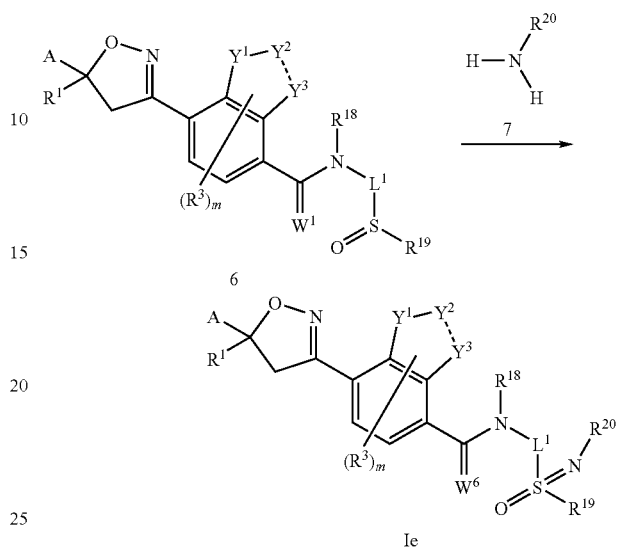

As shown in Scheme 5, compounds of Formula 1e (Formula 1 wherein Q is Q-A, $Z^1$ is $Z^1$-3, and q is 1) wherein $W^6$ is the same as $W^1$ can be prepared by treating the sulfoxides of Formula 6 with amino compounds of Formula 7 using $Rh_2(OAc)_4$ as a catalyst in combination with iodobenzene diacetate and magnesium oxide. The general procedure is well demonstrated in the literature, for example, see, H. Okamura & C. Bolm, *Org. Lett.*, 2004, 6, 1305.

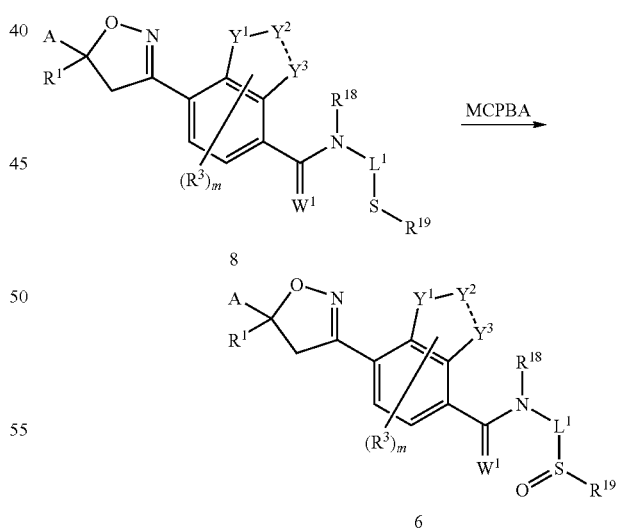

As shown in Scheme 6, compounds of Formula 6 can be prepared from compounds of Formula 8 by treatment with m-chloroperbenzoic acid (MCPBA). Oxidation of thioethers of Formula 8 with 1.0 equivalent of MCPBA at low temperature, preferably at −78 to −40° C., provides the sulfoxides of Formula 6 in good yield. The compounds of Formula 8 can be prepared by the methods illustrated in Schemes 1, 2 and 3.

Scheme 7

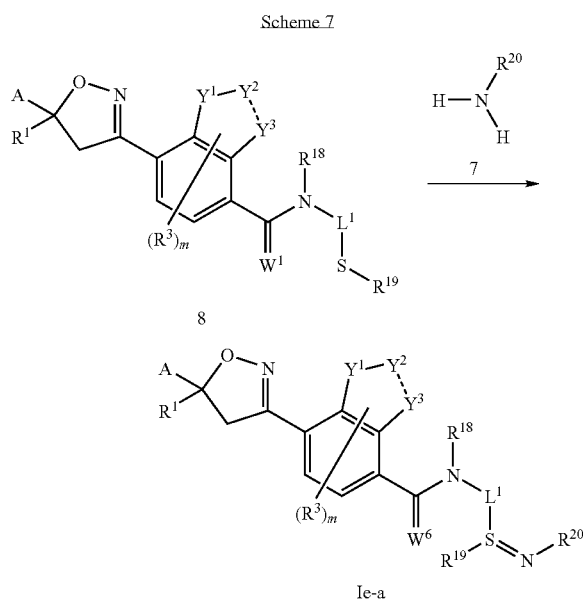

As shown in Scheme 7, compounds of Formula 1e-a (Formula 1 wherein Q is Q-A, $Z^1$ is $Z^1$-3, and q is 0) wherein $W^6$ is the same as $W^1$ can be prepared from compounds of Formula 8 analogous to the method of Scheme 5 using $Rh_2(OAc)_4$ as a catalyst in combination with iodobenzene diacetate and magnesium oxide.

Scheme 8

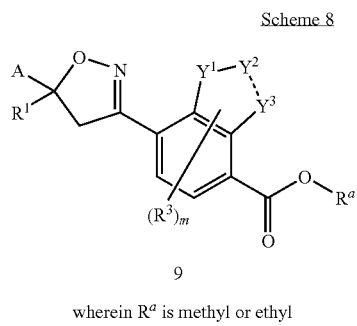

wherein $R^a$ is methyl or ethyl

As shown in Scheme 8, compounds of Formula 2 can be prepared by hydrolysis of the esters of Formula 9, wherein $R^a$ is methyl or ethyl. In this method, compounds of Formula 9 are converted to the corresponding carboxylic acids of Formula 2 by general procedures well known in the art. For example, treatment of a methyl or ethyl ester of Formula 9 with aqueous lithium hydroxide in tetrahydrofuran, followed by acidification yields the corresponding carboxylic acid of Formula 2.

Scheme 9

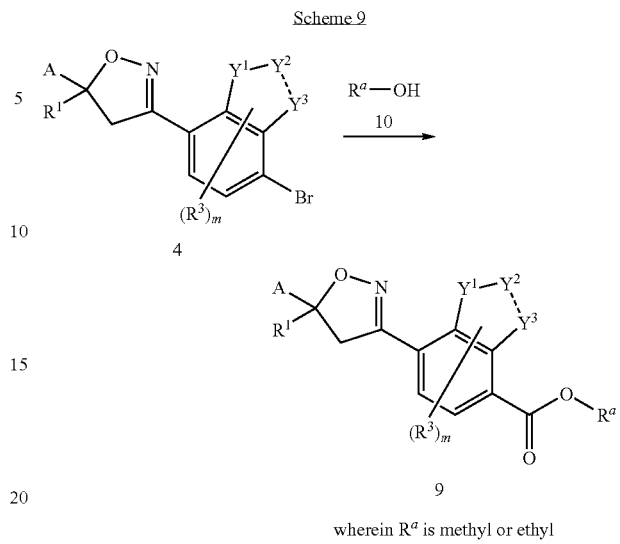

wherein $R^a$ is methyl or ethyl

Alcohols of Formula 10 can substituted for the amines of Formula 3 in the reaction of Scheme 3, to yield the esters of Formula 9 as shown in Scheme 9.

Scheme 10

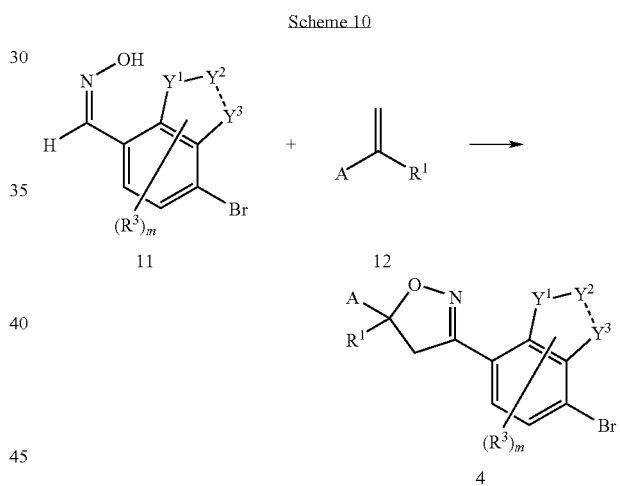

As shown in Scheme 10, compounds of Formula 4 can be prepared by the 1,3-dipolar cycloaddition of styrenes of Formula 12 with nitrile oxides derived from oximes of Formula 11. This reaction typically proceeds through the intermediacy of an in situ generated hydroxamyl chloride, which is dehydrochlorinated to the nitrile oxide, which then undergoes 1,3-dipolar cycloaddition with the styrene of Formula 12 to afford compounds of Formula 4. In a typical procedure, a chlorinating reagent such as sodium hypochlorite, N-chlorosuccinimide, or chloramine-T is combined with the oxime in the presence of the styrene. Depending on the conditions, amine bases such as pyridine or triethylamine may be necessary to facilitate the dehydrochlorination reaction. The reaction can be run in a wide variety of solvents including tetrahydrofuran, diethyl ether, methylene chloride, dioxane, and toluene with temperatures ranging from room temperature to the reflux temperature of the solvent. General procedures for cycloaddition of nitrile oxides with olefins are well documented in the chemical literature; for example, see Lee, *Syn-*

Scheme 11

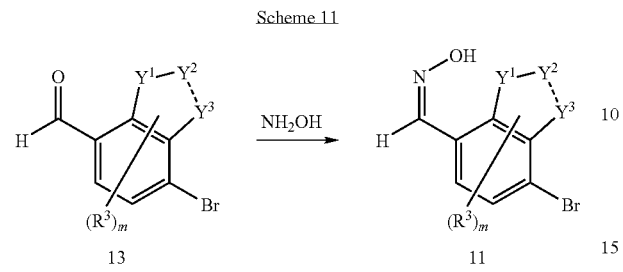

As shown in Scheme 11, the oximes of Formula 11 can be prepared by the reaction of aldehydes of Formula 13 with hydroxylamine according to known literature procedures. For example, see, H. K. Jung et al. *Bioorg. Med. Chem.* 2004, 12, 3965.

Scheme 12

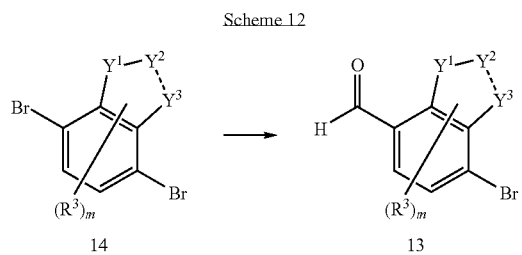

As shown in Scheme 12, aldehydes of Formula 13 can be prepared by methods known in art. For example, preparation of the compounds of Formula 13, wherein $Y^1—Y^2—Y^3$ is —CH=CH—NH($R^3$)— or —NH($R^3$)—CH=CH—, is disclosed by Lianhai Li et al. *Tetrahedron Lett.* 2003, 44, 5987. The dibromo compounds of Formula 14, wherein $Y^1—Y^2—Y^3$ is —CH=CH—N($R^3$)—, are a class of compounds reported in the chemical literature; for example, see, A. P. Dobbs et al. *Synlett* 1999, 10, 1594.

Scheme 13

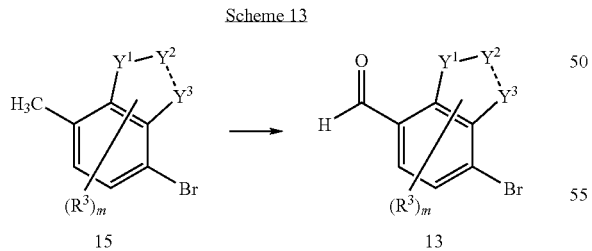

As shown in Scheme 13, aldehydes of Formula 13 can also be prepared from methyl derivatives of Formula 15 by methods known in synthetic art, for example, see, E. R. Mewshaw et al. WO2004/1303941. The compounds of Formula 15, wherein $Y^1—Y^2—Y^3$ is —CH=CH—O—, —CH=CH—S—, —O—CH=CH—, or —S—CH=CH—, can be prepared by general methods known in the art; some are also commercially available.

Scheme 14

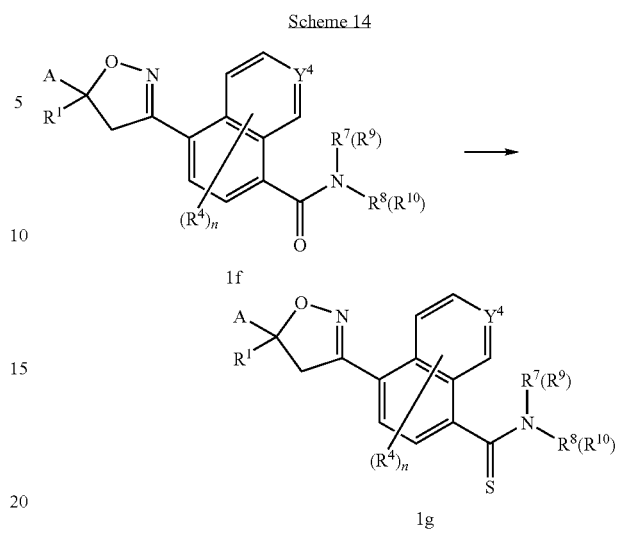

As shown in Scheme 14, compounds of Formula 1g (Formula 1 wherein Q is Q-B, $Z^2$ is $Z^2$-1 or $Z^2$-2 and $W^2$ or $W^3$ are S) can be prepared by treatment of corresponding amide compounds of Formula 1f (compounds of Formula 1 wherein Q is Q-B, $Z^2$ is $Z^2$-1 or $Z^2$-2 and $W^2$ or $W^3$ are O) with a thio transfer reagent. The method of Scheme 14 is conducted as described for Scheme 1.

Scheme 15

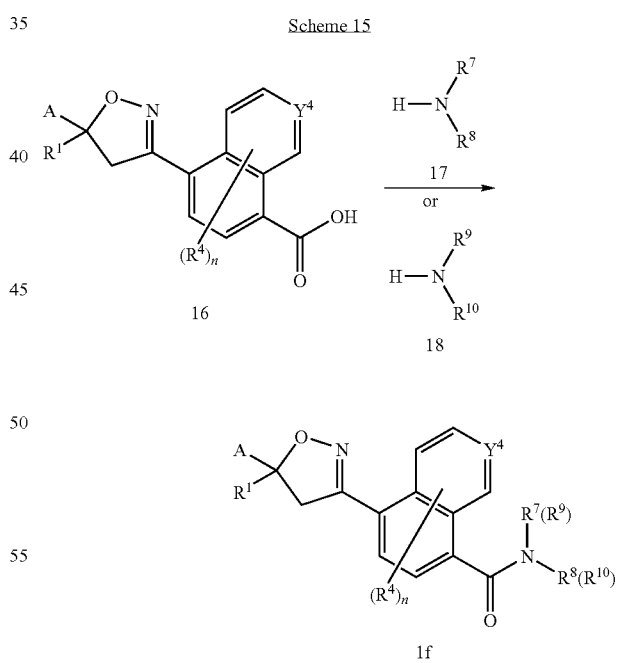

As shown in Scheme 15, compounds of Formula 1f (Formula 1 wherein Q is Q-B, $Z^2$ is $Z^2$-1 or $Z^2$-2 and $W^2$ or $W^3$ are O) can be prepared by coupling the corresponding carboxylic acids of Formula 16 with appropriately substituted amino compounds of Formula 17 or 18. The method of Scheme 15 is conducted as described for Scheme 2.

Scheme 16

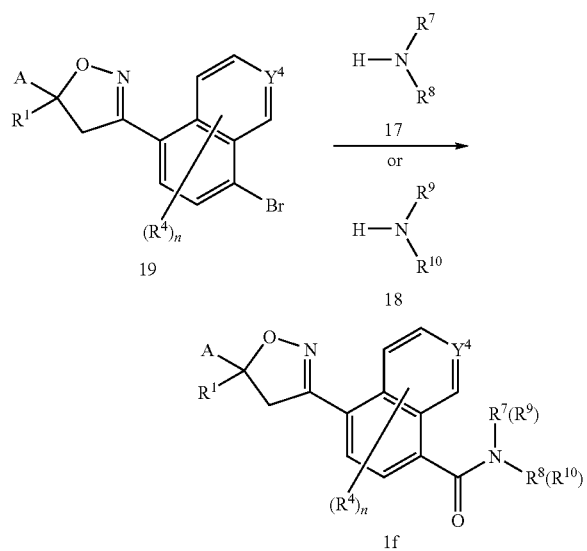

As shown in Scheme 16, compounds of Formula 1f (Formula 1 wherein Q is Q-B, $Z^2$ is $Z^2$-1 or $Z^2$-2, and $W^2$ or $W^3$ are O) can also be prepared by aminocarbonylation of aryl bromides of Formula 19 with appropriately substituted amino compounds of Formula 17 or 18. The method of Scheme 16 is conducted as described for Scheme 3.

Scheme 17

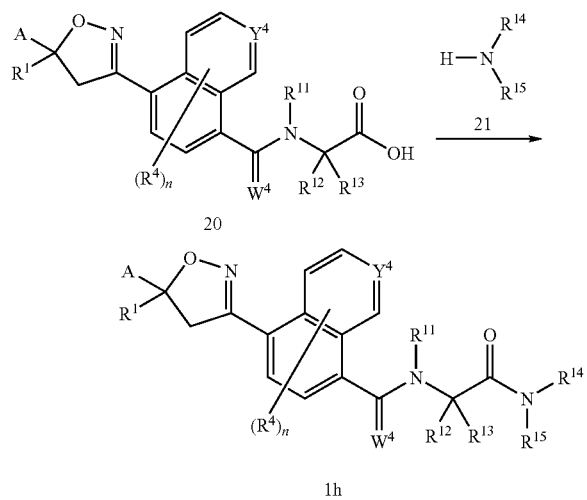

As shown in Scheme 17, amides of Formula 1h (Formula 1 wherein Q is Q-B and $Z^2$ is $Z^2$-3) can be prepared by coupling the corresponding acids of Formula 20 with appropriately substituted amino compounds of Formula 21. Amide formation reactions are well known in the synthetic art. Treating acids of Formula 20 with amino compounds of Formula 21 in the presence of dehydrating reagents, such as carboxylic acid chlorides, DCC or polymer-supported (PS)-carbodiimide, in an anhydrous aprotic solvent such as dichloromethane provides compounds of Formula 1h. The method of Scheme 17 is illustrated in Step C of Example 1.

Scheme 18

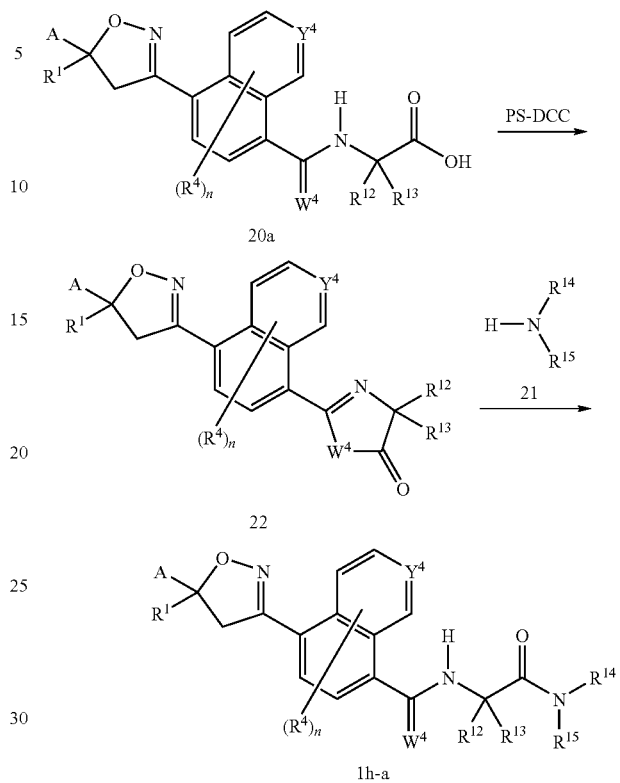

As shown in Scheme 18, amides of Formula 1h-a (Formula 1h wherein $R^{11}$ is H) can be prepared by the corresponding acids of Formula 20a (compounds of Formula 20 wherein $R^{11}$ is H) through intermediates of Formula 22 and further reaction with the appropriately substituted amino compounds of Formula 21. The cyclization reaction is typically carried out using dehydrating reagents, such as polymer-supported (PS)-carbodiimide or dicyclohexyl carbodiimide (DCC) in an anhydrous aprotic solvent such as dichloromethane at room temperature. The intermediates of Formula 22 can be used directly without any purification if polymer-supported DCC is used as the dehydrating reagent. The subsequent amide bond formation can be achieved through mixing the intermediates of Formula 22 with amino compounds of Formula 21 in N,N-dimethylformamide heated to a temperature between 100 and 180° C. using microwave irradiation. The method of Scheme 18 is illustrated in Example 2.

Scheme 19

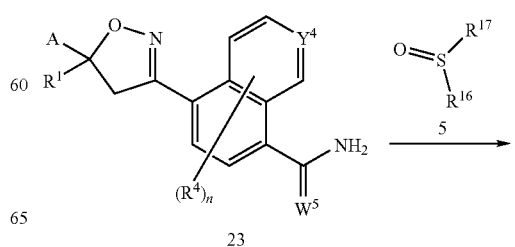

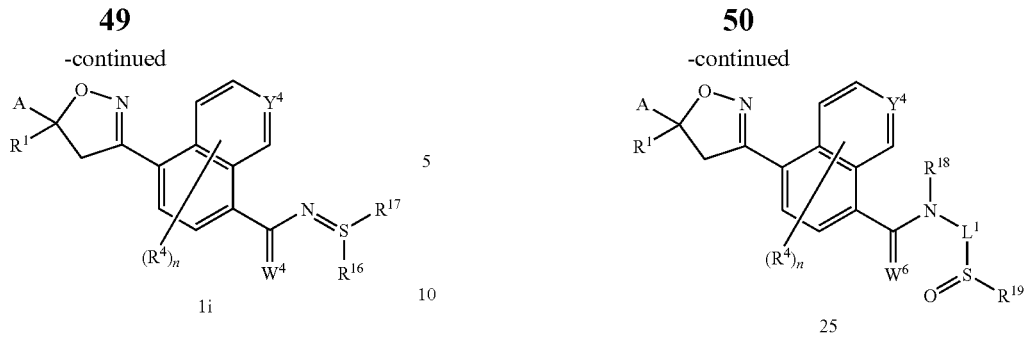

As shown in Scheme 19, compounds of Formula 1i (Formula 1 wherein Q is Q-B and $Z^2$ is $Z^2$-4) wherein $W^5$ is O or S can be prepared by coupling compounds of Formula 23 with compounds of Formula 5. The method of Scheme 19 is conducted as described for Scheme 4.

As shown in Scheme 21, sulfoxides of Formula 25 can be prepared by treating sulfides of Formula 26 with MCPBA. The method of Scheme 21 is conducted as described for Scheme 6 and is illustrated in Step B of Example 3.

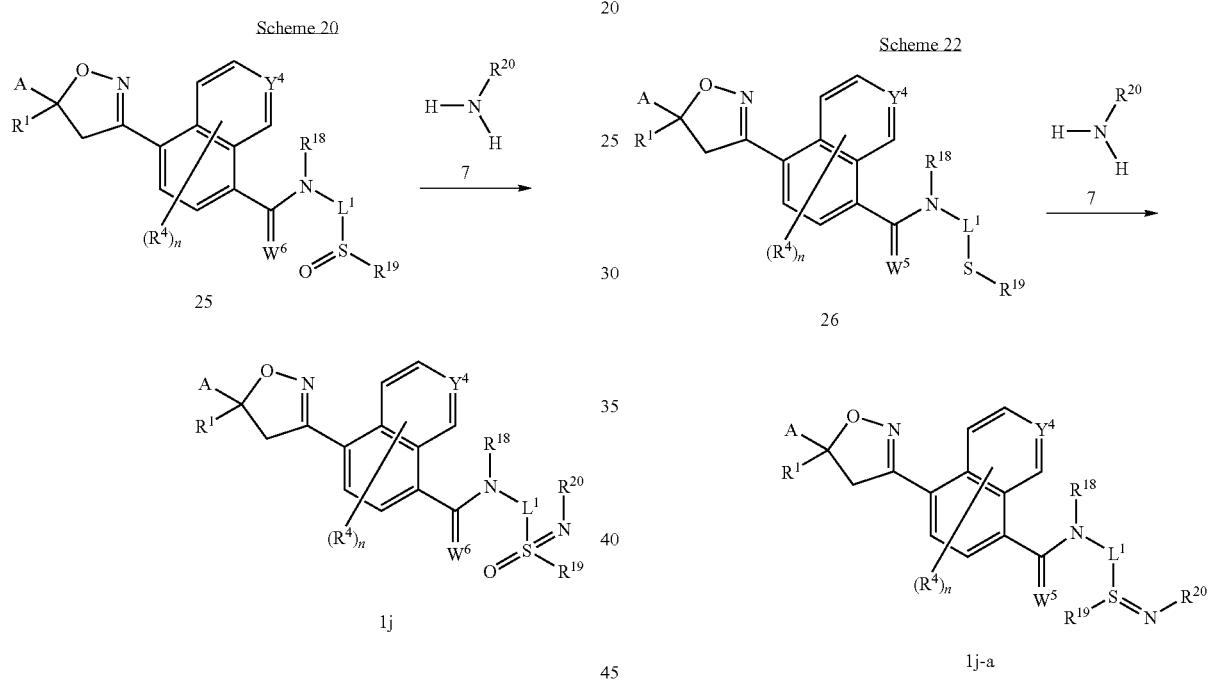

As shown in Scheme 20, compounds of Formula 1j (Formula 1 wherein Q is Q-B, $Z^2$ is $Z^2$-5, and q is 1) wherein $W^5$ is O or S can be prepared by treating sulfoxides of Formula 25 with amines of Formula 7. The method of Scheme 20 is conducted as described for Scheme 5 and is illustrated in Step C of Example 3.

As shown in Scheme 22, compounds of Formula 1j-a (Formula 1 wherein Q is Q-B, $Z^2$ is $Z^2$-5, and q is 0) can be prepared from sulfides of Formula 26 and amines of Formula 7. The method of Scheme 22 is conducted as described for Scheme 7.

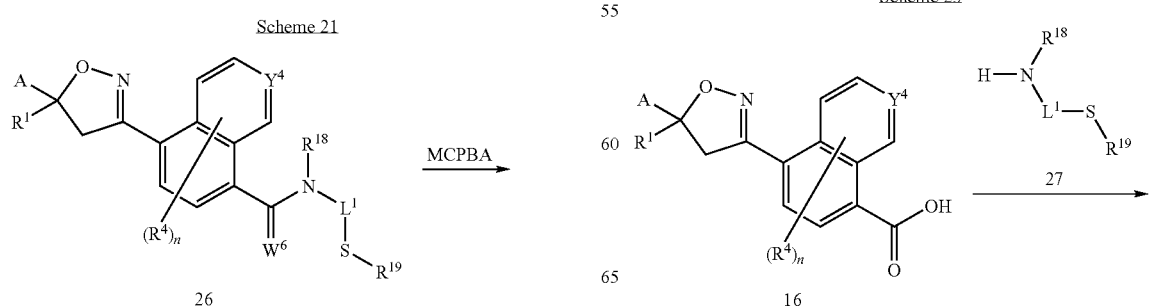

-continued

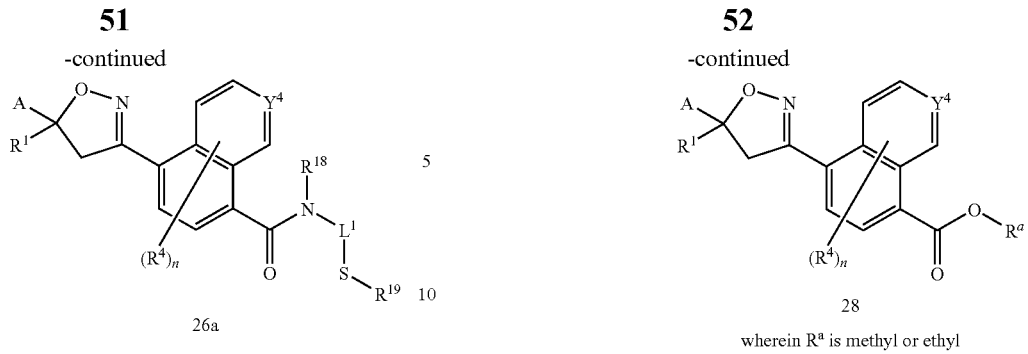

26a

As shown in Scheme 23, compounds of Formula 26a (Formula 26 wherein $W^6$ is O) can be prepared by coupling the acids of Formula 16 with appropriately substituted amino compounds of Formula 27. The method of Scheme 23 is conducted as described for Scheme 2 and is illustrated in Step A of Example 3.

Scheme 24

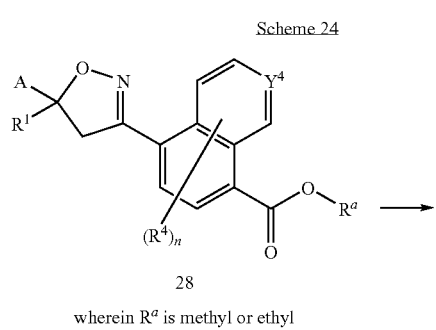

wherein $R^a$ is methyl or ethyl

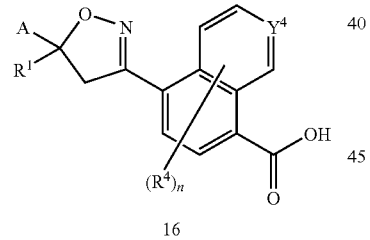

16

As shown in Scheme 24, carboxylic acids of Formula 16 can be prepared by hydrolysis of the corresponding esters of Formula 28, wherein $R^a$ is methyl or ethyl. The method of Scheme 24 is conducted as described for Scheme 8.

Scheme 25

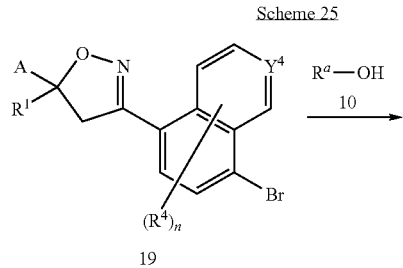

19

28 wherein $R^a$ is methyl or ethyl

As shown in Scheme 25, compounds of Formula 28 can be prepared by coupling of the corresponding bromides of Formula 19 with alcohols of Formula 10, for example, methanol or ethanol, with carbon monoxide in the presence of palladium catalysts. The method of Scheme 25 is conducted as described for Scheme 9.

Scheme 26

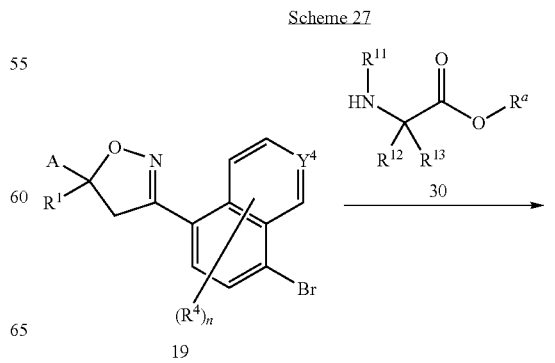

As shown in Scheme 26, carboxylic acids of Formula 20 can be prepared by hydrolysis of the corresponding esters of Formula 29. The method of Scheme 26 is conducted as described for Scheme 8 and is illustrated in Step B of Example 1.

Scheme 27

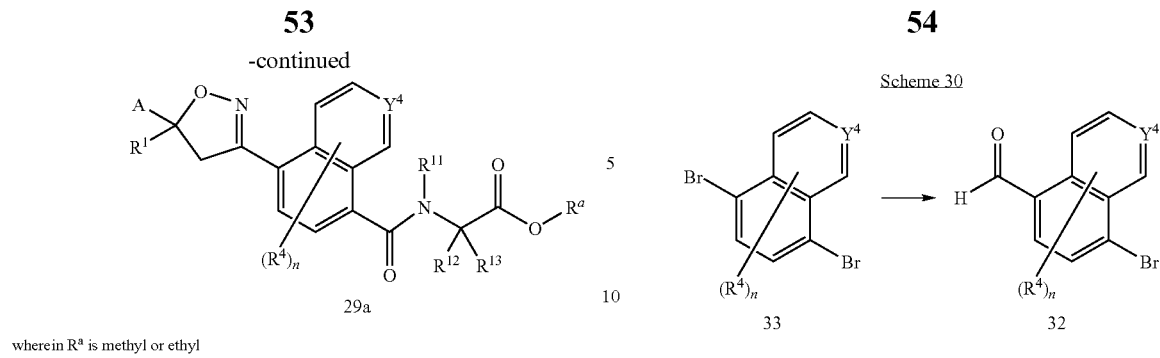

wherein R$^a$ is methyl or ethyl

As shown in Scheme 27, compounds of Formula 29a (Formula 29 wherein W$^4$ is O) can be prepared by coupling bromides of Formula 19 with appropriately substituted amino compounds of Formula 30 (or corresponding salts) in the presence of carbon monoxide. The method of Scheme 27 is conducted as described for Scheme 3 and is illustrated in Step A of Example 1.

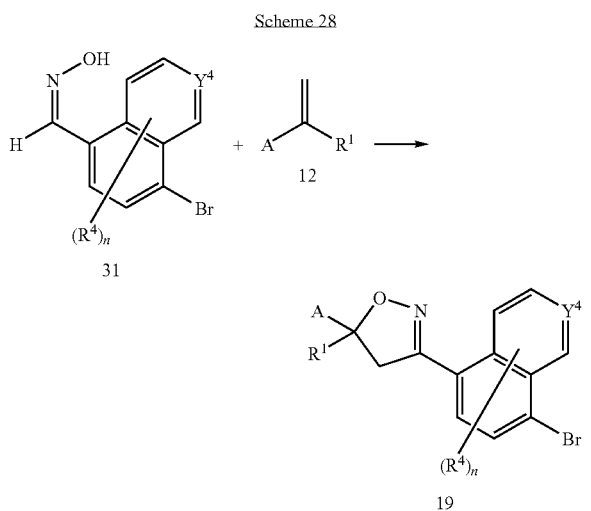

As shown in Scheme 28, compounds of Formula 19 can be prepared by the 1,3-dipolar cyclization of styrenes of Formula 12 with oximes of Formula 31. The method of Scheme 28 is conducted as described for Scheme 10.

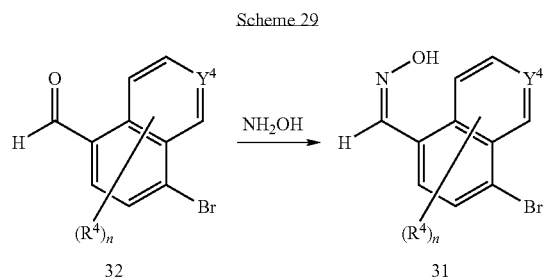

As shown in Scheme 29, oximes of Formula 31 can be prepared by reaction of the corresponding aldehydes of Formula 32 with hydroxylamine. The method of Scheme 29 is conducted as described for Scheme 11.

As shown in Scheme 30, aldehydes of Formula 32 can be prepared by treating compounds of Formula 33 with n-BuLi at −78° C. and reacting the derived lithiated intermediate with N,N-dimethylformamide. The bromo compounds of Formula 33 can be prepared by general methods known in literature, for example, see *Synthesis*, 2002, 83.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets and "br" means broad.

EXAMPLE 1

Preparation of 4-[5-(3,5-dichlorophenyl)-4,5-dihydro-5-(trifluoromethyl)-3-isoxazolyl]-N-[2-[2-methoxyethyl)amino]-2-oxoethyl]-1-naphthalenecarboxamide

Step A: N-[[4-[5-(3,5-dichlorophenyl)-4,5-dihydro-5-(trifluoromethyl)-3-isoxazolyl]-1-naphthalenyl]carbonyl]glycine methyl ester A mixture of 3-(4-bromo-1-naphthalenyl)-5-(3,5-dichlorophenyl)-4,5-dihydro-5-(trifluoromethyl)isoxazole (500 mg), [1,1'-bis(diphenylphosphino)ferrocene]-dichloropalladium(II) (PdCl$_2$(dppf)) (82 mg), glycine methyl ester hydrochloride (514 mg) and triethylamine (2.8 mL) in toluene (10 mL) in a vial was purged with carbon monoxide for 15 minutes. The reaction vial was maintained with carbon monoxide using a balloon. The reaction mixture was stirred overnight at 70° C. under carbon monoxide atmosphere. The mixture was cooled to room temperature, filtered through a short pad of Celite® diatomaceous filter aid and rinsed with small amount of ethyl acetate. The filtrate was concentrated, and the residue was purified by column chromatography on silica gel using hexanes/ethyl acetate (4:1 to 1:1) as eluent to afford the title product as a white solid (310 mg, 58% yield).

$^1$H NMR (CDCl$_3$) δ 8.75 (d, 1H), 8.28 (d, 1H), 7.45-7.60 (m, 7H), 7.36 (d, 1H), 6.78 (t, br., 1H), 4.26 (d, 2H), 4.21 (d, 1H), 3.87 (d, 1H), 3.80 (s, 3H).

Step B: N-[[4-[5-(3,5-dichlorophenyl)-4,5-dihydro-5-(trifluoromethyl)-3-isoxazolyl]-1-naphthalenyl]carbonyl]glycine To a stirred solution of N-[[4-[5-(3,5-dichlorophenyl)-4,5-dihydro-5-(trifluoromethyl)-3-isoxazolyl]-1-naphthalenyl]carbonyl]glycine methyl ester (i.e. the title product of Step A) (620 mg) in tetrahydrofuran (5 mL) was added an aqueous solution of lithium hydroxide (300 mg in 5 mL of water). After stirring at room temperature for 1 h, the reaction mixture was diluted with water and extracted with hexane. The aqueous layer was acidified with 6.0 N HCl to pH=2, causing a white precipitate to form. The aqueous mixture was extracted with ethyl acetate, washed with brine, dried with anhydrous sodium sulfate, and concentrated to afford the title compound as a white solid (600 mg, 99% yield).

$^1$H NMR (CD$_3$S(=O)CD$_3$) δ 9.02 (t, 1H), 8.81 (d, 1H), 8.37 (d, 1H), 7.92 (d, 1H), 7.83 (t, 1H), 7.65-7.74 (m, 5H), 4.58 (d, 1H), 4.54 (d, 1H), 4.02 (d, 2H).

Step C: 4-[5-(3,5-dichlorophenyl)-4,5-dihydro-5-(trifluoromethyl)-3-isoxazolyl]-N-[2-[2-methoxyethyl)amino]-2-oxoethyl]-1-naphthalenecarboxamide To a stirred solution of N-[[4-[5-(3,5-dichlorophenyl)-4,5-dihydro-5-(trifluoromethyl)-3-isoxazolyl]-1-naphthalenyl]carbonyl]glycine (i.e. the title product of Step B) (100 mg) and pyridine (0.019 mL) in dichloromethane (3 mL) was added trimethylacetyl chloride (0.029 mL). The reaction mixture was stirred at room temperature for 2 h, and then 2-methoxyethylamine (0.11 mL) and triethylamine (0.68 mL, 5.0 mmol) were added. The reaction mixture was stirred at room temperature overnight, quenched with water, extracted with dichloromethane, washed with brine, dried with anhydrous sodium sulfate and concentrated. The residue was purified by column chromatography on silica gel using hexanes/ethyl acetate (3:2 to 1:4) as eluent to afford the title compound, a compound of the present invention, as a white solid (71 mg, 0.13 mmol, 65% yield).

$^1$H NMR (CDCl$_3$) δ 8.82 (d, 1H), 8.32 (d, 1H), 7.45-7.66 (m, 7H), 7.00 (br s, 1H), 6.45 (br s, 1H), 4.25 (d, 1H), 4.21 (d, 2H), 3.89 (d, 1H), 3.49 (m, 4H), 3.36 (s, 3H).

EXAMPLE 2

Preparation of N-[2-[(cyclopropylmethyl)amino]-2-oxoethyl]-4-[5-(3,5-dichlorophenyl)-4,5-dihydro-5-(trifluoromethyl)-3-isoxazolyl]-1-naphthalenecarboxamide

Step A: 2-[4-[5-(3,5-dichlorophenyl)-4,5-dihydro-5-(trifluoromethyl)-3-isoxazolyl]-1-naphthalenyl]-5(4H)-oxazolone A mixture of N-[[4-[5-(3,5-dichlorophenyl)-4,5-dihydro-5-(trifluoromethyl)-3-isoxazolyl]-1-naphthalenyl]carbonyl]glycine (510 mg) and PS (polymer supported)-carbodiimide (1.69 g, 123 mmol/g) in dichloromethane (25 mL) was stirred at room temperature overnight. The reaction mixture was filtered through a short pad of Celite® diatomaceous filter aid and rinsed with dichloromethane. The filtrate was concentrated to provide the title compound (400 mg, 81% yield) as a pale yellow solid used directly for next step.

$^1$H NMR (CDCl$_3$) δ 9.33 (m, 1H), 8.87 (m, 1H), 8.15 (d, 1H), 7.73 (m, 2H), 7.59 (d, 1H), 7.57 (d, 2H), 7.46 (dd, 1H), 4.62 (s, 2H), 4.29 (d, 1H), 3.93 (d, 1H).

Step B: N-[2-[(cyclopropylmethyl)amino]-2-oxoethyl]-4-[5-(3,5-dichlorophenyl)-4,5-dihydro-5-(trifluoromethyl)-3-isoxazolyl]-1-naphthalenecarboxamide A mixture of 2-[4-[5-(3,5-dichlorophenyl)-4,5-dihydro-5-(trifluoromethyl)-3-isoxazolyl]-1-naphthalenyl]-5(4H)-oxazolone (i.e. the title product of Step A) (50 mg) and (aminomethyl)cyclopropane (0.1 mL) in N,N-dimethylformamide (1 mL) was irradiated with microwave radiation to maintain a temperature around 150° C. for 30 minutes. The reaction mixture was diluted with water and extracted with ethyl acetate. The organic layer was washed with brine, dried with anhydrous sodium sulfate, and concentrated. The residue was purified by column chromatography on silica gel using hexanes/ethyl acetate (3:2 to 3:7) as eluent to afford the title compound, a compound of the present invention, as a pale yellow solid (47 mg, 82% yield).

$^1$H NMR (CDCl$_3$) δ 8.83 (d, 1H), 8.31 (d, 1H), 7.45-7.67 (m, 7H), 7.10 (br s, 1H), 6.40 (br s, 1H), 4.25 (d, 1H), 4.21 (d, 2H), 3.89 (d, 1H), 3.17 (dd, 2H), 0.97 (m, 1H), 0.52 (m, 2H), 0.21 (m, 2H).

EXAMPLE 3

Preparation of 4-[5-(3,5-dichlorophenyl)-4,5-dihydro-5-(trifluoromethyl)-3-isoxazolyl]-N-[2-[S-methyl-N-(2,2,2-trifluoroacetyl)sulfonimidoyl]ethyl]-1-naphthalenecarboxamide

Step A: 4-[5-(3,5-dichlorophenyl)-4,5-dihydro-5-(trifluoromethyl)-3-isoxazol)]-N-[2-(methylthio)ethyl]-1-naphthalenecarboxamide To a stirred suspension of 4-[5-(3,5-dichlorophenyl)-4,5-dihydro-5-(trifluoromethyl)-3-isoxazolyl]-1-naphthalenecarboxylic acid (620 mg) in dichloromethane (20 mL) at room temperature was added oxalyl chloride (0.24 mL), followed by two drops of N,N-dimethylformamide. The reaction mixture was stirred at room temperature for 1.5 h and then concentrated under vacuum. The residue was dissolved in dichloromethane (10 mL) and added to a stirred solution of 2-(methylthio)ethylamine (0.13 mL) and Et$_3$N (0.38 mL) in dichloromethane (10 mL) at room temperature. The resulting reaction mixture was stirred at room temperature overnight. The reaction mixture was quenched with water and extracted with dichloromethane, washed with brine, dried with sodium sulfate and concentrated, and the residue was purified by column chromatography on silica gel using hexanes/ethyl acetate (7:3 to 1:1) as eluent to afford the title compound as a white solid (510 mg, 71% yield).

$^1$H NMR (CDCl$_3$) δ 8.78 (d, 1H), 8.27 (d, 1H), 7.56-7.64 (m, 4H), 7.49 (d, 1H), 7.46 (dd, 1H), 7.40 (d, 1H), 6.57 (br t, 1H), 4.23 (d, 1H), 3.88 (d, 1H), 3.71 (q, 2H), 2.79 (t, 2H), 2.15 (s, 3H).

Step B: 4-[5-(3,5-dichlorophenyl)-4,5-dihydro-5-(trifluoromethyl)-3-isoxazolyl]-N-[2-(methylsulfinyl)ethyl]-1-naphthalenecarboxamide To a stirred solution of 4-[5-(3,5-dichlorophenyl)-4,5-dihydro-5-(trifluoromethyl)-3-isoxazolyl]-N-[2-(methylthio)ethyl]-1-naphthalenecarboxamide (i.e. the title product of Step A) (100 mg) in dichloromethane (10 mL) was added MCPBA (47 mg, 70%) at −78° C. The reaction mixture was stirred at −78 to −70° C. for 2.5 h, then quenched with saturated sodium bicarbonate, extracted with dichloromethane, washed with brine, dried with sodium sulfate, and concentrated to afford the title compound as a white solid (102 mg, 99% yield).

$^1$H NMR (CDCl$_3$) δ 8.78 (d, 1H), 8.29 (d, 1H), 7.42-7.64 (m, 7H), 7.37 (br t, 1H), 4.23 (d, 1H), 4.00 (q, 2H), 3.88 (d, 1H), 3.18 (dt, 1H), 2.89 (dt, 1H), 2.62 (s, 3H).

Step C: 4-[5-(3,5-dichlorophenyl-4,5-dihydro-5-(trifluoromethyl)-3-isoxazolyl]-N-[2-(S-methyl-N-(2,2,2-trifluoroacetyl)sulfonimidoyl)ethyl]-1-naphthalenecarboxamide To a stirred suspension of 4-[5-(3,5-dichlorophenyl)-4,5-dihydro-5-(trifluoromethyl)-3-isoxazolyl]-N-[2-(methylsulfinyl)ethyl]-1-naphthalenecarboxamide (i.e. the title product of Step B) (180 mg), 2,2,2-trifluoroacetamide (75 mg), MgO (53 mg), and Rh$_2$(OAc)$_4$ (4 mg) in dichloromethane (4 mL) was added PhI(OAc)$_2$ (160 mg) at room temperature. The resulting mixture was stirred for 5 h at room temperature, then filtered through a short pad of Celite® diatomaceous filter aid, and rinsed with ethyl acetate. The filtrate was concentrated, and the residue was purified by column chromatography on silica gel using hexanes/ethyl acetate (3:7 to 1:9) as eluent to afford the title compound, a compound of the present invention, as yellow oil (100 mg, 46% yield).

$^1$H NMR (CDCl$_3$) δ 8.80 (d, 1H), 8.26 (d, 1H), 7.42-7.65 (m, 7H), 6.99 (br t, 1H), 4.24 (d, 1H), 4.11 (m, 2H), 3.89 (d, 1H), 3.82 (m, 2H), 3.48 (s, 3H).

EXAMPLE 4

Preparation of 4-[5-(3,5-dichlorophenyl)-4,5-dihydro-5-(trifluoromethyl)-3-isoxazolyl]-N-[2-(S-methylsulfonimidoyl)ethyl]-1-naphthalene carboxamide To a stirred solution of 4-[5-(3,5-dichlorophenyl)-4,5-dihydro-5-(trifluoromethyl)-3-isoxazolyl]-N-[2-[S-methyl-N-(2,2,2-trifluoroacetyl)sulfonimidoyl]ethyl]-1-naphthalenecarboxamide (i.e. the title compound of Example 3) (60 mg) in methanol (4 mL) was added potassium carbonate (230 mg) at room temperature. After stirring for 30 minutes at room temperature, the reaction mixture was filtered through a short pad of silical gel and rinsed with ethyl acetate. After concentration, the residue was purified by column chromatography on silica gel using dichloromethane/methanol (98:2 to 92:8) as eluent to provide the title product, a compound of the present invention, as a white solid (39 mg, 76% yield).

$^1$H NMR (CD$_3$COCD$_3$) δ 8.91 (d, 1H), 8.43 (d, 1H), 8.18 (br s, 1H), 7.87 (d, 1H), 7.63-7.76 (m, 6H), 4.61 (d, 1H), 4.47 (d, 1H), 3.99 (m, 2H), 3.50 (m, 2H), 3.35 (br s, 1H), 3.07 (s, 3H).

EXAMPLE 5

Preparation of 4-[4,5-dihydro-5-(3,4,5-trichlorophenyl)-5-(trifluoromethyl)-3-isoxazolyl]-N-[2-(S-methylsulfinimidoyl)ethyl]-1-naphthalenecarboxamide Step A: 4-[4,5-dihydro-5-(3,4,5-trichlorophenyl)-5-(trifluoromethyl)-3-isoxazolyl]-N-[2-[S-methyl-N-(2,2,2-trifluoroacetyl)sulfinimidoyl]ethyl]-1-naphthalenecarboxamide To a stirred suspension of 4-[4,5-dihydro-5-(3,4,5-trichlorophenyl)-5-(trifluoromethyl)-3-isoxazolyl]-N-[2-(methylthio)ethyl]-1-naphthalenecarboxamide (prepared analogously as described for the compound of Example 3, Step A) (200 mg), 2,2,2-trifluoroacetamide (80 mg), MgO (57 mg), and Rh$_2$(OAc)$_4$ (4 mg) in dichloromethane (4 mL) was added PhI(OAc)$_2$ (172 mg) at room temperature. The resulting mixture was stirred overnight at room temperature, then filtered through a short pad of Celite® diatomaceous filter aid, and rinsed with ethyl acetate. The filtrate was concentrated, and the residue was purified by column chromatography on silica gel using hexanes/ethyl acetates (1:1 to 1:4) as eluent to afford the title compound as a semisolid (70 mg, 30% yield).

$^1$H NMR (CDCl$_3$) δ 8.77 (d, 1H), 8.31 (d, 1H), 7.70 (s, 2H), 7.54-7.66 (m, 4H), 7.44 (d, 1H), 4.25 (d, 1H), 4.16 (m, 1H), 3.88 (d, 1H), 3.58 (m, 2H), 3.22 (m, 1H), 2.87 (s, 3H).

Step B: 4-[4,5-dihydro-5-(3,4,5-trichlorophenyl)-5-(trifluoromethyl)-3-isoxazolyl]-N-[2-(S-methylsulfinimidoyl)ethyl]-1-naphthalenecarboxamide To a stirred solution of 4-[4,5-dihydro-5-(3,4,5-trichlorophenyl)-5-(trifluoromethyl)-3-isoxazolyl]-N-[2-[S-methyl-N-(2,2,2-trifluoroacetyl)sulfinimidoyl]ethyl]-1-naphthalene-carboxamide (70 mg) (i.e. the title compound of Step A) in methanol (2 mL) was added potassium carbonate (300 mg) at room temperature. After stirring overnight at room temperature, the reaction mixture was filtered through a short pad of silica gel and rinsed with ethyl acetate. After concentration, the residue was purified by column chromatography on silica gel using dichloromethane/methanol (98:2 to 92:8) as eluent to afford the title compound, a compound of the present invention, as a semisolid (9 mg, 15% yield).

$^1$H NMR (CDCl$_3$) δ 8.81 (d, 1H), 8.35 (d, 1H), 7.61-7.70 (m, 5H), 7.49 (d, 1H), 7.11 (br t, 1H), 4.26 (d, 1H), 4.11 (m, 2H), 3.88 (d, 1H), 3.24 (m, 1H), 2.95 (m, 1H), 2.70 (s, 3H).

EXAMPLE 6

Preparation of 4-[5-(3,5-dichlorophenyl)-4,5-dihydro-5-(trifluoromethyl)-3-isoxazolyl]-N-(dimethyl-$\lambda^4$-sulfanylidene)-1-naphthalenecarboxamide To a stirred solution of dimethylsulfoxide (38 mg) in dichloromethane (1 mL) at −60° C. was added trifluoroacetic anhydride (105 mg). After the reaction mixture was stirred for 10 minutes at −60° C., a solution of 4-[5-(3,5-dichlorophenyl)-4,5-dihydro-5-(trifluoromethyl)-3-isoxazolyl]-1-naphthalenecarboxamide (75 mg, in 1.5 mL of dichloromethane and 0.4 mL of dimethylsulfoxide) was added. The reaction mixture was allowed to warm to −20° C. over 1 h, then quenched with water and extracted with dichloromethane. The combined organic extract was washed with aqueous 1.0 N of NaOH and brine, dried with anhydrous sodium sulfate and concentrated. The residue was purified by column chromatography on silica gel using dichloromethane/methanol (98:2 to 95:5) as eluent to afford the title product, a compound of the present invention, as semi-solid (70 mg, 82% yield).

$^1$H NMR (CDCl$_3$) δ 8.80 (m, 1H), 8.69 (m, 1H), 7.85 (d, 1H), 7.44-7.62 (m, 6H), 4.26 (d, 1H), 3.89 (d, 1H), 2.86 (s, 6H).

By the procedures described herein together with methods known in the art, the following compounds of Tables 1 to 52 can be prepared. The following abbreviations are used in the Tables which follow: Cmpd. means compound, n means normal, i means iso, c means cyclo, Me means methyl, Et means ethyl, Pr means propyl, i-Pr means isopropyl, Ph means phenyl, OMe means methoxy, SMe means methylthio, CN means cyano, Ph means phenyl, Py means pyridinyl, S(=O)Me means methylsulfinyl, and SO$_2$Me means methylsulfonyl. In the Tables the variable "R$^2$" represents one or a combination of substituents as defined.

In Table 49, compounds are specifically named by first indicating the relevant preceding Table number (i.e. from Tables 1-48) defining a Markush structure and then the line number for the preceding Table defining substituents attached to the Markush structure. Each such designation specifically identifies a unique compound of the present invention. For example, Compound I-1 is the compound of Formula 1, as defined by Table 1, Line 1 wherein A is phenyl, Q is Q-A-1, R$^2$ is 3-CF$_3$, R$^5$ is Et and R$^6$ is H. Similarly, Compound 17-4 is the compound of Formula 1, Table 17, Line 4 wherein A is phenyl, Q is Q-A-17, R$^2$ is 3-Cl, 5-Cl, R$^{19}$ is Et and R$^{20}$ is H.

TABLES 1-8

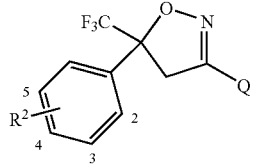

Q is:

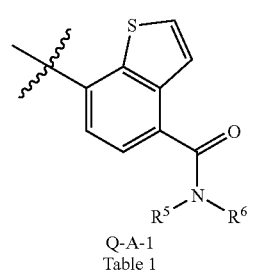

Q-A-1
Table 1

TABLES 1-8-continued

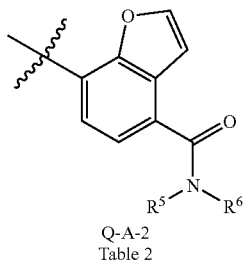

Q-A-2
Table 2

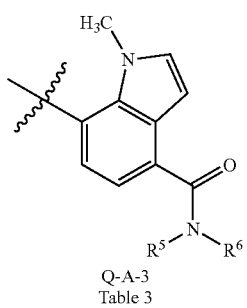

Q-A-3
Table 3

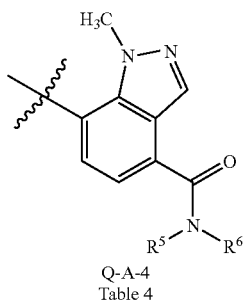

Q-A-4
Table 4

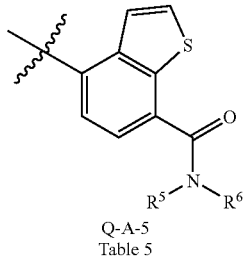

Q-A-5
Table 5

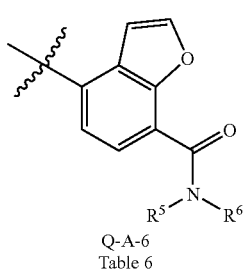

Q-A-6
Table 6

TABLES 1-8-continued

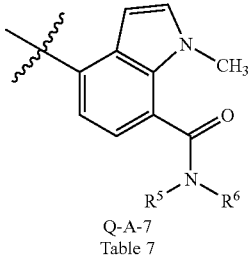

Q-A-7
Table 7

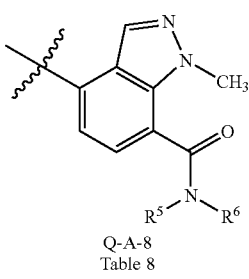

Q-A-8
Table 8

| Line | R⁵ | R⁶ |
|---|---|---|
| *wherein R² is 3-CF₃* | | |
| 1 | Et | H |
| 2 | CH₂-c-Py | H |
| 3 | CH₂-c-Pr | H |
| 4 | CH₂CF₃ | H |
| 5 | CH₂CH₂OMe | H |
| 6 | CH₂CH₂SMe | H |
| 7 | CH₂CH₂(S=O)Me | H |
| 8 | CH₂CH₂SO₂Me | H |
| 9 | CH₂C(=O)NHCH₃ | H |
| 10 | CH₂C(=O)NHCH₂CH₃ | H |
| 11 | CH₂C(=O)NH-c-Pr | H |
| 12 | CH₂C(=O)NHCH₂CF₃ | H |
| 13 | CH(CH₃)C(=O)NHCH₂CF₃ | H |
| 14 | CH₂C(=O)NH(CH₂)₂OMe | H |
| 15 | CH₂C(=O)NH(CH₂)₂SMe | H |
| *wherein R² is 3-Br, 5-Br* | | |
| 16 | Et | H |
| 17 | CH₂-2-Py | H |
| 18 | CH₂-c-Pr | H |
| 19 | CH₂CF₃ | H |
| 20 | CH₂CH₂OMe | H |
| 21 | CH₂CH₂SMe | H |
| 22 | CH₂CH₂(S=O)Me | H |
| 23 | CH₂CH₂SO₂Me | H |
| 24 | CH₂C(=O)NHCH₃ | H |
| 25 | CH₂C(=O)NHCH₂CH₃ | H |
| 26 | CH₂C(=O)NH-c-Pr | H |
| 27 | CH₂C(=O)NHCH₂CF₃ | H |
| 28 | CH(CH₃)C(=O)NHCH₂CF₃ | H |
| 29 | CH₂C(=O)NH(CH₂)₂OMe | H |
| 30 | CH₂C(=O)NH(CH₂)₂SMe | H |
| *wherein R² is 3-Cl, 4-F, 5-Cl* | | |
| 31 | Et | H |
| 32 | CH₂-2-Py | H |
| 33 | CH₂-c-Pr | H |
| 34 | CH₂CF₃ | H |
| 35 | CH₂CH₂OMe | H |
| 36 | CH₂CH₂SMe | H |
| 37 | CH₂CH₂(S=O)Me | H |
| 38 | CH₂CH₂SO₂Me | H |
| 39 | CH₂C(=O)NHCH₃ | H |
| 40 | CH₂C(=O)NHCH₂CH₃ | H |
| 41 | CH₂C(=O)NH-c-Pr | H |
| 42 | CH₂C(=O)NHCH₂CF₃ | H |
| 43 | CH(CH₃)C(=O)NHCH₂CF₃ | H |
| 44 | CH₂C(=O)NH(CH₂)₂OMe | H |
| 45 | CH₂C(=O)NH(CH₂)₂SMe | H |
| *wherein R² is 3-Cl, 5-Cl* | | |
| 46 | CH₂CF₃ | Me |
| 47 | CH₂-2-Py | Me |
| 48 | CH₂CH₂SMe | Me |
| 49 | CH₂CH₂S(=O)Me | Me |
| 50 | CH₂CH₂SO₂Me | Me |
| 51 | CH₂C(=O)NHCH₂CF₃ | Me |
| 52 | CH(CH₃)C(=O)NHCH₂CF₃ | Me |
| 53 | CH₂CF₃ | C(=O)Me |
| 54 | CH₂-2-Py | C(=O)Me |
| 55 | CH₂CH₂SMe | C(=O)Me |
| 56 | CH₂CH₂S(=O)Me | C(=O)Me |
| 57 | CH₂CH₂SO₂Me | C(=O)Me |
| 58 | CH₂C(=O)NHCH₂CF₃ | C(=O)Me |
| 59 | CH(CH₃)C(=O)NHCH₂CF₃ | C(=O)Me |
| 60 | CH₂CF₃ | CO₂Me |
| 61 | CH₂-2-Py | CO₂Me |
| 62 | CH₂CH₂SMe | CO₂Me |
| 63 | CH₂CH₂S(=O)Me | CO₂Me |
| 64 | CH₂CH₂SO₂Me | CO₂Me |
| 65 | CH₂C(=O)NHCH₂CF₃ | CO₂Me |
| 66 | CH(CH₃)C(=O)NHCH₂CF₃ | CO₂Me |
| *wherein R² is 3-Cl* | | |
| 67 | CH₂CF₃ | H |
| 68 | CH₂-2-Py | H |
| 69 | CH₂CH₂SMe | H |
| 70 | CH₂-c-Pr | H |
| 71 | CH₂C(=O)NHCH₂CF₃ | H |
| *wherein R² is 3-Br, 5-OCF₃* | | |
| 72 | CH₂CF₃ | H |
| 73 | CH₂-2-Py | H |
| 74 | CH₂CH₂SMe | H |
| 75 | CH₂-c-Pr | H |
| 76 | CH₂C(=O)NHCH₂CF₃ | H |
| *wherein R² is 3-Cl, 5-Br* | | |
| 77 | CH₂CF₃ | H |
| 78 | CH₂-2-Py | H |
| 79 | CH₂CH₂SMe | H |
| 80 | CH₂-c-Pr | H |
| 81 | CH₂C(=O)NHCH₂CF₃ | H |
| *wherein R² is 3-CF₃, 5-Cl* | | |
| 82 | CH₂CF₃ | H |
| 83 | CH₂-2-Py | H |
| 84 | CH₂CH₂SMe | H |
| 85 | CH₂-c-Pr | H |
| 86 | CH₂C(=O)NHCH₂CF₃ | H |
| *wherein R² is 3-Cl, 4-CN, 5-Cl* | | |
| 87 | CH₂CF₃ | H |
| 88 | CH₂-2-Py | H |
| 89 | CH₂CH₂SMe | H |
| 91 | CH₂-c-Pr | H |
| 92 | CH₂C(=O)NHCH₂CF₃ | H |
| *wherein R² is 3-Cl, 5-Cl* | | |
| 93 | Et | H |
| 94 | CH₂-2-Py | H |
| 95 | CH₂-c-Pr | H |
| 96 | CH₂CF₃ | H |
| 97 | CH₂CH₂OMe | H |
| 98 | CH₂CH₂SMe | H |
| 99 | CH₂CH₂(S=O)Me | H |
| 100 | CH₂CH₂SO₂Me | H |
| 101 | CH₂C(=O)NHCH₃ | H |
| 102 | CH₂C(=O)NHCH₂CH₃ | H |
| 103 | CH₂C(=O)NH-c-Pr | H |
| 104 | CH₂C(=O)NHCH₂CF₃ | H |
| 105 | CH(CH₃)C(=O)NHCH₂CF₃ | H |
| 106 | CH₂C(=O)NH(CH₂)₂OMe | H |
| 107 | CH₂C(=O)NH(CH₂)₂SMe | H |
| *wherein R² is 3-Cl, 4-Cl, 5-Cl* | | |
| 108 | Et | H |
| 109 | CH₂-2-Py | H |
| 110 | CH₂-c-Pr | H |

TABLES 1-8-continued

| | | |
|---|---|---|
| 111 | $CH_2CF_3$ | H |
| 112 | $CH_2CH_2OMe$ | H |
| 113 | $CH_2CH_2SMe$ | H |
| 114 | $CH_2CH_2S(\!=\!O)Me$ | H |
| 115 | $CH_2CH_2SO_2Me$ | H |
| 116 | $CH_2C(\!=\!O)NHCH_3$ | H |
| 117 | $CH_2C(\!=\!O)NHCH_2CH_3$ | H |
| 118 | $CH_2C(\!=\!O)NH\text{-}c\text{-}Pr$ | H |
| 119 | $CH_2C(\!=\!O)NHCH_2CF_3$ | H |
| 120 | $CH(CH_3)C(\!=\!O)NHCH_2CF_3$ | H |
| 121 | $CH_2C(\!=\!O)NH(CH_2)_2OMe$ | H |
| 122 | $CH_2C(\!=\!O)NH(CH_2)_2SMe$ | H |
| wherein $R^2$ is 3-$CF_3$, 5-$CF_3$ | | |
| 123 | Et | H |
| 124 | $CH_2\text{-}2\text{-}Py$ | H |
| 125 | $CH_2\text{-}c\text{-}Pr$ | H |
| 126 | $CH_2CF_3$ | H |
| 127 | $CH_2CH_2OMe$ | H |
| 128 | $CH_2CH_2SMe$ | H |
| 129 | $CH_2CH_2S(\!=\!O)Me$ | H |
| 130 | $CH_2CH_2SO_2Me$ | H |
| 131 | $CH_2C(\!=\!O)NHCH_3$ | H |
| 132 | $CH_2C(\!=\!O)NHCH_2CH_3$ | H |
| 133 | $CH_2C(\!=\!O)NH\text{-}c\text{-}Pr$ | H |
| 134 | $CH_2C(\!=\!O)NHCH_2CF_3$ | H |
| 135 | $CH(CH_3)C(\!=\!O)NHCH_2CF_3$ | H |
| 136 | $CH_2C(\!=\!O)NH(CH_2)_2OMe$ | H |
| 137 | $CH_2C(\!=\!O)NH(CH_2)_2SMe$ | H |
| wherein $R^2$ is 3-Br, 5-Br | | |
| 138 | $CH_2CF_3$ | Me |
| 139 | $CH_2\text{-}2\text{-}Py$ | Me |
| 140 | $CH_2CH_2SMe$ | Me |
| 141 | $CH_2CH_2S(\!=\!O)Me$ | Me |
| 142 | $CH_2CH_2SO_2Me$ | Me |
| 143 | $CH_2C(\!=\!O)NHCH_2CF_3$ | Me |
| 144 | $CH(CH_3)C(\!=\!O)NHCH_2CF_3$ | Me |
| 145 | $CH_2CF_3$ | $C(\!=\!O)Me$ |
| 146 | $CH_2\text{-}2\text{-}Py$ | $C(\!=\!O)Me$ |
| 147 | $CH_2CH_2SMe$ | $C(\!=\!O)Me$ |
| 148 | $CH_2CH_2S(\!=\!O)Me$ | $C(\!=\!O)Me$ |
| 149 | $CH_2CH_2SO_2Me$ | $C(\!=\!O)Me$ |
| 150 | $CH_2C(\!=\!O)NHCH_2CF_3$ | $C(\!=\!O)Me$ |
| 151 | $CH(CH_3)C(\!=\!O)NHCH_2CF_3$ | $C(\!=\!O)Me$ |
| 152 | $CH_2CF_3$ | $CO_2Me$ |
| 153 | $CH_2\text{-}2\text{-}Py$ | $CO_2Me$ |
| 154 | $CH_2CH_2SMe$ | $CO_2Me$ |
| 155 | $CH_2CH_2S(\!=\!O)Me$ | $CO_2Me$ |
| 156 | $CH_2CH_2SO_2Me$ | $CO_2Me$ |
| 157 | $CH_2C(\!=\!O)NHCH_2CF_3$ | $CO_2Me$ |
| 158 | $CH(CH_3)C(\!=\!O)NHCH_2CF_3$ | $CO_2Me$ |
| wherein $R^2$ is 3-Br | | |
| 159 | $CH_2CF_3$ | H |
| 160 | $CH_2\text{-}2\text{-}Py$ | H |
| 162 | $CH_2CH_2SMe$ | H |
| 163 | $CH_2\text{-}c\text{-}Pr$ | H |
| 164 | $CH_2C(\!=\!O)NHCH_2CF_3$ | H |
| wherein $R^2$ is 3-$CF_3$, 5-$CF_3$ | | |
| 165 | $CH_2CF_3$ | H |
| 166 | $CH_2\text{-}2\text{-}Py$ | H |
| 167 | $CH_2CH_2SMe$ | H |
| 168 | $CH_2\text{-}c\text{-}Pr$ | H |
| 169 | $CH_2C(\!=\!O)NHCH_2CF_3$ | H |
| wherein $R^2$ is 3-$CF_3$, 5-F | | |
| 170 | $CH_2CF_3$ | H |
| 171 | $CH_2\text{-}2\text{-}Py$ | H |
| 172 | $CH_2CH_2SMe$ | H |
| 173 | $CH_2\text{-}c\text{-}Pr$ | H |
| 174 | $CH_2C(\!=\!O)NHCH_2CF_3$ | H |
| wherein $R^2$ is 3-$CF_3$, 5-Br | | |
| 175 | $CH_2CF_3$ | H |
| 176 | $CH_2\text{-}2\text{-}Py$ | H |
| 177 | $CH_2CH_2SMe$ | H |
| 178 | $CH_2\text{-}c\text{-}Pr$ | H |
| 179 | $CH_2C(\!=\!O)NHCH_2CF_3$ | H |

TABLES 1-8-continued

| | | |
|---|---|---|
| wherein $R^2$ is 3-Cl, 4-Me, 5-Cl | | |
| 180 | $CH_2CF_3$ | H |
| 181 | $CH_2\text{-}2\text{-}Py$ | H |
| 182 | $CH_2CH_2SMe$ | H |
| 183 | $CH_2\text{-}c\text{-}Pr$ | H |
| 184 | $CH_2C(\!=\!O)NHCH_2CF_3$ | H |

TABLES 9-16

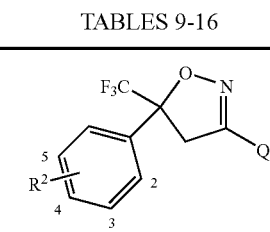

Q is:

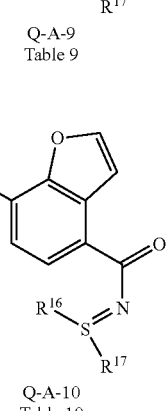

Q-A-9
Table 9

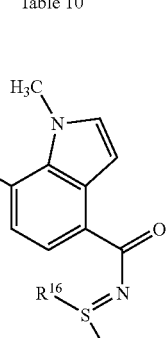

Q-A-10
Table 10

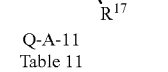

Q-A-11
Table 11

TABLES 9-16-continued

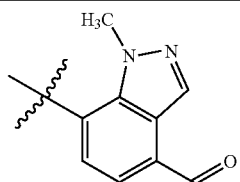

Q-A-12
Table 12

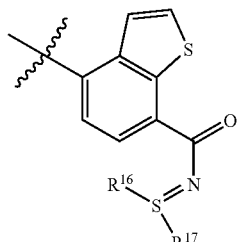

Q-A-13
Table 13

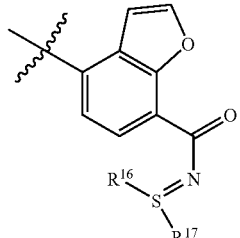

Q-A-14
Table 14

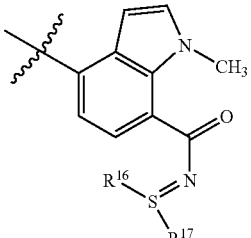

Q-A-14
Table 15

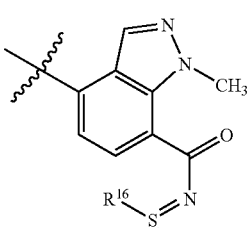

Q-A-16
Table 16

| Line | R² | R¹⁶ | R¹⁷ |
|---|---|---|---|
| 1 | 3-Cl, 5-Cl | Me | Me |
| 2 | 3-Cl, 5-Cl | Et | Me |
| 3 | 3-Cl, 5-Cl | n-Pr | Me |
| 4 | 3-Cl, 5-Cl | Et | Et |
| 5 | 3-Cl, 5-Cl | i-Pr | i-Pr |
| 6 | 3-Br, 5-Br | Me | Me |
| 7 | 3-Br, 5-Br | Et | Me |
| 8 | 3-Br, 5-Br | n-Pr | Me |
| 9 | 3-Br, 5-Br | Et | Et |
| 10 | 3-Br, 5-Br | i-Pr | i-Pr |
| 11 | 3-Cl, 4-Cl, 5-Cl | Me | Me |
| 12 | 3-Cl, 4-Cl, 5-Cl | Et | Me |
| 13 | 3-Cl, 4-Cl, 5-Cl | n-Pr | Me |
| 14 | 3-Cl, 4-Cl, 5-Cl | Et | Et |
| 15 | 3-Cl, 4-Cl, 5-Cl | i-Pr | i-Pr |
| 16 | 3-Cl, 4-F, 5-Cl | Me | Me |
| 17 | 3-Cl, 4-F, 5-Cl | Et | Me |
| 18 | 3-Cl, 4-F, 5-Cl | n-Pr | Me |
| 19 | 3-Cl, 4-F, 5-Cl | Et | Et |
| 20 | 3-Cl, 4-F, 5-Cl | i-Pr | i-Pr |
| 21 | 3-Cl | Me | Me |
| 22 | 3-Cl | Et | Me |
| 23 | 3-Cl | n-Pr | Me |
| 24 | 3-Cl | Et | Et |
| 25 | 3-Cl | i-Pr | i-Pr |
| 26 | 3-Br | Me | Me |
| 27 | 3-Br | Et | Me |
| 28 | 3-Br | n-Pr | Me |
| 29 | 3-Br | Et | Et |
| 30 | 3-Br | i-Pr | i-Pr |
| 31 | 3-CF₃, 5-CF₃ | Me | Me |
| 32 | 3-CF₃, 5-CF₃ | Et | Me |
| 33 | 3-CF₃, 5-CF₃ | n-Pr | Me |
| 34 | 3-CF₃, 5-CF₃ | Et | Et |
| 35 | 3-CF₃, 5-CF₃ | i-Pr | i-Pr |
| 36 | 3-CF₃, 5-Cl | Me | Me |
| 37 | 3-CF₃, 5-Cl | Et | Me |
| 38 | 3-CF₃, 5-Cl | n-Pr | Me |
| 39 | 3-CF₃, 5-Cl | Et | Et |
| 40 | 3-CF₃, 5-Cl | i-Pr | i-Pr |
| 41 | 3-CF₃, 5-Br | Me | Me |
| 42 | 3-CF₃, 5-Br | Et | Me |
| 43 | 3-CF₃, 5-Br | n-Pr | Me |
| 44 | 3-CF₃, 5-Br | Et | Et |
| 45 | 3-CF₃, 5-Br | i-Pr | i-Pr |
| 46 | 3-Cl, 4-CN, 5-Cl | Me | Me |
| 47 | 3-Cl, 4-CN, 5-Cl | Et | Me |
| 48 | 3-Cl, 4-CN, 5-Cl | n-Pr | Me |
| 49 | 3-Cl, 4-CN, 5-Cl | Et | Et |
| 50 | 3-Cl, 4-CN, 5-Cl | i-Pr | i-Pr |
| 51 | 3-Cl, 4-Me, 5-Cl | Me | Me |
| 52 | 3-Cl, 4-Me, 5-Cl | Et | Me |
| 53 | 3-Cl, 4-Me, 5-Cl | n-Pr | Me |
| 54 | 3-Cl, 4-Me, 5-Cl | Et | Et |
| 55 | 3-Cl, 4-Me, 5-Cl | i-Pr | i-Pr |
| 56 | 3-CF₃ | Me | H |
| 57 | 3-CF₃ | Me | C(=O)CF₃ |
| 58 | 3-CF₃ | Me | CN |
| 59 | 3-CF₃ | Et | H |
| 60 | 3-CF₃ | Et | C(=O)CF₃ |

TABLES 17-24
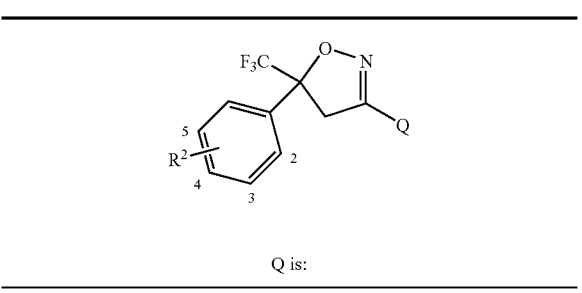
Q is:
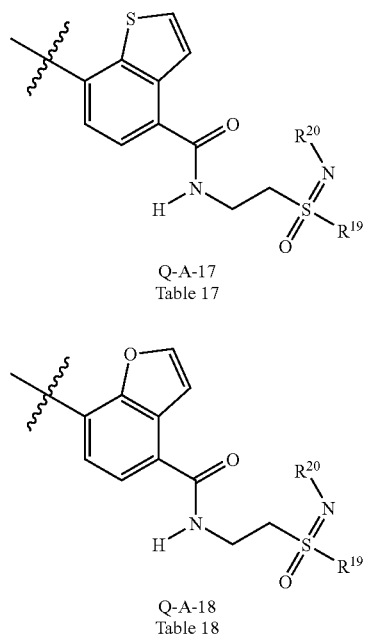
Q-A-17
Table 17
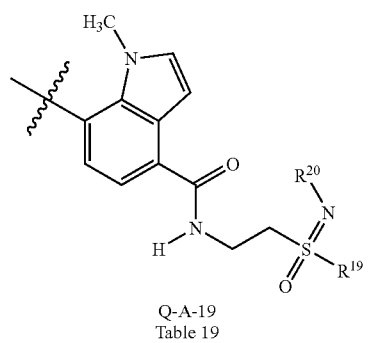
Q-A-18
Table 18
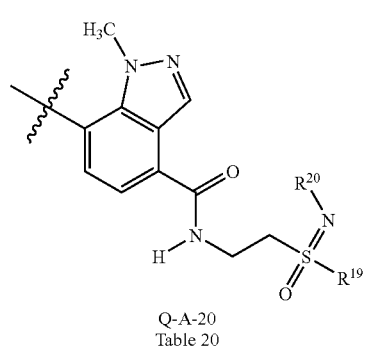
Q-A-19
Table 19
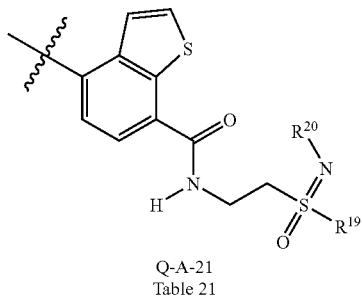
Q-A-20
Table 20
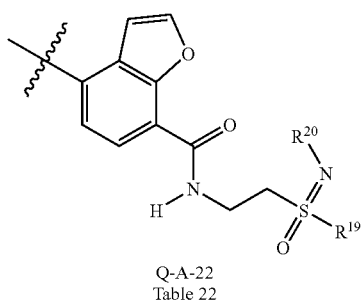
Q-A-21
Table 21
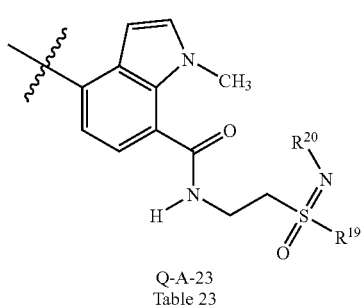
Q-A-22
Table 22
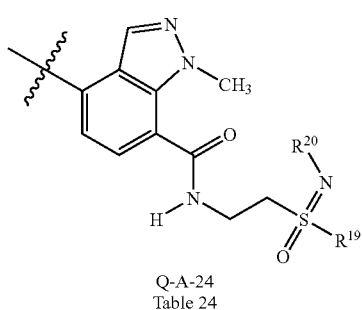
Q-A-23
Table 23
Q-A-24
Table 24
| Line | R² | R¹⁹ | R²⁰ |
|------|------|-----|---------|
| 1 | 3-Cl, 5-Cl | Me | H |
| 2 | 3-Cl, 5-Cl | Me | C(=O)CF₃ |
| 3 | 3-Cl, 5-Cl | Me | CN |
| 4 | 3-Cl, 5-Cl | Et | H |
| 5 | 3-Cl, 5-Cl | Et | C(=O)CF₃ |
| 6 | 3-Br, 5-Br | Me | H |
| 7 | 3-Br, 5-Br | Me | C(=O)CF₃ |
| 8 | 3-Br, 5-Br | Me | CN |
| 9 | 3-Br, 5-Br | Et | H |
| 10 | 3-Br, 5-Br | Et | C(=O)CF₃ |
| 11 | 3-Cl, 4-Cl, 5-Cl | Me | H |
| 12 | 3-Cl, 4-Cl, 5-Cl | Me | C(=O)CF₃ |
| 13 | 3-Cl, 4-Cl, 5-Cl | Me | CN |
| 14 | 3-Cl, 4-Cl, 5-Cl | Et | H |
| 15 | 3-Cl, 4-Cl, 5-Cl | Et | C(=O)CF₃ |
| 16 | 3-Cl, 4-F, 5-Cl | Me | H |
| 17 | 3-Cl, 4-F, 5-Cl | Me | C(=O)CF₃ |
| 18 | 3-Cl, 4-F, 5-Cl | Me | CN |
| 19 | 3-Cl, 4-F, 5-Cl | Et | H |

TABLES 17-24-continued

| | | | |
|---|---|---|---|
| 20 | 3-Cl, 4-F, 5-Cl | Et | C(=O)CF$_3$ |
| 21 | 3-Cl | Me | H |
| 22 | 3-Cl | Me | C(=O)CF$_3$ |
| 23 | 3-Cl | Me | CN |
| 24 | 3-Cl | Et | H |
| 25 | 3-Cl | Et | C(=O)CF$_3$ |
| 26 | 3-Br | Me | H |
| 27 | 3-Br | Me | C(=O)CF$_3$ |
| 28 | 3-Br | Me | CN |
| 29 | 3-Br | Et | H |
| 30 | 3-Br | Et | C(=O)CF$_3$ |
| 31 | 3-CF$_3$, 5-CF$_3$ | Me | H |
| 32 | 3-CF$_3$, 5-CF$_3$ | Me | C(=O)CF$_3$ |
| 33 | 3-CF$_3$, 5-CF$_3$ | Me | CN |
| 34 | 3-CF$_3$, 5-CF$_3$ | Et | H |
| 35 | 3-CF$_3$, 5-CF$_3$ | Et | C(=O)CF$_3$ |
| 36 | 3-CF$_3$, 5-Cl | Me | C(=O)CF$_3$ |
| 37 | 3-CF$_3$, 5-Cl | Me | CN |
| 38 | 3-CF$_3$, 5-Cl | Me | H |
| 39 | 3-CF$_3$, 5-Cl | Et | C(=O)CF$_3$ |
| 40 | 3-CF$_3$, 5-Cl | Et | i-Pr |
| 41 | 3-CF$_3$, 5-Br | Me | H |
| 42 | 3-CF$_3$, 5-Br | Me | C(=O)CF$_3$ |
| 43 | 3-CF$_3$, 5-Br | Me | CN |
| 44 | 3-CF$_3$, 5-Br | Et | H |
| 45 | 3-CF$_3$, 5-Br | Et | C(=O)CF$_3$ |
| 46 | 3-Cl, 4-CN, 5-Cl | Me | H |
| 47 | 3-Cl, 4-CN, 5-Cl | Me | C(=O)CF$_3$ |
| 48 | 3-Cl, 4-CN, 5-Cl | Me | CN |
| 49 | 3-Cl, 4-CN, 5-Cl | Et | H |
| 50 | 3-Cl, 4-CN, 5-Cl | Et | C(=O)CF$_3$ |
| 51 | 3-Cl, 4-Me, 5-Cl | Me | H |
| 52 | 3-Cl, 4-Me, 5-Cl | Me | C(=O)CF$_3$ |
| 53 | 3-Cl, 4-Me, 5-Cl | Me | CN |
| 54 | 3-Cl, 4-Me, 5-Cl | Et | H |
| 55 | 3-Cl, 4-Me, 5-Cl | Et | C(=O)CF$_3$ |
| 56 | 3-CF$_3$ | Me | H |
| 57 | 3-CF$_3$ | Me | C(=O)CF$_3$ |
| 58 | 3-CF$_3$ | Me | CN |
| 59 | 3-CF$_3$ | Et | H |
| 60 | 3-CF$_3$ | Et | C(=O)CF$_3$ |

TABLES 25-32

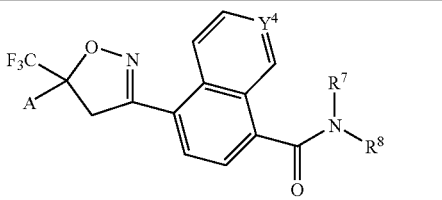

| Line | Y$^4$ | R$^7$ | R$^8$ |
|---|---|---|---|
| 1 | CH | H | CH$_2$CH$_2$OCH$_2$CF$_3$ |
| 2 | CH | H | CH$_2$CH$_2$OCH$_2$CH$_2$OPh |
| 3 | CH | H | CH$_2$CH$_2$OCH$_2$CH$_2$OMe |
| 4 | CH | H | CH$_2$CH$_2$OCH$_2$CH$_2$SH |
| 5 | CH | H | CH$_2$CH$_2$OCH$_2$CH$_2$SMe |
| 6 | CH | H | CH$_2$CH$_2$OCH$_2$CH$_2$S(=O)Me |
| 7 | CH | H | CH$_2$CH$_2$OCH$_2$CH$_2$SO$_2$Me |
| 8 | CH | H | CH$_2$CH$_2$OCH$_2$CH$_2$SO$_2$NHMe |
| 9 | CH | H | CH$_2$CH$_2$O(CH$_2$)2SO$_2$N(Me)$_2$ |
| 10 | CH | H | (CH$_2$)$_2$O(CH$_2$)$_2$OC(=O)NHMe |
| 11 | CH | H | (CH$_2$)$_2$O(CH$_2$)$_2$OC(=O)N(Me)$_2$ |
| 12 | CH | H | CH$_2$CH$_2$OCH$_2$CH$_2$OCO$_2$Me |
| 13 | CH | H | CH$_2$CH$_2$OCH$_2$OCO$_2$Me |
| 14 | CH | H | CH$_2$CH$_2$OCH$_2$C(=O)NHMe |
| 15 | CH | H | CH$_2$CH$_2$NHCH$_2$CF$_3$ |
| 16 | CH | H | CH$_2$CH$_2$N(Me)CH$_2$CF$_3$ |
| 17 | CH | H | CH$_2$CH$_2$N=CH-(2-Py) |
| 18 | CH | H | CH$_2$CH$_2$N=CH-(3-Py) |
| 19 | CH | H | CH$_2$CH$_2$NHC(=O)Me |
| 20 | CH | H | CH$_2$CH$_2$SCN |
| 21 | CH | H | CH$_2$Si(Me)$_3$ |

TABLES 25-32-continued

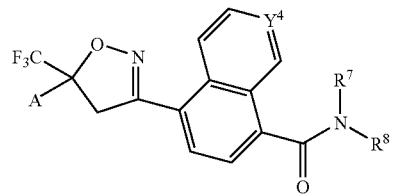

| Line | Y$^4$ | R$^7$ | R$^8$ |
|---|---|---|---|
| 22 | CH | H | CH$_2$Si(Me)$_2$Ph |
| 23 | CH | H | CH$_2$Si(Me)$_2$Et |
| 24 | CH | H | CH$_2$C(=O)OCH$_2$CH$_2$OMe |
| 25 | CH | H | CH$_2$C(=O)OCH$_2$CH$_2$OEt |
| 26 | CH | H | CH$_2$C(=S)SMe |
| 27 | CH | H | CH$_2$C(=S)OMe |
| 28 | CH | H | CH$_2$C(=O)SMe |
| 29 | CH | H | CH$_2$C(=S)Me |
| 30 | CH | H | CH$_2$C(=S)N(Me)$_2$ |
| 31 | CH | H | CH$_2$C(=S)NHMe |
| 32 | CH | H | CH$_2$C(=S)NHCH$_2$CF$_3$ |
| 33 | CH | H | CH$_2$P(=O)(OMe)$_2$ |
| 34 | CH | H | CH$_2$P(=S)(OMe)$_2$ |
| 35 | CH | Me | (CH$_2$)$_2$O(CH$_2$)$_2$SMe |
| 36 | CH | Me | (CH$_2$)$_2$O(CH$_2$)$_2$S(=O)Me |
| 37 | CH | Me | (CH$_2$)$_2$O(CH$_2$)$_2$SO$_2$Me |
| 38 | CH | C(=O)Me | (CH$_2$)$_2$O(CH$_2$)$_2$SMe |
| 39 | CH | C(=O)Me | (CH$_2$)$_2$O(CH$_2$)$_2$S(=O)Me |
| 40 | CH | C(=O)Me | (CH$_2$)$_2$O(CH$_2$)$_2$SO$_2$Me |
| 41 | N | H | CH$_2$CH$_2$OCH$_2$CF$_3$ |
| 42 | N | H | CH$_2$CH$_2$OCH$_2$CH$_2$OPh |
| 43 | N | H | CH$_2$CH$_2$OCH$_2$CH$_2$OMe |
| 44 | N | H | CH$_2$CH$_2$OCH$_2$CH$_2$SH |
| 45 | N | H | CH$_2$CH$_2$OCH$_2$CH$_2$SMe |
| 46 | N | H | CH$_2$CH$_2$OCH$_2$CH$_2$S(=O)Me |
| 47 | N | H | CH$_2$CH$_2$OCH$_2$CH$_2$SO$_2$Me |
| 48 | N | H | CH$_2$CH$_2$OCH$_2$CH$_2$SO$_2$NHMe |
| 49 | N | H | CH$_2$CH$_2$O(CH$_2$)$_2$SO$_2$N(Me)$_2$ |
| 50 | N | H | (CH$_2$)$_2$O(CH$_2$)$_2$OC(=O)NHMe |
| 51 | N | H | (CH$_2$)$_2$O(CH$_2$)$_2$OC(=O)N(Me)$_2$ |
| 52 | N | H | CH$_2$CH$_2$OCH$_2$CH$_2$OCO$_2$Me |
| 53 | N | H | CH$_2$CH$_2$OCH$_2$OCO$_2$Me |
| 54 | N | H | CH$_2$CH$_2$OCH$_2$C(=O)NHMe |
| 55 | N | H | CH$_2$CH$_2$NHCH$_2$CF$_3$ |
| 56 | N | H | CH$_2$CH$_2$N(Me)CH$_2$CF$_3$ |
| 57 | N | H | CH$_2$CH$_2$N=CH-(2-Py) |
| 58 | N | H | CH$_2$CH$_2$N=CH-(3-Py) |
| 59 | N | H | CH$_2$CH$_2$NHC(=O)Me |
| 60 | N | H | CH$_2$CH$_2$SCN |
| 61 | N | H | CH$_2$Si(Me)$_3$ |
| 62 | N | H | CH$_2$Si(Me)$_2$Ph |
| 63 | N | H | CH$_2$Si(Me)$_2$Et |
| 64 | N | H | CH$_2$C(=O)OCH$_2$CH$_2$OMe |
| 65 | N | H | CH$_2$C(=O)OCH$_2$CH$_2$OEt |
| 66 | N | H | CH$_2$C(=S)SMe |
| 67 | N | H | CH$_2$C(=S)OMe |
| 68 | N | H | CH$_2$C(=O)SMe |
| 69 | N | H | CH$_2$C(=S)Me |
| 70 | N | H | CH$_2$C(=S)N(Me)$_2$ |
| 71 | N | H | CH$_2$C(=S)NHMe |
| 72 | N | H | CH$_2$C(=S)NHCH$_2$CF$_3$ |
| 73 | N | H | CH$_2$P(=O)(OMe)$_2$ |
| 74 | N | H | CH$_2$P(=S)(OMe)$_2$ |
| 75 | CH | CO$_2$Me | (CH$_2$)$_2$O(CH$_2$)$_2$SMe |
| 76 | CH | CO$_2$Me | (CH$_2$)$_2$O(CH$_2$)$_2$S(=O)Me |
| 77 | CH | CO$_2$Me | (CH$_2$)$_2$O(CH$_2$)$_2$SO$_2$Me |
| 78 | CH | Et | (CH$_2$)$_2$O(CH$_2$)$_2$SMe |

TABLES 25-32-continued

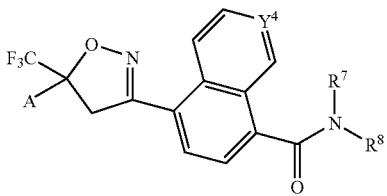

| Line | Y⁴ | R⁷ | R⁸ |
|---|---|---|---|
| 79 | CH | Et | (CH₂)₂O(CH₂)₂S(=O)Me |
| 80 | CH | Et | (CH₂)₂O(CH₂)₂SO₂Me |

A is:

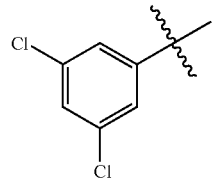

A-1-1
Table 25

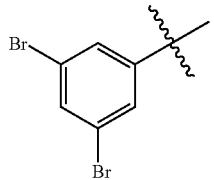

A-1-2
Table 26

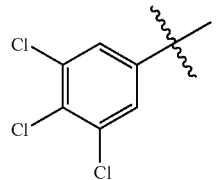

A-1-3
Table 27

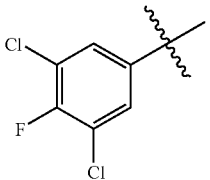

A-1-4
Table 28

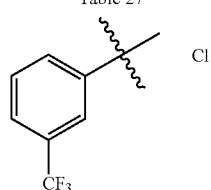

A-1-5
Table 29

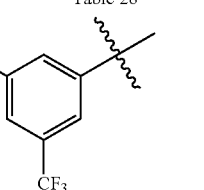

A-1-6
Table 30

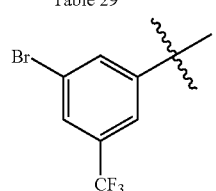

A-1-7
Table 31

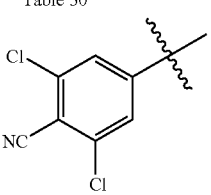

A-1-8
Table 32

TABLES 33-40

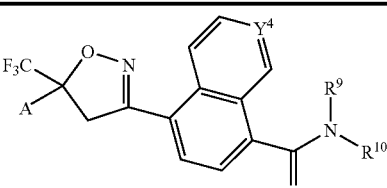

| Line | Y⁴ | R⁹ | R¹⁰ |
|---|---|---|---|
| 1 | CH | H | CN |
| 2 | CH | H | SO₂Me |
| 3 | CH | H | SO₂Ph |

TABLES 33-40-continued

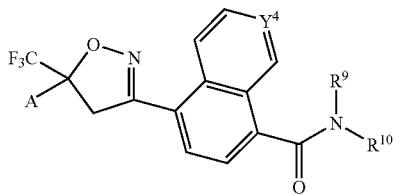

| Line | Y⁴ | R⁹ | R¹⁰ |
|---|---|---|---|
| 4 | CH | H | SO₂N(Me)₂ |
| 5 | CH | H | NHMe |
| 6 | CH | H | N(Me)₂ |
| 7 | CH | H | C(=O)CF₃ |
| 8 | CH | H | CO₂CH₂CF₃ |
| 9 | CH | H | C(=O)N(Me)₂ |
| 10 | CH | H | C(=O)NHMe |
| 11 | CH | CH₂CF₃ | CN |
| 12 | CH | CH₂CF₃ | SO₂Me |
| 13 | CH | CH₂CF₃ | SO₂Ph |
| 14 | CH | CH₂CF₃ | SO₂N(Me)₂ |
| 15 | CH | CH₂CF₃ | NHMe |
| 16 | CH | CH₂CF₃ | N(Me)₂ |
| 17 | CH | CH₂CF₃ | C(=O)CF₃ |
| 18 | CH | CH₂CF₃ | CO₂CH₂CF₃ |
| 19 | CH | CH₂CF₃ | C(=O)N(Me)₂ |
| 20 | CH | CH₂CF₃ | C(=O)NHMe |
| 21 | CH | CH₂-2-Py | CN |
| 22 | CH | CH₂-2-Py | SO₂Me |
| 23 | CH | CH₂-2-Py | SO₂Ph |
| 24 | CH | CH₂-2-Py | SO₂N(Me)₂ |
| 25 | CH | CH₂-2-Py | NHMe |
| 26 | CH | CH₂-2-Py | N(Me)₂ |
| 27 | CH | CH₂-2-Py | C(=O)CF₃ |
| 28 | CH | CH₂-2-Py | CO₂CH₂CF₃ |
| 29 | CH | CH₂-2-Py | C(=O)N(Me)₂ |
| 30 | CH | CH₂-2-Py | C(=O)NHMe |
| 31 | N | CH₂CF₃ | CH₂OMe |
| 32 | N | CH₂-2-Py | CH₂OMe |
| 33 | N | CH₂CH₂SMe | CH₂OMe |
| 34 | N | CH₂CH₂SO₂Me | CH₂OMe |
| 35 | N | CH₂CH₂S(=O)Me | CH₂OMe |
| 36 | N | Et | CN |
| 37 | N | Et | SO₂Me |
| 38 | N | Et | SO₂Ph |
| 39 | N | Et | SO₂N(Me)₂ |
| 40 | N | Et | NHMe |
| 41 | N | Et | N(Me)₂ |
| 42 | CH | H | C(=O)CF₃ |
| 43 | N | Et | CO₂CH₂CF₃ |
| 44 | N | Et | C(=O)N(Me)₂ |
| 45 | N | Et | C(=O)NHMe |
| 46 | CH | CH₂-c-Pr | CN |
| 47 | CH | CH₂-c-Pr | SO₂Me |
| 48 | CH | CH₂-c-Pr | SO₂Ph |
| 49 | CH | CH₂-c-Pr | SO₂N(Me)₂ |
| 50 | CH | CH₂-c-Pr | NHMe |
| 51 | CH | CH₂-c-Pr | N(Me)₂ |
| 52 | CH | CH₂-c-Pr | C(=O)CF₃ |
| 53 | CH | CH₂-c-Pr | CO₂CH₂CF₃ |
| 54 | CH | CH₂-c-Pr | C(=O)N(Me)₂ |
| 55 | CH | CH₂-c-Pr | C(=O)NHMe |
| 56 | N | CH₂CH₂SMe | CN |
| 57 | N | CH₂CH₂SMe | SO₂Me |
| 58 | N | CH₂CH₂SMe | SO₂Ph |
| 59 | N | CH₂CH₂SMe | SO₂N(Me)₂ |
| 60 | N | CH₂CH₂SMe | NHMe |
| 61 | N | CH₂CH₂SMe | N(Me)₂ |
| 62 | N | CH₂CH₂SMe | C(=O)CF₃ |
| 63 | N | CH₂CH₂SMe | CO₂CH₂CF₃ |
| 64 | N | CH₂CH₂SMe | C(=O)N(Me)₂ |
| 65 | N | CH₂CH₂SMe | C(=O)NHMe |
| 66 | N | CH₂CF₃ | CH₂CO₂Me |
| 67 | N | CH₂-2-Py | CH₂CO₂Me |
| 68 | N | CH₂CH₂SMe | CH₂CO₂Me |
| 69 | N | CH₂CH₂SO₂Me | CH₂CO₂Me |
| 70 | N | CH₂CH₂S(=O)Me | CH₂CO₂Me |

TABLES 33-40-continued

[Structure: F₃C-isoxazoline-A substituent on naphthalene with Y⁴ and C(O)NR⁹R¹⁰ groups]

| Line | Y⁴ | R⁹ | R¹⁰ |
|------|----|----|-----|

A is:

| A-1-1 (Table 33): 3,5-dichlorophenyl | A-1-2 (Table 34): 3,5-dibromophenyl |
| A-1-3 (Table 35): 3,4,5-trichlorophenyl | A-1-4 (Table 36): 3,5-dichloro-4-fluorophenyl |
| A-1-5 (Table 37): 3-(trifluoromethyl)phenyl | A-1-6 (Table 38): 3-chloro-5-(trifluoromethyl)phenyl |
| A-1-7 (Table 39): 3-bromo-5-(trifluoromethyl)phenyl | A-1-8 (Table 40): 2,6-dichloro-4-cyanophenyl |

TABLES 41-48

[Structure: F₃C-isoxazoline-A substituent on naphthalene with C(O)N(R¹¹)-C(R¹²)(R¹³)-C(O)N(R¹⁴)R¹⁵]

| Line | R¹¹ | R¹² | R¹³ | R¹⁴ | R¹⁵ |
|------|-----|-----|-----|-----|-----|
| 1 | H | H | H | H | CH₂Ph |
| 2 | H | H | H | H | CH₂-2-Py |
| 3 | H | H | H | H | CH₂-3-Py |
| 4 | H | H | H | H | CH₂CH₂OH |
| 5 | H | H | H | H | CH(CH₃)CH₂OH |
| 6 | H | H | H | H | C(CH₃)₂CH₂OH |

TABLES 41-48-continued

| Line | R¹¹ | R¹² | R¹³ | R¹⁴ | R¹⁵ |
|------|-----|-----|-----|-----|-----|
| 7 | H | H | H | H | CH₂CH₂OMe |
| 8 | H | H | H | H | CH(CH₃)CH₂OMe |
| 9 | H | H | H | H | C(CH₃)₂CH₂OMe |
| 10 | H | H | H | H | CH₂CH₂SMe |
| 11 | H | H | H | H | CH₂CH₂S(=O)Me |
| 12 | H | H | H | H | CH₂CH₂SO₂Me |
| 13 | H | H | H | H | CH(Me)CH₂SMe |
| 14 | H | H | H | H | CHMeCH₂S(=O)Me |
| 15 | H | H | H | H | CH(Me)CH₂SO₂Me |
| 16 | H | H | H | H | C(Me)₂CH₂SMe |
| 17 | H | H | H | H | C(Me)₂CH₂S(=O)Me |
| 18 | H | H | H | H | C(Me)₂CH₂SO₂Me |
| 19 | H | H | H | H | CH₂C(=O)NHMe |
| 20 | H | H | H | H | CH₂C(=O)N(Me)₂ |
| 21 | H | H | H | H | CH₂C(=O)NHEt |
| 22 | H | H | H | H | CH₂C(=O)NH-c-Pr |
| 23 | H | H | H | H | CH₂C(=O)NHCH₂CF₃ |
| 24 | Me | H | H | H | CH₂Ph |
| 25 | Me | H | H | H | CH₂-2-Py |
| 26 | Me | H | H | H | CH₂-3-Py |
| 27 | Me | H | H | H | CH₂CH₂OH |
| 28 | Me | H | H | H | CH(CH₃)CH₂OH |
| 29 | Me | H | H | H | C(CH₃)₂CH₂OH |
| 30 | Me | H | H | H | CH₂CH₂OMe |
| 31 | Me | H | H | H | CH(CH₃)CH₂OMe |
| 32 | Me | H | H | H | C(CH₃)₂CH₂OMe |
| 33 | Me | H | H | H | CH₂CH₂SMe |
| 34 | Me | H | H | H | CH₂CH₂S(=O)Me |
| 35 | Me | H | H | H | CH₂CH₂SO₂Me |
| 36 | Me | H | H | H | CH(Me)CH₂SMe |
| 37 | Me | H | H | H | CHMeCH₂S(=O)Me |
| 38 | Me | H | H | H | CH(Me)CH₂SO₂Me |
| 39 | Me | H | H | H | C(Me)₂CH₂SMe |
| 40 | Me | H | H | H | C(Me)₂CH₂S(=O)Me |
| 41 | Me | H | H | H | C(Me)₂CH₂SO₂Me |
| 42 | Me | H | H | H | CH₂C(=O)NHMe |
| 43 | Me | H | H | H | CH₂C(=O)N(Me)₂ |
| 44 | Me | H | H | H | CH₂C(=O)NHEt |
| 45 | Me | H | H | H | CH₂C(=O)NH-c-Pr |
| 46 | Me | H | H | H | CH₂C(=O)NHCH₂CF₃ |
| 47 | H | H | H | Me | CH₂Ph |
| 48 | H | H | H | Me | CH₂-2-Py |
| 49 | H | H | H | Me | CH₂-3-Py |
| 50 | H | H | H | Me | CH₂CH₂OH |
| 51 | H | H | H | Me | CH(CH₃)CH₂OH |
| 52 | H | H | H | Me | C(CH₃)₂CH₂OH |
| 53 | H | H | H | Me | CH₂CH₂OMe |
| 54 | H | H | H | Me | CH(CH₃)CH₂OMe |
| 55 | H | H | H | Me | C(CH₃)₂CH₂OMe |
| 56 | H | H | H | Me | CH₂CH₂SMe |
| 57 | H | H | H | Me | CH₂CH₂S(=O)Me |
| 58 | H | H | H | Me | CH₂CH₂SO₂Me |
| 59 | H | H | H | Me | CH(Me)CH₂SMe |
| 60 | H | H | H | Me | CHMeCH₂S(=O)Me |
| 61 | H | H | H | Me | CH(Me)CH₂SO₂Me |
| 62 | H | H | H | Me | C(Me)₂CH₂SMe |
| 63 | H | H | H | Me | C(Me)₂CH₂S(=O)Me |
| 64 | H | H | H | Me | C(Me)₂CH₂SO₂Me |
| 65 | H | H | H | Me | CH₂C(=O)NHMe |
| 66 | H | H | H | Me | CH₂C(=O)N(Me)₂ |
| 67 | H | H | H | Me | CH₂C(=O)NHEt |
| 68 | H | H | H | Me | CH₂C(=O)NH-c-Pr |
| 69 | H | H | H | Me | CH₂C(=O)NHCH₂CF₃ |
| 70 | H | Me | H | H | CH₂Ph |
| 71 | H | Me | H | H | CH₂-2-Py |
| 72 | H | Me | H | H | CH₂-3-Py |
| 73 | H | Me | H | H | CH₂CH₂OH |
| 74 | H | Me | H | H | CH(CH₃CH₂OH |

TABLES 41-48-continued

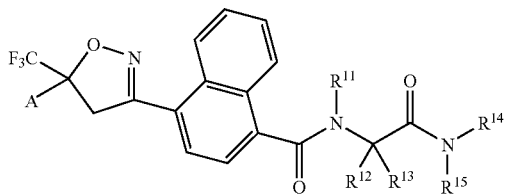

| Line | R11 | R12 | R13 | R14 | R15 |
|---|---|---|---|---|---|
| 75 | H | Me | H | H | C(CH3)2CH2OH |
| 76 | H | Me | H | H | CH2CH2OMe |
| 77 | H | Me | H | H | CH(CH3)CH2OMe |
| 78 | H | Me | H | H | C(CH3)2CH2OMe |
| 79 | H | Me | H | H | CH2CH2SMe |
| 80 | H | Me | H | H | CH2CH2S(=O)Me |
| 81 | H | Me | H | H | CH2CH2SO2Me |
| 82 | H | Me | H | H | CH(Me)CH2SMe |
| 83 | H | Me | H | H | CHMeCH2S(=O)Me |
| 84 | H | Me | H | H | CH(Me)CH2SO2Me |
| 85 | H | Me | H | H | C(Me)2CH2SMe |
| 86 | H | Me | H | H | C(Me)2CH2S(=O)Me |
| 87 | H | Me | H | H | C(Me)2CH2SO2Me |
| 88 | H | Me | H | H | CH2C(=O)NHMe |
| 89 | H | Me | H | H | CH2C(=O)N(Me)2 |
| 90 | H | Me | H | H | CH2C(=O)NHEt |
| 91 | H | Me | H | H | CH2C(=O)NH-c-Pr |
| 92 | H | Me | H | H | CH2C(=O)NHCH2CF3 |
| 93 | H | Me | Me | H | CH2Ph |
| 94 | H | Me | Me | H | CH2-2-Py |
| 95 | H | Me | Me | H | CH2-3-Py |
| 96 | H | Me | Me | H | CH2CH2OH |
| 97 | H | Me | Me | H | CH(CH3)CH2OH |
| 98 | H | Me | Me | H | C(CH3)2CH2OH |
| 99 | H | Me | Me | H | CH2CH2OMe |
| 100 | H | Me | Me | H | CH(CH3)CH2OMe |
| 101 | H | Me | Me | H | C(CH3)2CH2OMe |
| 102 | H | Me | Me | H | CH2CH2SMe |
| 103 | H | Me | Me | H | CH2CH2S(=O)Me |
| 104 | H | Me | Me | H | CH2CH2SO2Me |
| 105 | H | Me | Me | H | CH(Me)CH2SMe |
| 106 | H | Me | Me | H | CHMeCH2S(=O)Me |
| 107 | H | Me | Me | H | CH(Me)CH2SO2Me |
| 108 | H | Me | Me | H | C(Me)2CH2SMe |
| 109 | H | Me | Me | H | C(Me)2CH2S(=O)Me |
| 110 | H | Me | Me | H | C(Me)2CH2SO2Me |
| 111 | H | Me | Me | H | CH2C(=O)NHMe |
| 112 | H | Me | Me | H | CH2C(=O)N(Me)2 |
| 113 | H | Me | Me | H | CH2C(=O)NHEt |
| 114 | H | Me | Me | H | CH2C(=O)NH-c-Pr |
| 115 | H | Me | Me | H | CH2C(=O)NHCH2CF3 |
| 116 | H | H | Me | Me | CH2Ph |
| 117 | H | H | Me | Me | CH2-2-Py |
| 118 | H | H | Me | Me | CH2-3-Py |
| 119 | H | H | Me | Me | CH2CH2OH |
| 120 | H | H | Me | Me | CH(CH3)CH2OH |
| 121 | H | H | Me | Me | C(CH3)2CH2OH |
| 122 | H | H | Me | Me | CH2CH2OMe |
| 123 | H | H | Me | Me | CH(CH3)CH2OMe |
| 124 | H | H | Me | Me | C(CH3)2CH2OMe |
| 125 | H | H | Me | Me | CH2CH2SMe |
| 126 | H | H | Me | Me | CH2CH2S(=O)Me |
| 127 | H | H | Me | Me | CH2CH2SO2Me |
| 128 | H | H | Me | Me | CH(Me)CH2SMe |
| 129 | H | H | Me | Me | CHMeCH2S(=O)Me |
| 130 | H | H | Me | Me | CH(Me)CH2SO2Me |
| 131 | H | H | Me | Me | C(Me)2CH2SMe |
| 132 | H | H | Me | Me | C(Me)2CH2S(=O)Me |
| 133 | H | H | Me | Me | C(Me)2CH2SO2Me |
| 134 | H | H | Me | Me | CH2C(=O)NHMe |
| 135 | H | H | Me | Me | CH2C(=O)N(Me)2 |
| 136 | H | H | Me | Me | CH2C(=O)NHEt |
| 137 | H | H | Me | Me | CH2C(=O)NH-c-Pr |
| 138 | H | H | Me | Me | CH2C(=O)NHCH2CF3 |

A is:

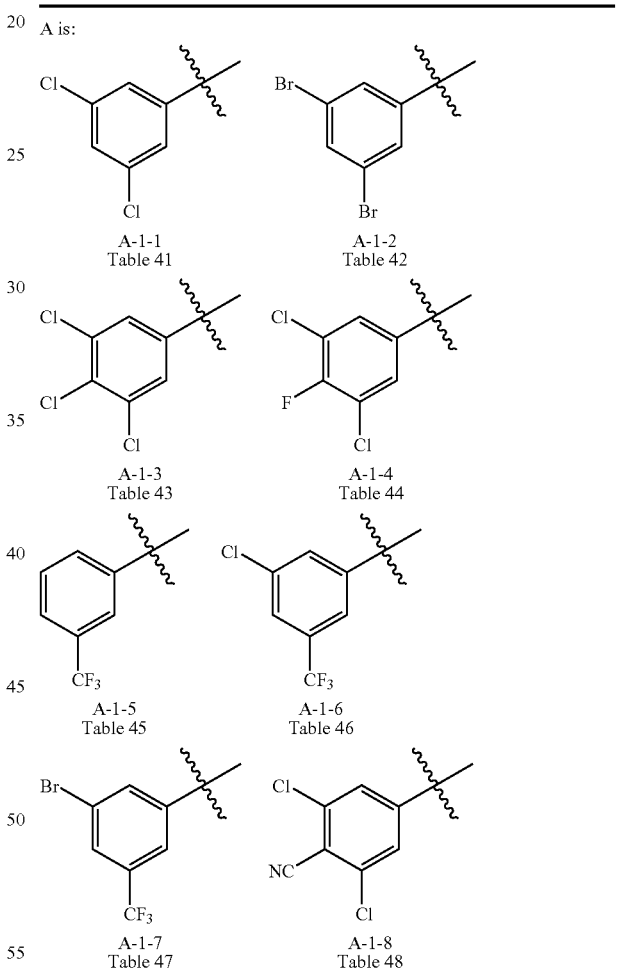

TABLE 49

| Cmpd. | Cmpd. | Cmpd. | Cmpd. | Cmpd. | Cmpd. | Cmpd. | Cmpd. | Cmpd. | Cmpd. | Cmpd. |
|---|---|---|---|---|---|---|---|---|---|---|
| 1-1 | 1-2 | 1-3 | 1-4 | 1-5 | 1-6 | 1-7 | 1-8 | 1-9 | 1-10 | 1-11 |
| 1-12 | 1-13 | 1-14 | 1-15 | 1-16 | 1-17 | 1-18 | 1-19 | 1-20 | 1-21 | 1-22 |
| 1-23 | 1-24 | 1-25 | 1-26 | 1-27 | 1-28 | 1-29 | 1-30 | 1-31 | 1-32 | 1-33 |
| 1-34 | 1-35 | 1-36 | 1-37 | 1-38 | 1-39 | 1-40 | 1-41 | 1-42 | 1-43 | 1-44 |
| 1-45 | 1-46 | 1-47 | 1-48 | 1-49 | 1-50 | 1-51 | 1-52 | 1-53 | 1-54 | 1-55 |

TABLE 49-continued

| Cmpd. | Cmpd. | Cmpd. | Cmpd. | Cmpd. | Cmpd. | Cmpd. | Cmpd. | Cmpd. | Cmpd. | Cmpd. |
|---|---|---|---|---|---|---|---|---|---|---|
| 1-56 | 1-57 | 1-58 | 1-59 | 1-60 | 1-61 | 1-62 | 1-63 | 1-64 | 1-65 | 1-66 |
| 1-67 | 1-68 | 1-69 | 1-70 | 1-71 | 1-72 | 1-73 | 1-74 | 1-75 | 1-76 | 1-77 |
| 1-78 | 1-79 | 1-80 | 1-81 | 1-82 | 1-83 | 1-84 | 1-85 | 1-86 | 1-87 | 1-88 |
| 1-89 | 1-90 | 1-91 | 1-92 | 1-93 | 1-94 | 1-95 | 1-96 | 1-97 | 1-98 | 1-99 |
| 1-100 | 1-101 | 1-102 | 1-103 | 1-104 | 1-105 | 1-106 | 1-107 | 1-108 | 1-109 | 1-110 |
| 1-111 | 1-112 | 1-113 | 1-114 | 1-115 | 1-116 | 1-117 | 1-118 | 1-119 | 1-120 | 1-121 |
| 1-122 | 1-123 | 1-124 | 1-125 | 1-126 | 1-127 | 1-128 | 1-129 | 1-130 | 1-131 | 1-132 |
| 1-133 | 1-134 | 1-135 | 1-136 | 1-137 | 1-138 | 1-139 | 1-140 | 1-141 | 1-142 | 1-143 |
| 1-144 | 1-145 | 1-146 | 1-147 | 1-148 | 1-149 | 1-150 | 1-151 | 1-152 | 1-153 | 1-154 |
| 1-155 | 1-156 | 1-157 | 1-158 | 1-159 | 1-160 | 1-161 | 1-162 | 1-163 | 1-164 | 1-165 |
| 1-166 | 1-167 | 1-168 | 1-169 | 1-170 | 1-171 | 1-172 | 1-173 | 1-174 | 1-175 | 1-176 |
| 1-177 | 1-178 | 1-179 | 1-180 | 1-181 | 1-182 | 1-183 | 1-184 | 2-93 | 2-94 | 2-95 |
| 2-96 | 2-97 | 2-98 | 2-99 | 2-100 | 2-101 | 2-102 | 2-103 | 2-104 | 2-105 | 2-106 |
| 2-107 | 3-93 | 3-94 | 3-95 | 3-96 | 3-97 | 3-98 | 3-99 | 3-100 | 3-101 | 3-102 |
| 3-103 | 3-104 | 3-105 | 3-106 | 3-107 | 4-93 | 4-94 | 4-95 | 4-96 | 4-97 | 4-98 |
| 4-99 | 4-100 | 4-101 | 4-102 | 4-103 | 4-104 | 4-105 | 4-106 | 4-107 | 4-108 | 4-109 |
| 5-1 | 5-2 | 5-3 | 5-4 | 5-5 | 5-6 | 5-7 | 5-8 | 5-9 | 5-10 | 5-11 |
| 5-12 | 5-13 | 5-14 | 5-15 | 5-16 | 5-17 | 5-18 | 5-19 | 5-20 | 5-21 | 5-22 |
| 5-23 | 5-24 | 5-25 | 5-26 | 5-27 | 5-28 | 5-29 | 5-30 | 5-31 | 5-32 | 5-33 |
| 5-34 | 5-35 | 5-36 | 5-37 | 5-38 | 5-39 | 5-40 | 5-41 | 5-42 | 5-43 | 5-44 |
| 5-45 | 5-46 | 5-47 | 5-48 | 5-49 | 5-50 | 5-51 | 5-52 | 5-53 | 5-54 | 5-55 |
| 5-56 | 5-57 | 5-58 | 5-59 | 5-60 | 5-61 | 5-62 | 5-63 | 5-64 | 5-65 | 5-66 |
| 5-67 | 5-68 | 5-69 | 5-70 | 5-71 | 5-72 | 5-73 | 5-74 | 5-75 | 5-76 | 5-77 |
| 5-78 | 5-79 | 5-80 | 5-81 | 5-82 | 5-83 | 5-84 | 5-85 | 5-86 | 5-87 | 5-88 |
| 5-89 | 5-90 | 5-91 | 5-92 | 5-93 | 5-94 | 5-95 | 5-96 | 5-97 | 5-98 | 5-99 |
| 5-100 | 5-101 | 5-102 | 5-103 | 5-104 | 5-105 | 5-106 | 5-107 | 5-108 | 5-109 | 5-110 |
| 5-111 | 5-112 | 5-113 | 5-114 | 5-115 | 5-116 | 5-117 | 5-118 | 5-119 | 5-120 | 5-121 |
| 5-122 | 5-123 | 5-124 | 5-125 | 5-126 | 5-127 | 5-128 | 5-129 | 5-130 | 5-131 | 5-132 |
| 5-133 | 5-134 | 5-135 | 5-136 | 5-137 | 5-138 | 5-139 | 5-140 | 5-141 | 5-142 | 5-143 |
| 5-144 | 5-145 | 5-146 | 5-147 | 5-148 | 5-149 | 5-150 | 5-151 | 5-152 | 5-153 | 5-154 |
| 5-155 | 5-156 | 5-157 | 5-158 | 5-159 | 5-160 | 5-161 | 5-162 | 5-163 | 5-164 | 5-165 |
| 5-166 | 5-167 | 5-168 | 5-169 | 5-170 | 5-171 | 5-172 | 5-173 | 5-174 | 5-175 | 5-176 |
| 5-177 | 5-178 | 5-179 | 5-180 | 5-181 | 5-182 | 5-183 | 5-184 | 6-93 | 6-94 | 6-95 |
| 6-96 | 6-97 | 6-98 | 6-99 | 6-100 | 6-101 | 6-102 | 6-103 | 6-104 | 6-105 | 6-106 |
| 6-107 | 7-93 | 7-94 | 7-95 | 7-96 | 7-97 | 7-98 | 7-99 | 7-100 | 7-101 | 7-102 |
| 7-103 | 7-104 | 7-105 | 7-106 | 7-107 | 8-93 | 8-94 | 8-95 | 8-96 | 8-97 | 8-98 |
| 8-99 | 8-100 | 8-101 | 8-102 | 8-103 | 8-104 | 8-105 | 8-106 | 8-107 | 8-108 | 8-109 |
| 9-1 | 9-2 | 9-3 | 9-4 | 9-5 | 9-6 | 9-7 | 9-8 | 9-9 | 9-10 | 9-11 |
| 9-12 | 9-13 | 9-14 | 9-15 | 9-16 | 9-17 | 9-18 | 9-19 | 9-20 | 9-21 | 9-22 |
| 9-23 | 9-24 | 9-25 | 9-26 | 9-27 | 9-28 | 9-29 | 9-30 | 9-31 | 9-32 | 9-33 |
| 9-34 | 9-35 | 9-36 | 9-37 | 9-38 | 9-39 | 9-40 | 9-41 | 9-42 | 9-43 | 9-44 |
| 9-45 | 9-46 | 9-47 | 9-48 | 9-49 | 9-50 | 9-51 | 9-52 | 9-53 | 9-54 | 9-55 |
| 9-56 | 9-57 | 9-58 | 9-59 | 9-60 | 10-1 | 10-2 | 10-3 | 10-4 | 10-5 | 10-6 |
| 10-7 | 10-8 | 10-9 | 10-10 | 11-1 | 11-2 | 11-3 | 11-4 | 11-5 | 11-6 | 11-7 |
| 11-8 | 11-9 | 11-10 | 12-1 | 12-2 | 12-3 | 12-4 | 12-5 | 12-6 | 12-7 | 12-8 |
| 12-9 | 12-10 | 13-1 | 13-2 | 13-3 | 13-4 | 13-5 | 13-6 | 13-7 | 13-8 | 13-9 |
| 13-10 | 14-1 | 14-2 | 14-3 | 14-4 | 14-5 | 14-6 | 14-7 | 14-8 | 14-9 | 14-10 |
| 15-1 | 15-2 | 15-3 | 15-4 | 15-5 | 15-6 | 15-7 | 15-8 | 15-9 | 15-10 | 16-1 |
| 16-2 | 16-3 | 16-4 | 16-5 | 16-6 | 16-7 | 16-8 | 16-9 | 16-10 | 16-11 | 16-12 |
| 17-1 | 17-2 | 17-3 | 17-4 | 17-5 | 17-6 | 17-7 | 17-8 | 17-9 | 17-10 | 17-11 |
| 17-12 | 17-13 | 17-14 | 17-15 | 17-16 | 17-17 | 17-18 | 17-19 | 17-20 | 17-21 | 17-22 |
| 17-23 | 17-24 | 17-25 | 17-26 | 17-27 | 17-28 | 17-29 | 17-30 | 17-31 | 17-32 | 17-33 |
| 17-34 | 17-35 | 17-36 | 17-37 | 17-38 | 17-39 | 17-40 | 17-41 | 17-42 | 17-43 | 17-44 |
| 17-45 | 17-46 | 17-47 | 17-48 | 17-49 | 17-50 | 17-51 | 17-52 | 17-53 | 17-54 | 17-55 |
| 17-56 | 17-57 | 17-58 | 17-59 | 17-60 | 18-1 | 18-2 | 18-3 | 18-4 | 18-5 | 18-6 |
| 18-7 | 18-8 | 18-9 | 18-10 | 19-1 | 19-2 | 19-3 | 19-4 | 19-5 | 19-6 | 19-7 |
| 19-8 | 19-9 | 19-10 | 20-1 | 20-2 | 20-3 | 20-4 | 20-5 | 20-6 | 20-7 | 20-8 |
| 20-9 | 20-10 | 20-11 | 20-12 | 20-13 | 20-14 | 20-15 | 20-16 | 20-17 | 20-18 | 20-19 |
| 21-1 | 21-2 | 21-3 | 21-4 | 21-5 | 21-6 | 21-7 | 21-8 | 21-9 | 21-10 | 21-11 |
| 21-12 | 21-13 | 21-14 | 21-15 | 21-16 | 21-17 | 21-18 | 21-19 | 21-20 | 21-21 | 21-22 |
| 21-23 | 21-24 | 21-25 | 21-26 | 21-27 | 21-28 | 21-29 | 21-30 | 21-31 | 21-32 | 21-33 |
| 21-34 | 21-35 | 21-36 | 21-37 | 21-38 | 21-39 | 21-40 | 21-41 | 21-42 | 21-43 | 21-44 |
| 21-45 | 21-46 | 21-47 | 21-48 | 21-49 | 21-50 | 21-51 | 21-52 | 21-53 | 21-54 | 21-55 |
| 21-56 | 21-57 | 21-58 | 21-59 | 21-60 | 22-1 | 22-2 | 22-3 | 22-4 | 22-5 | 22-6 |
| 22-7 | 22-8 | 22-9 | 22-10 | 23-1 | 23-2 | 23-3 | 23-4 | 23-5 | 23-6 | 23-7 |
| 23-8 | 23-9 | 23-10 | 24-1 | 24-2 | 24-3 | 24-4 | 24-5 | 24-6 | 24-7 | 24-8 |
| 24-9 | 24-10 | 24-11 | 24-12 | 24-13 | 24-14 | 24-15 | 24-16 | 24-17 | 24-18 | 24-19 |
| 25-1 | 25-2 | 25-3 | 25-4 | 25-5 | 25-6 | 25-7 | 25-8 | 25-9 | 25-10 | 25-11 |
| 25-12 | 25-13 | 25-14 | 25-15 | 25-16 | 25-17 | 25-18 | 25-19 | 25-20 | 25-21 | 25-22 |
| 25-23 | 25-24 | 25-25 | 25-26 | 25-27 | 25-28 | 25-29 | 25-30 | 25-31 | 25-32 | 25-33 |
| 25-34 | 25-35 | 25-36 | 25-37 | 25-38 | 25-39 | 25-40 | 25-41 | 25-42 | 25-43 | 25-44 |
| 25-45 | 25-46 | 25-47 | 25-48 | 25-49 | 25-50 | 25-51 | 25-52 | 25-53 | 25-54 | 25-55 |
| 25-56 | 25-57 | 25-58 | 25-59 | 25-60 | 25-61 | 25-62 | 25-63 | 25-64 | 25-65 | 25-66 |
| 25-67 | 25-68 | 25-69 | 25-70 | 25-71 | 25-72 | 25-73 | 25-74 | 25-75 | 25-76 | 25-77 |
| 25-78 | 25-79 | 25-80 | 26-1 | 26-2 | 26-3 | 26-4 | 26-5 | 26-6 | 26-7 | 27-1 |
| 27-2 | 27-3 | 27-4 | 27-5 | 27-6 | 27-7 | 28-1 | 28-2 | 28-3 | 28-4 | 28-5 |
| 28-6 | 28-7 | 29-1 | 29-2 | 29-3 | 29-4 | 29-5 | 29-6 | 29-7 | 30-1 | 30-2 |
| 30-3 | 30-4 | 30-5 | 30-6 | 30-7 | 31-1 | 31-2 | 31-3 | 31-4 | 31-5 | 31-6 |

TABLE 49-continued

| Cmpd. | Cmpd. | Cmpd. | Cmpd. | Cmpd. | Cmpd. | Cmpd. | Cmpd. | Cmpd. | Cmpd. | Cmpd. |
|---|---|---|---|---|---|---|---|---|---|---|
| 31-7 | 32-1 | 32-2 | 32-3 | 32-4 | 32-5 | 32-6 | 32-7 | 32-8 | 32-9 | 32-10 |
| 33-1 | 33-2 | 33-3 | 33-4 | 33-5 | 33-6 | 33-7 | 33-8 | 33-9 | 33-10 | 33-11 |
| 33-12 | 33-13 | 33-14 | 33-15 | 33-16 | 33-17 | 33-18 | 33-19 | 33-20 | 33-21 | 33-22 |
| 33-23 | 33-24 | 33-25 | 33-26 | 33-27 | 33-28 | 33-29 | 33-30 | 33-31 | 33-32 | 33-33 |
| 33-34 | 33-35 | 33-36 | 33-37 | 33-38 | 33-39 | 33-40 | 33-41 | 33-42 | 33-43 | 33-44 |
| 33-45 | 33-46 | 33-47 | 33-48 | 33-49 | 33-50 | 33-51 | 33-52 | 33-53 | 33-54 | 33-55 |
| 33-56 | 33-57 | 33-58 | 33-59 | 33-60 | 33-61 | 33-62 | 33-63 | 33-64 | 33-65 | 33-66 |
| 33-67 | 33-68 | 33-69 | 33-70 | 34-11 | 34-12 | 34-13 | 34-14 | 34-15 | 34-16 | 34-17 |
| 34-18 | 34-19 | 34-20 | 34-21 | 34-22 | 34-23 | 34-24 | 34-25 | 34-26 | 34-27 | 34-28 |
| 34-29 | 34-30 | 34-46 | 34-47 | 34-48 | 34-49 | 34-50 | 34-51 | 34-52 | 34-53 | 34-54 |
| 34-55 | 35-11 | 35-12 | 35-13 | 35-14 | 35-15 | 35-16 | 35-17 | 35-18 | 35-19 | 35-20 |
| 35-20 | 35-21 | 35-22 | 35-23 | 35-24 | 35-25 | 35-26 | 35-27 | 35-28 | 35-29 | 35-30 |
| 35-46 | 35-47 | 35-48 | 35-49 | 35-50 | 35-51 | 35-52 | 35-53 | 35-54 | 35-55 | 36-11 |
| 36-12 | 36-13 | 36-14 | 36-15 | 36-16 | 36-17 | 36-18 | 36-19 | 36-20 | 36-22 | 36-23 |
| 36-24 | 36-25 | 36-26 | 36-27 | 36-28 | 36-29 | 36-30 | 36-46 | 36-47 | 36-48 | 36-49 |
| 36-49 | 36-50 | 36-51 | 36-52 | 36-53 | 36-54 | 36-55 | 37-11 | 37-12 | 37-13 | 37-14 |
| 37-14 | 37-15 | 37-16 | 37-17 | 37-18 | 37-19 | 37-20 | 37-22 | 37-23 | 37-24 | 37-25 |
| 37-26 | 37-27 | 37-28 | 37-29 | 37-30 | 37-46 | 37-47 | 37-48 | 37-49 | 37-50 | 37-51 |
| 37-52 | 37-53 | 37-54 | 37-55 | 38-11 | 38-12 | 38-13 | 38-14 | 38-15 | 38-16 | 38-17 |
| 38-18 | 38-19 | 38-20 | 38-21 | 38-22 | 38-23 | 38-24 | 38-25 | 38-26 | 38-27 | 38-28 |
| 38-29 | 38-30 | 38-46 | 38-47 | 38-48 | 38-49 | 38-50 | 38-51 | 38-52 | 38-53 | 38-54 |
| 38-55 | 39-11 | 39-12 | 39-13 | 39-14 | 39-15 | 39-16 | 39-17 | 39-18 | 39-19 | 39-20 |
| 39-20 | 39-21 | 39-22 | 39-23 | 39-24 | 39-25 | 39-26 | 39-27 | 39-28 | 39-29 | 39-30 |
| 39-46 | 39-47 | 39-48 | 39-49 | 39-50 | 39-51 | 39-52 | 39-53 | 39-54 | 39-55 | 40-11 |
| 40-12 | 40-13 | 40-14 | 40-15 | 40-16 | 40-17 | 40-18 | 40-19 | 40-20 | 40-22 | 40-23 |
| 40-24 | 40-25 | 40-26 | 40-27 | 40-28 | 40-29 | 40-30 | 40-46 | 40-47 | 40-48 | 40-49 |
| 40-50 | 40-51 | 40-52 | 40-53 | 40-54 | 40-55 | 40-56 | 40-57 | 40-58 | 40-59 | 40-60 |
| 41-1 | 41-2 | 41-3 | 41-4 | 41-5 | 41-6 | 41-7 | 41-8 | 41-9 | 41-10 | 41-11 |
| 41-12 | 41-13 | 41-14 | 41-15 | 41-16 | 41-17 | 41-18 | 41-19 | 41-20 | 41-21 | 41-22 |
| 41-23 | 41-24 | 41-25 | 41-26 | 41-27 | 41-28 | 41-29 | 41-30 | 41-31 | 41-32 | 41-33 |
| 41-34 | 41-35 | 41-36 | 41-37 | 41-38 | 41-39 | 41-40 | 41-41 | 41-42 | 41-43 | 41-44 |
| 41-45 | 41-46 | 41-47 | 41-48 | 41-49 | 41-50 | 41-51 | 41-52 | 41-53 | 41-54 | 41-55 |
| 41-56 | 41-57 | 41-58 | 41-59 | 41-60 | 41-61 | 41-62 | 41-63 | 41-64 | 41-65 | 41-66 |
| 41-67 | 41-68 | 41-69 | 41-70 | 41-71 | 41-72 | 41-73 | 41-74 | 41-75 | 41-76 | 41-77 |
| 41-78 | 41-79 | 41-80 | 41-81 | 41-82 | 41-83 | 41-84 | 41-85 | 41-86 | 41-87 | 41-88 |
| 41-89 | 41-90 | 41-91 | 41-92 | 41-93 | 41-94 | 41-95 | 41-96 | 41-97 | 41-98 | 41-99 |
| 41-100 | 41-101 | 41-102 | 41-103 | 41-104 | 41-105 | 41-106 | 41-107 | 41-108 | 41-109 | 41-110 |
| 41-111 | 41-112 | 41-113 | 41-114 | 41-115 | 41-116 | 41-117 | 41-118 | 41-119 | 41-120 | 41-121 |
| 41-122 | 41-123 | 41-124 | 41-125 | 41-126 | 41-127 | 41-128 | 41-129 | 41-130 | 41-131 | 41-132 |
| 41-133 | 41-134 | 41-135 | 41-136 | 41-137 | 41-138 | 42-1 | 42-2 | 42-3 | 42-4 | 42-5 |
| 42-6 | 42-7 | 42-8 | 42-9 | 42-10 | 42-11 | 42-12 | 42-13 | 42-14 | 42-15 | 42-16 |
| 42-17 | 42-18 | 42-19 | 42-20 | 42-21 | 42-22 | 42-23 | 42-70 | 42-71 | 42-72 | 42-73 |
| 42-74 | 42-75 | 42-76 | 42-77 | 42-78 | 42-79 | 42-80 | 42-81 | 42-82 | 42-83 | 42-84 |
| 42-85 | 42-86 | 42-87 | 42-88 | 42-89 | 42-90 | 42-91 | 42-92 | 43-1 | 43-2 | 43-3 |
| 43-4 | 43-5 | 43-6 | 43-7 | 43-8 | 43-9 | 43-10 | 43-11 | 43-12 | 43-13 | 43-14 |
| 43-15 | 43-16 | 43-17 | 43-18 | 43-19 | 43-20 | 43-21 | 43-22 | 43-23 | 43-70 | 43-71 |
| 43-72 | 43-73 | 43-74 | 43-75 | 43-76 | 43-77 | 43-78 | 43-79 | 43-80 | 43-81 | 43-82 |
| 43-83 | 43-84 | 43-85 | 43-86 | 43-87 | 43-88 | 43-89 | 43-90 | 43-91 | 43-92 | 44-1 |
| 44-2 | 44-3 | 44-4 | 44-5 | 44-6 | 44-7 | 44-8 | 44-9 | 44-10 | 44-11 | 44-12 |
| 44-13 | 44-14 | 44-15 | 44-16 | 44-17 | 44-18 | 44-19 | 44-20 | 44-21 | 44-22 | 44-23 |
| 44-70 | 44-71 | 44-72 | 44-73 | 44-74 | 44-75 | 44-76 | 44-77 | 44-78 | 44-79 | 44-80 |
| 44-81 | 44-82 | 44-83 | 44-84 | 44-85 | 44-86 | 44-87 | 44-88 | 44-89 | 44-90 | 44-91 |
| 44-92 | 45-1 | 45-2 | 45-3 | 45-4 | 45-5 | 45-6 | 45-7 | 45-8 | 45-9 | 45-10 |
| 45-11 | 45-12 | 45-13 | 45-14 | 45-15 | 45-16 | 45-17 | 45-18 | 45-19 | 45-20 | 45-21 |
| 45-22 | 45-23 | 45-70 | 45-71 | 45-72 | 45-73 | 45-74 | 45-75 | 45-76 | 45-77 | 45-78 |
| 45-79 | 45-80 | 45-81 | 45-82 | 45-83 | 45-84 | 45-85 | 45-86 | 45-87 | 45-88 | 45-89 |
| 45-90 | 45-91 | 45-92 | 46-1 | 46-2 | 46-3 | 46-4 | 46-5 | 46-6 | 46-7 | 46-8 |
| 46-9 | 46-10 | 46-11 | 46-12 | 46-13 | 46-14 | 46-15 | 46-16 | 46-17 | 46-18 | 46-19 |
| 46-20 | 46-21 | 46-22 | 46-23 | 46-70 | 46-71 | 46-72 | 46-73 | 46-74 | 46-75 | 46-76 |
| 46-77 | 46-78 | 46-79 | 46-80 | 46-81 | 46-82 | 46-83 | 46-84 | 46-85 | 46-86 | 46-87 |
| 46-88 | 46-89 | 46-90 | 46-91 | 46-92 | 47-1 | 47-2 | 47-3 | 47-4 | 47-5 | 47-6 |
| 47-7 | 47-8 | 47-9 | 47-10 | 47-11 | 47-12 | 47-13 | 47-14 | 47-15 | 47-16 | 47-17 |
| 47-18 | 47-19 | 47-20 | 47-21 | 47-22 | 47-23 | 47-70 | 47-71 | 47-72 | 47-73 | 47-74 |
| 47-75 | 47-76 | 47-77 | 47-78 | 47-79 | 47-80 | 47-81 | 47-82 | 47-83 | 47-84 | 47-85 |
| 47-86 | 47-87 | 47-88 | 47-89 | 47-90 | 47-91 | 47-92 | 48-1 | 48-2 | 48-3 | 48-4 |
| 48-5 | 48-6 | 48-7 | 48-8 | 48-9 | 48-10 | 48-11 | 48-12 | 48-13 | 48-14 | 48-15 |
| 48-16 | 48-17 | 48-18 | 48-19 | 48-20 | 48-21 | 48-22 | 48-23 | 48-70 | 48-71 | 48-72 |
| 48-73 | 48-74 | 48-75 | 48-76 | 48-77 | 48-78 | 48-79 | 48-80 | 48-81 | 48-82 | 48-83 |
| 48-84 | 48-85 | 48-86 | 48-87 | 48-88 | 48-89 | 48-90 | 48-91 | 48-92 | 48-93 | 48-94 |

TABLE 50

| Cmpd. | R² | R¹⁶ | R¹⁷ |
|---|---|---|---|
| 1 | 3-Cl, 5-Cl | Me | Me |
| 2 | 3-Cl, 5-Cl | Et | Me |
| 3 | 3-Cl, 5-Cl | n-Pr | Me |
| 4 | 3-Cl, 5-Cl | Et | Et |
| 5 | 3-Cl, 5-Cl | i-Pr | i-Pr |
| 6 | 3-Br, 5-Br | Me | Me |
| 7 | 3-Br, 5-Br | Et | Me |
| 8 | 3-Br, 5-Br | n-Pr | Me |
| 9 | 3-Br, 5-Br | Et | Et |
| 10 | 3-Br, 5-Br | i-Pr | i-Pr |
| 11 | 3-Cl, 4-Cl, 5-Cl | Me | Me |
| 12 | 3-Cl, 4-Cl, 5-Cl | Et | Me |
| 13 | 3-Cl, 4-Cl, 5-Cl | n-Pr | Me |
| 14 | 3-Cl, 4-Cl, 5-Cl | Et | Et |
| 15 | 3-Cl, 4-Cl, 5-Cl | i-Pr | i-Pr |
| 16 | 3-Cl, 4-F, 5-Cl | Me | Me |
| 17 | 3-Cl, 4-F, 5-Cl | Et | Me |
| 18 | 3-Cl, 4-F, 5-Cl | n-Pr | Me |
| 19 | 3-Cl, 4-F, 5-Cl | Et | Et |
| 20 | 3-Cl, 4-F, 5-Cl | i-Pr | i-Pr |
| 21 | 3-Cl | Me | Me |
| 22 | 3-Cl | Et | Me |
| 23 | 3-Cl | n-Pr | Me |
| 24 | 3-Cl | Et | Et |
| 25 | 3-Cl | i-Pr | i-Pr |
| 26 | 3-Br | Me | Me |
| 27 | 3-Br | Et | Me |
| 28 | 3-Br | n-Pr | Me |
| 29 | 3-Br | Et | Et |
| 30 | 3-Br | i-Pr | i-Pr |
| 31 | 3-CF₃, 5-CF₃ | Me | Me |
| 32 | 3-CF₃, 5-CF₃ | Me | Me |
| 33 | 3-CF₃, 5-CF₃ | n-Pr | Me |
| 34 | 3-CF₃, 5-CF₃ | Et | Et |
| 35 | 3-CF₃, 5-CF₃ | i-Pr | i-Pr |
| 36 | 3-CF₃, 5-Cl | Me | Me |
| 37 | 3-CF₃, 5-Cl | Et | Me |
| 38 | 3-CF₃, 5-Cl | n-Pr | Me |
| 39 | 3-CF₃, 5-Cl | Et | Et |
| 40 | 3-CF₃, 5-Cl | i-Pr | i-Pr |
| 41 | 3-CF₃, 5-Br | Me | Me |
| 42 | 3-CF₃, 5-Br | Et | Me |
| 43 | 3-CF₃, 5-Br | n-Pr | Me |
| 44 | 3-CF₃, 5-Br | Et | Et |
| 45 | 3-CF₃, 5-Br | i-Pr | i-Pr |
| 46 | 3-Cl, 4-CN, 5-Cl | Me | Me |
| 47 | 3-Cl, 4-CN, 5-Cl | Et | Me |
| 48 | 3-Cl, 4-CN, 5-Cl | n-Pr | Me |
| 49 | 3-Cl, 4-CN, 5-Cl | Et | Et |
| 50 | 3-Cl, 4-CN, 5-Cl | i-Pr | i-Pr |
| 51 | 3-Cl, 4-Me, 5-Cl | Me | Me |
| 52 | 3-Cl, 4-Me, 5-Cl | Et | Me |
| 53 | 3-Cl, 4-Me, 5-Cl | n-Pr | Me |
| 54 | 3-Cl, 4-Me, 5-Cl | Et | Et |
| 55 | 3-Cl, 4-Me, 5-Cl | i-Pr | i-Pr |
| 56 | 3-CF₃ | Me | H |
| 57 | 3-CF₃ | Me | C(=O)CF₃ |
| 58 | 3-CF₃ | Me | CN |
| 59 | 3-CF₃ | Et | H |
| 60 | 3-CF₃ | Et | C(=O)CF₃ |

TABLE 51

| Cmpd. | R² | R¹⁹ | R²⁰ |
|---|---|---|---|
| 1 | 3-Cl, 5-Cl | Me | H |
| 2 | 3-Cl, 5-Cl | Me | C(=O)CF₃ |
| 3 | 3-Cl, 5-Cl | Me | CN |
| 4 | 3-Cl, 5-Cl | Et | H |
| 5 | 3-Cl, 5-Cl | Et | C(=O)CF₃ |
| 6 | 3-Br, 5-Br | Me | H |
| 7 | 3-Br, 5-Br | Me | C(=O)CF₃ |
| 8 | 3-Br, 5-Br | Me | CN |
| 9 | 3-Br, 5-Br | Et | H |
| 10 | 3-Br, 5-Br | Et | C(=O)CF₃ |
| 11 | 3-Cl, 4-Cl, 5-Cl | Me | H |
| 12 | 3-Cl, 4-Cl, 5-Cl | Me | C(=O)CF₃ |
| 13 | 3-Cl, 4-Cl, 5-Cl | Me | CN |
| 14 | 3-Cl, 4-Cl, 5-Cl | Et | H |
| 15 | 3-Cl, 4-Cl, 5-Cl | Et | C(=O)CF₃ |
| 16 | 3-Cl, 4-F, 5-Cl | Me | H |
| 17 | 3-Cl, 4-F, 5-Cl | Me | C(=O)CF₃ |
| 18 | 3-Cl, 4-F, 5-Cl | Me | CN |
| 19 | 3-Cl, 4-F, 5-Cl | Et | H |
| 20 | 3-Cl, 4-F, 5-Cl | Et | C(=O)CF₃ |
| 21 | 3-Cl | Me | H |
| 22 | 3-Cl | Me | C(=O)CF₃ |
| 23 | 3-Cl | Me | CN |
| 24 | 3-Cl | Et | H |
| 25 | 3-Cl | Et | C(=O)CF₃ |
| 26 | 3-Br | Me | H |
| 27 | 3-Br | Me | C(=O)CF₃ |
| 28 | 3-Br | Me | CN |
| 29 | 3-Br | Et | H |
| 30 | 3-Br | Et | C(=O)CF₃ |
| 31 | 3-CF₃, 5-CF₃ | Me | H |
| 32 | 3-CF₃, 5-CF₃ | Me | C(=O)CF₃ |
| 33 | 3-CF₃, 5-CF₃ | Me | CN |
| 34 | 3-CF₃, 5-CF₃ | Et | H |
| 35 | 3-CF₃, 5-CF₃ | Et | C(=O)CF₃ |
| 36 | 3-CF₃, 5-Cl | Me | C(O)CF₃ |
| 37 | 3-CF₃, 5-Cl | Me | CN |
| 38 | 3-CF₃, 5-Cl | Me | H |
| 39 | 3-CF₃, 5-Cl | Et | C(O)CF₃ |
| 40 | 3-CF₃, 5-Cl | Et | i-Pr |
| 41 | 3-CF₃, 5-Br | Me | Me |
| 42 | 3-CF₃, 5-Br | Me | C(=O)CF₃ |
| 43 | 3-CF₃, 5-Br | Me | CN |
| 44 | 3-CF₃, 5-Br | Et | H |
| 45 | 3-CF₃, 5-Br | Et | C(=O)CF₃ |
| 46 | 3-Cl, 4-CN, 5-Cl | Me | H |
| 47 | 3-Cl, 4-CN, 5-Cl | Me | C(=O)CF₃ |
| 48 | 3-Cl, 4-CN, 5-Cl | Me | CN |
| 49 | 3-Cl, 4-CN, 5-Cl | Et | H |
| 50 | 3-Cl, 4-CN, 5-Cl | Et | C(=O)CF₃ |
| 51 | 3-Cl, 4-Me, 5-Cl | Me | H |
| 52 | 3-Cl, 4-Me, 5-Cl | Me | C(=O)CF₃ |
| 53 | 3-Cl, 4-Me, 5-Cl | Me | CN |
| 54 | 3-Cl, 4-Me, 5-Cl | Et | H |
| 55 | 3-Cl, 4-Me, 5-Cl | Et | C(=O)CF₃ |
| 56 | 3-CF₃ | Me | H |
| 57 | 3-CF₃ | Me | C(=O)CF₃ |
| 58 | 3-CF₃ | Me | CN |
| 59 | 3-CF₃ | Et | H |
| 60 | 3-CF₃ | Et | C(O)CF₃ |

TABLE 52

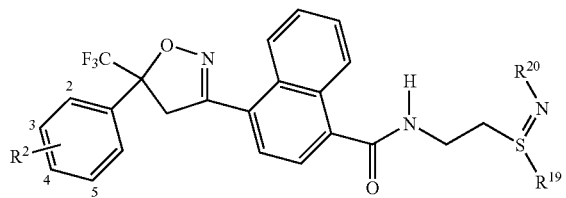

| Cmpd. | R² | R¹⁹ | R²⁰ |
|---|---|---|---|
| 1 | 3-Cl, 5-Cl | Me | H |
| 2 | 3-Cl, 5-Cl | Me | C(=O)CF₃ |
| 3 | 3-Cl, 5-Cl | Me | CN |
| 4 | 3-Cl, 5-Cl | Et | H |
| 5 | 3-Cl, 5-Cl | Et | C(=O)CF₃ |
| 6 | 3-Br, 5-Br | Me | H |
| 7 | 3-Br, 5-Br | Me | C(=O)CF₃ |
| 8 | 3-Br, 5-Br | Me | CN |
| 9 | 3-Br, 5-Br | Et | H |
| 10 | 3-Br, 5-Br | Et | C(=O)CF₃ |
| 11 | 3-Cl, 4-Cl, 5-Cl | Me | H |
| 12 | 3-Cl, 4-Cl, 5-Cl | Me | C(=O)CF₃ |
| 13 | 3-Cl, 4-Cl, 5-Cl | Me | CN |
| 14 | 3-Cl, 4-Cl, 5-Cl | Et | H |
| 15 | 3-Cl, 4-Cl, 5-Cl | Et | C(=O)CF₃ |
| 16 | 3-Cl, 4-F, 5-Cl | Me | H |
| 17 | 3-Cl, 4-F, 5-Cl | Me | C(=O)CF₃ |
| 18 | 3-Cl, 4-F, 5-Cl | Me | CN |
| 19 | 3-Cl, 4-F, 5-Cl | Et | H |
| 20 | 3-Cl, 4-F, 5-Cl | Et | C(=O)CF₃ |
| 21 | 3-Cl | Me | H |
| 22 | 3-Cl | Me | C(=O)CF₃ |
| 23 | 3-Cl | Me | CN |
| 24 | 3-Cl | Et | H |
| 25 | 3-Cl | Et | C(=O)CF₃ |
| 26 | 3-Br | Me | H |
| 27 | 3-Br | Me | C(=O)CF₃ |
| 28 | 3-Br | Me | CN |
| 29 | 3-Br | Et | H |
| 30 | 3-Br | Et | C(=O)CF₃ |
| 31 | 3-CF₃, 5-CF₃ | Me | H |
| 32 | 3-CF₃, 5-CF₃ | Me | C(=O)CF₃ |
| 33 | 3-CF₃, 5-CF₃ | Me | CN |
| 34 | 3-CF₃, 5-CF₃ | Et | H |
| 35 | 3-CF₃, 5-CF₃ | Et | C(=O)CF₃ |
| 36 | 3-CF₃, 5-Cl | Me | C(O)CF₃ |
| 37 | 3-CF₃, 5-Cl | Me | CN |
| 38 | 3-CF₃, 5-Cl | Me | H |
| 39 | 3-CF₃, 5-Cl | Et | C(O)CF₃ |
| 40 | 3-CF₃, 5-Cl | Et | i-Pr |
| 41 | 3-CF₃, 5-Br | Me | H |
| 42 | 3-CF₃, 5-Br | Me | C(=O)CF₃ |
| 43 | 3-CF₃, 5-Br | Me | CN |
| 44 | 3-CF₃, 5-Br | Et | H |
| 45 | 3-CF₃, 5-Br | Et | C(=O)CF₃ |
| 46 | 3-Cl, 4-CN, 5-Cl | Me | H |
| 47 | 3-Cl, 4-CN, 5-Cl | Me | C(=O)CF₃ |
| 48 | 3-Cl, 4-CN, 5-Cl | Me | CN |
| 49 | 3-Cl, 4-CN, 5-Cl | Et | H |
| 50 | 3-Cl, 4-CN, 5-Cl | Et | C(=O)CF₃ |
| 51 | 3-Cl, 4-Me, 5-Cl | Me | H |
| 52 | 3-Cl, 4-Me, 5-Cl | Me | C(=O)CF₃ |
| 53 | 3-Cl, 4-Me, 5-Cl | Me | CN |
| 54 | 3-Cl, 4-Me, 5-Cl | Et | H |
| 55 | 3-Cl, 4-Me, 5-Cl | Et | C(=O)CF₃ |
| 56 | 3-CF₃ | Me | H |
| 57 | 3-CF₃ | Me | C(=O)CF₃ |
| 58 | 3-CF₃ | Me | CN |
| 59 | 3-CF₃ | Et | H |
| 60 | 3-CF₃ | Et | C(O)CF₃ |

Formulation/Utility

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering, Dec.* 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-G. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

EXAMPLE A

| High Strength Concentrate | |
|---|---|
| Compound 4 | 98.5% |
| silica aerogel | 0.5% |
| synthetic amorphous fine silica | 1.0% |

EXAMPLE B

| Wettable Powder | |
|---|---|
| Compound 44 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

| Granule | |
|---|---|
| Compound 47 | 10.0% |
| attapulgite granules (low volatile matter, 0.71/0.30 mm; U.S.S. No. 25-50 sieves) | 90.0% |

EXAMPLE D

| Extruded Pellet | |
|---|---|
| Compound 49 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

| Emulsifiable Concentrate | |
|---|---|
| Compound 50 | 10.0% |
| polyoxyethylene sorbitol hexoleate | 20.0% |
| $C_6$-$C_{10}$ fatty acid methyl ester | 70.0% |

EXAMPLE F

| Microemulsion | |
|---|---|
| Compound 45 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

| Seed Treatment | |
|---|---|
| Compound 66 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

EXAMPLE H

| Fertilizer Stick | |
|---|---|
| Compound 76 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Naupho eta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae. Also included are eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the *Termitidae* (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa*

Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii*

Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling silverleaf whitefly (*Bemisia argentifolii*). Of note is use of compounds of this invention for controlling western flower thrip (*Frankliniella occidentalis*). Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoptera frugiperda*).

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide or salt thereof, and an effective amount of at least one additional biologically active compound or agent and can further comprise at least one of surfactants, solid diluents or liquid diluents. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiocarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

One embodiment of biological agents for mixing with compounds of this invention include entomopathogenic bacteria such as *Bacillus thuringiensis*, and the encapsulated delta-endotoxins of *Bacillus thuringiensis* (e.g., Cellcap, MPV, MPVII); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole (see U.S. Pat. No. 6,747,047, PCT Publications WO 2003/015518 and WO 2004/067528) and flubendiamide (see U.S. Pat. No. 6,603,044); nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of invertebrate pests controlled beyond the spectrum controlled by the compound of Formula 1 alone.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Of note is a combination of a compound of Formula 1 with at least one other invertebrate pest control active ingredient. Of particular note is such a combination where the other invertebrate pest control active ingredient has a different site of action from the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but a different site of action. Contacting a plant genetically modified to express an invertebrate pest compound (e.g., protein) or the locus of the plant with a biologically effective amount of a compound of this invention can also provide a broader spectrum of plant protection and be advantageous for resistance management.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1, an N-oxide, or a salt thereof, (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
| --- | --- | --- |
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |

TABLE A-continued

| Invertebrate Pest Control Agent | Mode of Action or Chemical Class | Typical Weight Ratio |
|---|---|---|
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

The weight ratios of a compound, including a compound of Formula 1, an N-oxide or a salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a compound of Formula 1 (compound numbers refer to compounds in Index Table A) and an additional invertebrate pest control agent.

TABLE B

| Mixture No. | Comp. No. | and | Invertebrate Pest Control Agent |
|---|---|---|---|
| A-1 | 66 | and | Abamectin |
| A-2 | 66 | and | Acetamiprid |
| A-3 | 66 | and | Amitraz |
| A-4 | 66 | and | Avermectin |
| A-5 | 66 | and | Azadirachtin |
| A-6 | 66 | and | Beta-cyfluthrin |
| A-7 | 66 | and | Bifenthrin |
| A-8 | 66 | and | Buprofezin |
| A-9 | 66 | and | Cartap |
| A-10 | 66 | and | Chlorantraniliprole |
| A-11 | 66 | and | Chlorfenapyr |
| A-12 | 66 | and | Chlorpyrifos |
| A-13 | 66 | and | Clothianidin |
| A-14 | 66 | and | Cyfluthrin |
| A-15 | 66 | and | Cyhalothrin |
| A-16 | 66 | and | Cypermethrin |
| A-17 | 66 | and | Cyromazine |
| A-18 | 66 | and | Deltamethrin |
| A-19 | 66 | and | Dieldrin |
| A-20 | 66 | and | Dinotefuran |
| A-21 | 66 | and | Diofenolan |
| A-22 | 66 | and | Emamectin |
| A-23 | 66 | and | Endosulfan |
| A-24 | 66 | and | Esfenvalerate |
| A-25 | 66 | and | Ethiprole |
| A-26 | 66 | and | Fenothiocarb |
| A-27 | 66 | and | Fenoxycarb |
| A-28 | 66 | and | Fenvalerate |
| A-29 | 66 | and | Fipronil |
| A-30 | 66 | and | Flonicamid |
| A-31 | 66 | and | Flubendiamide |
| A-32 | 66 | and | Flufenoxuron |
| A-33 | 66 | and | Hexaflumuron |
| A-34 | 66 | and | Hydramethylnon |
| A-35 | 66 | and | Imidacloprid |
| A-36 | 66 | and | Indoxacarb |
| A-37 | 66 | and | Lambda-cyhalothrin |
| A-38 | 66 | and | Lufenuron |
| A-39 | 66 | and | Metaflumizone |
| A-40 | 66 | and | Methomyl |
| A-41 | 66 | and | Methoprene |

TABLE B-continued

| Mixture No. | Comp. No. | and | Invertebrate Pest Control Agent |
|---|---|---|---|
| A-42 | 66 | and | Methoxyfenozide |
| A-43 | 66 | and | Nitenpyram |
| A-44 | 66 | and | Nithiazine |
| A-45 | 66 | and | Novaluron |
| A-46 | 66 | and | Oxamyl |
| A-47 | 66 | and | Pymetrozine |
| A-48 | 66 | and | Pyrethrin |
| A-49 | 66 | and | Pyridaben |
| A-50 | 66 | and | Pyridalyl |
| A-51 | 66 | and | Pyriproxyfen |
| A-52 | 66 | and | Ryanodine |
| A-53 | 66 | and | Spinetoram |
| A-54 | 66 | and | Spinosad |
| A-55 | 66 | and | Spirodiclofen |
| A-56 | 66 | and | Spiromesifen |
| A-57 | 66 | and | Tebufenozide |
| A-58 | 66 | and | Thiacloprid |
| A-59 | 66 | and | Thiamethoxam |
| A-60 | 66 | and | Thiodicarb |
| A-61 | 66 | and | Thiosultap-sodium |
| A-62 | 66 | and | Tralomethrin |
| A-63 | 66 | and | Triazamate |
| A-64 | 66 | and | Triflumuron |
| A-65 | 66 | and | *Bacillus thuringiensis* |
| A-66 | 66 | and | *Bacillus thuringiensis* delta-endotoxin |
| A-67 | 66 | and | NPV (e.g., Gemstar) |
| B-1 | 76 | and | Abamectin |
| B-2 | 76 | and | Acetamiprid |
| B-3 | 76 | and | Amitraz |
| B-4 | 76 | and | Avermectin |
| B-5 | 76 | and | Azadirachtin |
| B-6 | 76 | and | Beta-cyfluthrin |
| B-7 | 76 | and | Bifenthrin |
| B-8 | 76 | and | Buprofezin |
| B-9 | 76 | and | Cartap |
| B-10 | 76 | and | Chlorantraniliprole |
| B-11 | 76 | and | Chlorfenapyr |
| B-12 | 76 | and | Chlorpyrifos |
| B-13 | 76 | and | Clothianidin |
| B-14 | 76 | and | Cyfluthrin |
| B-15 | 76 | and | Cyhalothrin |
| B-16 | 76 | and | Cypermethrin |
| B-17 | 76 | and | Cyromazine |
| B-18 | 76 | and | Deltamethrin |
| B-19 | 76 | and | Dieldrin |
| B-20 | 76 | and | Dinotefuran |
| B-21 | 76 | and | Diofenolan |
| B-22 | 76 | and | Emamectin |
| B-23 | 76 | and | Endosulfan |
| B-24 | 76 | and | Esfenvalerate |
| B-25 | 76 | and | Ethiprole |
| B-26 | 76 | and | Fenothiocarb |
| B-27 | 76 | and | Fenoxycarb |
| B-28 | 76 | and | Fenvalerate |
| B-29 | 76 | and | Fipronil |
| B-30 | 76 | and | Flonicamid |
| B-31 | 76 | and | Flubendiamide |
| B-32 | 76 | and | Flufenoxuron |
| B-33 | 76 | and | Hexaflumuron |
| B-34 | 76 | and | Hydramethylnon |
| B-35 | 76 | and | Imidacloprid |
| B-36 | 76 | and | Indoxacarb |
| B-37 | 76 | and | Lambda-cyhalothrin |
| B-38 | 76 | and | Lufenuron |
| B-39 | 76 | and | Metaflumizone |
| B-40 | 76 | and | Methomyl |
| B-41 | 76 | and | Methoprene |
| B-42 | 76 | and | Methoxyfenozide |
| B-43 | 76 | and | Nitenpyram |
| B-44 | 76 | and | Nithiazine |
| B-45 | 76 | and | Novaluron |
| B-46 | 76 | and | Oxamyl |
| B-47 | 76 | and | Pymetrozine |
| B-48 | 76 | and | Pyrethrin |
| B-49 | 76 | and | Pyridaben |
| B-50 | 76 | and | Pyridalyl |
| B-51 | 76 | and | Pyriproxyfen |
| B-52 | 76 | and | Ryanodine |
| B-53 | 76 | and | Spinetoram |
| B-54 | 76 | and | Spinosad |
| B-55 | 76 | and | Spirodiclofen |
| B-56 | 76 | and | Spiromesifen |
| B-57 | 76 | and | Tebufenozide |
| B-58 | 76 | and | Thiacloprid |
| B-59 | 76 | and | Thiamethoxam |
| B-60 | 76 | and | Thiodicarb |
| B-61 | 76 | and | Thiosultap-sodium |
| B-62 | 76 | and | Tralomethrin |
| B-63 | 76 | and | Triazamate |
| B-64 | 76 | and | Triflumuron |
| B-65 | 76 | and | *Bacillus thuringiensis* |
| B-66 | 76 | and | *Bacillus thuringiensis* delta-endotoxin |
| B-67 | 76 | and | NPV (e.g., Gemstar) |

The specific mixtures listed in Table B typically combine a compound of Formula 1 with the other invertebrate pest agent in the ratios specified in Table A.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment Progress and Prospects,* 1994 BCPC Monograph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease-transmitting pests include, for example, chiggers, ticks, lice, mosquitoes, flies, mites and fleas. Internal parasites include heartworms, hookworms and helminths. Compounds and compositions of the present invention are particularly suitable for combating external parasitic or disease-transmitting pests. Compounds and compositions of the present invention are suitable for systemic and/or non-systemic control of infestation or infection by parasites on animals.

Compounds and compositions of the present invention are suitable for combating parasites that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying a composition comprising a compound of the present invention allows more economic and simple husbandry of animals.

Compounds and compositions of the present invention are especially suitable for combating parasites that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffaloes, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Of particular note is the embodiment wherein the animals to be protected are domesticated dogs (i.e. *Canis lupus familiaris*) and domestic house cats (i.e. *Felis catus*).

Birds treated or protected by the inventive compounds can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws, and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of invertebrate parasitic pests controlled by administering a parasiticidally effective amount of a compound of this invention to an animal to be protected include ectoparasites (arthropods, acarines, etc) and endoparasites (helminths, e.g., nematodes, trematodes, cestodes, acanthocephalans, etc.).

The disease or group of diseases described generally as helminthiasis is due to infection of an animal host with parasitic worms known as helminths. The term "helminths" is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals. Nematodes that are contemplated to be treated by the compounds of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as Dictyocaulus are found in the lungs. Still other parasites may be located in other tissues such as the heart and blood vessels, subcutaneous and lymphatic tissue and the like.

Trematodes that are contemplated to be treated by the compounds of this invention and by the inventive methods include, without limitation, the following genera: *Alaria, Fasciola, Nanophyetus, Opisthorchis, Paragonimus* and *Schistosoma.*

Cestodes that are contemplated to be treated by the compounds of this invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongyloides, Trichinella, Capillaria, Trichuris* and *Enterobius.* Other medically important genera of parasites which are found in the blood or other tissues and organs outside the gastrointestinal tract are the filarial worms such as *Wuchereria, Brugia, Onchocerca* and *Loa,* as well as *Dracunculus* and extra intestinal stages of the intestinal worms *Strongyloides* and *Trichinella.*

Numerous other helminth genera and species are known to the art, and are also contemplated to be treated by the compounds of the invention. These are enumerated in great detail in *Textbook of Veterinary Clinical Parasitology, Volume 1, Helminths,* E. J. L. Soulsby, F. A. Davis Co., Philadelphia, Pa.; *Helminths, Arthropods and Protozoa,* (6$^{th}$ Edition of *Monnig's Veterinary Helminthology and Entomology*), E. J. L. Soulsby, The Williams and Wilkins Co., Baltimore, Md.

The compounds of Formula 1 are effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax,* the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmata* spp. e.g., mesostigmatids such as the chicken mite, *Dermanyssus gallinae*; itch or scab mites such as Sarcoptidae spp. for example, *Sarcoptes scabiei*; mange mites such as Psoroptidae spp. including *Chorioptes bovis* and *Psoroptes ovis*; chiggers e.g., Trombiculidae spp. for example the North American chigger, *Trombicula alfreddugesi.*

Ticks include, e.g., soft-bodied ticks including Argasidae spp. for example *Argas* spp. and *Ornithodoros* spp.; hard-bodied ticks including Ixodidae spp., for example *Rhipicephalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides fells*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); Triatominae spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in *Medical and Veterinary Entomology,* D. S. Kettle, John Wiley & Sons, New York and Toronto; *Control of Arthropod Pests of Livestock: A Review of Technology,* R. O. Drummand, J. E. George, and S. E. Kunz, CRC Press, Boca Raton, Fla.

It is also contemplated that the compounds and compositions of this invention may be effective against a number of protozoa endoparasites of animals, including those summarized by Table 1, as follows.

TABLE 1

Exemplary Parasitic Protozoa and Associated Human Diseases

| Phylum | Subphylum | Representative Genera | Human Disease or Disorder |
| --- | --- | --- | --- |
| Sarcomastigophora (with flagella, pseudopodia, or both) | Mastigophora (Flagella) | *Leishmania* | Visceral, cutaneous and mucocutaneous Infection |
| | | *Trypansoma* | Sleeping sickness Chagas' disease |
| | | *Giardia* | Diarrhea |
| | | *Trichomonas* | Vaginitis |
| | Sarcodina (pseudopodia) | *Entamoeba* | Dysentery, liver Abscess |
| | | *Dientamoeba* | Colitis |
| | | *Naegleria* and *Acanthamoeba* | Central nervous system and corneal ulcers |
| | | *Babesia* | Babesiesis |
| Apicomplexa (apical complex) | | *Plasmodium* | Malaria |
| | | *Isospora* | Diarrhea |
| | | *Sarcocystis* | Diarrhea |
| | | *Cryptosporidum* | Diarrhea |
| | | *Toxoplasma* | Toxoplasmosis |
| | | *Eimeria* | Chicken coccidiosis |
| Microspora | | *Enterocytozoon* | Diarrhea |
| Ciliaphora (with cilia) | | *Balantidium* | Dysentery |
| Unclassified | | *Pneumocystis* | Pneumonia |

In particular, the compounds of this invention are effective against ectoparasites including: flies such as *Haematobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Tri-*

*chodectes canis*; keds such as *Melophagus ovinus*; mites such as *Psoroptes* spp., *Sarcoptes scabei*, *Chorioptes bovis*, *Demodex equi*, *Cheyletiella* spp., *Notoedres cati*, *Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

Biologically active compounds or agents useful in the compositions of the present invention include the organophosphate pesticides. This class of pesticides has very broad activity as insecticides and, in certain instances, anthelmintic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. It is also contemplated to include combinations of the inventive methods and compounds with carbamate-type pesticides, including, e.g., carbaryl, carbofuran, aldicarb, molinate, methomyl, carbofuran, etc., as well as combinations with the organochlorine-type pesticides. It is further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *Bacillus thuringiensis*, chlorobenzilate, formamidines (e.g., amitraz), copper compounds (e.g., copper hydroxide and cupric oxychloride sulfate), cyfluthrin, cypermethrin, dicofol, endosulfan, esfenvalerate, fenvalerate, lambda-cyhalothrin, methoxychlor and sulfur.

Of note are additional biologically active compounds or agents selected from art-known anthelmintics, such as, for example, macrocyclic lactones (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), cyclic depsipeptides (e.g., emodepside), piperazine salts, nitroscanate and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the compositions of the present invention selected from the avermectin class of antiparasitic compounds. As stated above, the avermectin family of compounds includes very potent antiparasitic agents known to be useful against a broad spectrum of endoparasites and ectoparasites in mammals.

A preferred compound for use within the scope of the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. Ivermectin is disclosed in U.S. Pat. No. 4,199,569.

Abamectin is an avermectin that is disclosed as avermectin $B_{1a}/B_{1b}$ in U.S. Pat. No. 4,310,519. Abamectin contains at least 80% of avermectin $B_{1a}$ and not more than 20% of avermectin $B_{1b}$.

Another preferred avermectin is doramectin, also known as 25-cyclohexyl-avermectin $B_1$. The structure and preparation of doramectin is disclosed in U.S. Pat. No. 5,089,480.

Another preferred avermectin is moxidectin. Moxidectin, also known as LL-F28249 alpha, is known from U.S. Pat. No. 4,916,154.

Another preferred avermectin is selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a milbemycin-producing strain of *Streptomyces*. The microorganism, the fermentation conditions and the isolation procedures are described in U.S. Pat. Nos. 3,950,360 and 3,984,564.

Emamectin (4"-deoxy-4"-epi-methylaminoavermectin $B_1$), which can be prepared as described in U.S. Pat. Nos. 5,288,710 and 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the emamectin salt used in the present invention is emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds: imidazo[1,2-b]pyridazine compounds as described by U.S. Patent Application Publication No. 2005/0182059 A1; 1-(4-mono and di-halomethylsulphonylphenyl)-2-acylamino-3-fluoropropanol compounds, as described by U.S. Pat. No. 7,361,689; trifluoromethanesulfonanilide oxime ether derivatives, as described by U.S. Pat. No. 7,312,248; and n-[(phenyloxy)phenyl]-1,1,1-trifluoromethanesulfonamide and n-[(phenylsulfanyl)phenyl]-1,1,1-trifluoromethanesulfonamide derivatives, as described by PCT Patent Application Publication WO 2006/135648.

The compositions of the present invention may also further comprise a flukicide. Suitable flukicides include, for example, triclabendazole, fenbendazole, albendazole, clorsulon and oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed herein below.

One useful antibiotic is florfenicol, also known as D-(threo)-1-(4-methylsulfonylphenyl)-2-dichloroacetamido-3-fluoro-1-propanol. Another preferred antibiotic compound is D-(threo)-1-(4-methylsulfonylphenyl)-2-difluoro-acetamido-3-fluoro-1-propanol. Another useful antibiotic is thiamphenicol. Processes for the manufacture of these antibiotic compounds, and intermediates useful in such processes, are described in U.S. Pat. Nos. 4,31,857; 4,582,918; 4,973,750; 4,876,352; 5,227,494; 4,743,700; 5,567,844; 5,105,009; 5,382,673; 5,352,832; and 5,663,361. Other florfenicol analogs and/or prodrugs have been disclosed and such analogs also can be used in the compositions and methods of the present invention (see e.g., U.S. Pat. Nos. 7,041, 670 and 7,153,842).

Another useful antibiotic compound is tilmicosin. Tilmicosin is a macrolide antibiotic that is chemically defined as 20-dihydro-20-deoxy-20-(cis-3,5-dimethylpiperidin-1-yl)-desmycosin and is disclosed in U.S. Pat. No. 4,820,695.

Another useful antibiotic for use in the present invention is tulathromycin. Tulathromycin may be prepared in accordance with the procedures set forth in U.S. Pat. No. 6,825, 327.

Further antibiotics for use in the present invention include the cephalosporins such as, for example, ceftiofur, cefquinome, etc. The concentration of the cephalosporin in the formulation of the present invention optionally varies between about 1 mg/mL to 500 mg/mL.

Another useful antibiotic includes the fluoroquinolones, such as, for example, enrofloxacin, danofloxacin, difloxacin, orbifloxacin and marbofloxacin. In the case of enrofloxacin, it may be administered in a concentration of about 100 mg/mL. Danofloxacin may be present in a concentration of about 180 mg/mL.

Other useful macrolide antibiotics include compounds from the class of ketolides, or, more specifically, the azalides. Such compounds are described in, for example, U.S. Pat. Nos. 6,514,945; 6,472,371; 6,270,768; 6,437,151; 6,271,255; 6,239,12; 5,958,888; 6,339,063; and 6,054,434.

Other useful antibiotics include the tetracyclines, particularly chlortetracycline and oxytetracycline. Other antibiotics may include β-lactams such as penicillins, e.g., penicillin, ampicillin, amoxicillin, or a combination of amoxicillin with clavulanic acid or other beta lactamase inhibitors.

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present invention.

Any of the compounds of the present invention, or a suitable combination of such compounds, may be administered directly to the animal subject and/or indirectly by applying it to the local environment in which the animal dwells (such as bedding, enclosures, or the like). Direct administration includes contacting the skin, fur or feathers of a subject animal with the compounds, or by feeding or injecting the compounds into the animal.

The compounds of the present invention may be administered in a controlled release form, e.g., in a subcutaneous slow release formulation, or in the form of a controlled release device affixed to an animal such as a flea collar. Collars for the controlled release of an insecticide agent for long term protection against flea infestation in a companion animal are art-known, and are described, for example, by U.S. Pat. Nos. 3,852,416; 4,224,901; 5,555,848; and 5,184,573.

Typically a parasiticidal composition according to the present invention comprises a mixture of a compound of Formula 1 with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a compound of the invention (i.e. in a parasiticidally effective amount) and at least one veterinarily acceptable carrier.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. The compounds of the present invention may also be formulated for bolus injection or continuous infusion. Pharmaceutical compositions for injection include aqueous solutions preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the present invention may also be formulated as a depot preparation. Such long acting formulations may be administered by implantation (for example, subcutaneously or intramuscularly) or by intramuscular or subcutaneous injection. The compounds of the present invention may be formulated for this route of administration with suitable polymeric or hydrophobic materials (e.g., in an emulsion with a pharmacologically acceptable oil).

For administration by inhalation, the compounds of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compounds of the present invention have been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

A preferred embodiment is a composition formulated into a chewable and/or edible product (e.g., a chewable treat or edible tablet). Such a product would ideally have a taste, texture and/or aroma favored by the animal to be protected so as to facilitate oral administration of the compound of Formula 1.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 may also be formulated in rectal compositions such as suppositories or retention enemas, using, e.g., conventional suppository bases such as cocoa butter or other glycerides.

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Carriers in such formulations include propylene glycol, paraffins, aromatics, esters such as isopropyl myristate, glycol ethers, alcohols such as ethanol, n-propanol, 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of $C_{12}$-$C_{18}$ chain length; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a crystallization inhibitor or a dispersant known from the pharmaceutical or cosmetic industry also to be present.

A pour-on formulation may also be prepared for control of parasites in an animal of agricultural value. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is used. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations of this invention are prepared according to known techniques. When the pour-on formulation is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. If the pour-on formulation is an emulsion or suspension, the formulations can be similarly prepared using known techniques.

Other delivery systems for relatively hydrophobic pharmaceutical compounds can be employed. Liposomes and emulsions are well-known examples of delivery vehicles or carriers for hydrophobic drugs. In addition, organic solvents such as dimethylsulfoxide can be used, if needed.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1 is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral, subcutaneous or spot-on administration to homeothermic animals, a dose of a compound of the present invention administered at suitable intervals typically ranges from about 0.01 mg/kg to about 100 mg/kg, and preferably from about 0.01 mg/kg to about 30 mg/kg of animal body weight. For other topical (e.g., dermal) administration, including dips and sprays, a dose typically contains from about 0.01 ppm to about 150,000 ppm, more typically from about 0.01 ppm to about 100,000 ppm, preferably from about 0.01 ppm to about 5,000 ppm, and most preferably from about 0.01 ppm to about 3,000 ppm, of a compound of the present invention.

Suitable intervals for the administration of compounds of the present invention to homeothermic animals range from about daily to about yearly. Of note are administration intervals ranging from about weekly to about once every 6 months. Of particular note are monthly administration intervals (i.e. administering the compound to the animal once every month).

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-G for compound descriptions. See Index Table H for $^1$H NMR data. For mass spectral data, the numerical value reported is the molecular weight of the highest isotopic abundance parent ion (M+1) formed by addition of H$^+$ (molecular weight of 1) to the molecule, observed by mass spectrometry using atmospheric pressure chemical ionization (AP$^+$). The following abbreviations are used in the Index Tables which follow: Cmpd means Compound, t is tertiary, c is cyclo, Me is methyl, Et is ethyl, Pr is propyl, i-Pr is isopropyl, Bu is butyl, c-Pr is cyclopropyl, c-Pn is cyclopentyl, c-Hx is cyclohexyl, t-Bu is tertiary-butyl, Ph is phenyl, OMe is methoxy, SMe is methylthio, and SO$_2$Me means methylsulfonyl. (R) or (S) denotes the absolute chirality of the asymmetric carbon center. The variable "R$^2$" represents one or a combination of substituents as listed in the Index Tables. The abbreviation "Ex." stands for "Example" and is followed by a number indicating in which example the compound is prepared.

INDEX TABLE A

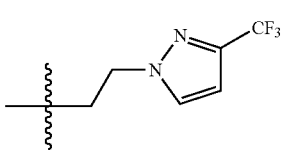

| Cmpd | R$^2$ | R | m.p. (° C.) or AP$^+$ (M + 1) |
|---|---|---|---|
| 1 | 3-Cl, 5-Cl | CH$_2$CH$_2$NH(C=O)O-t-Bu | * |
| 2 | 3-Cl, 5-Cl | (CH$_2$)$_6$NH(C=O)O-t-Bu | * |
| 3 | 3-Cl, 5-Cl | (CH$_2$)$_3$NMe(C=O)O-t-Bu | * |
| 4 | 3-Cl, 5-Cl | (CH$_2$)$_3$NMe(C=O)Me | * |
| 5 | 3-Cl, 5-Cl | (S)-CH(Ph)CO$_2$H | * |
| 6 | 3-Cl, 5-Cl | C(Me)$_2$CO$_2$H | * |
| 7 | 3-Cl, 5-Cl | CH$_2$CH$_2$CO$_2$H | * |
| 8 | 3-Cl, 4-Cl, 5-Cl | CH$_2$CO$_2$H | * |
| 9 | 3-Br, 5-Br | CH$_2$CO$_2$H | * |
| 10 | 3-Cl, 5-Cl | SO$_2$Me | * |
| 11 | 3-Cl, 5-Cl | SO$_2$Ph | * |
| 12 | 3-Cl, 5-Cl | CH$_2$CO$_2$H | * |
| 13 | 3-Cl, 5-Cl | CH$_2$CO$_2$Na | * |
| 14 | 3-Cl, 5-Cl | CH$_2$CH(Cl)CH$_2$CH$_2$CH$_2$Cl | * |
| 15 | 3-CF$_3$, 5-CF$_3$ | CH$_2$CO$_2$H | * |
| 16 | 3-CF$_3$ | CH(Et)CH$_2$OH | |
| 17 | 3-CF$_3$ | (pyrazolyl-CF$_3$ group) | * |

INDEX TABLE A-continued

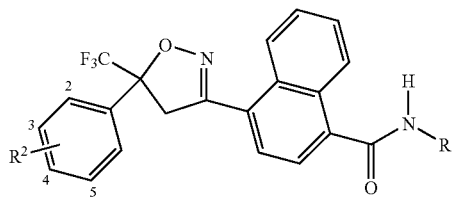

| Cmpd | R² | R | m.p. (° C.) or AP⁺ (M + 1) |
|---|---|---|---|
| 18 | 3-CF₃ | (1,2,4-triazol-1-yl-ethyl group) | * |
| 19 | 3-CF₃ | (2,2-dimethyl-1,3-dioxolan-4-yl-methyl group) | * |
| 20 | 3-CF₃ | (tetrahydrofuran-2-yl-methyl group) | * |
| 21 | 3-CF₃ | (CH₂)₃SCH₂CF₃ | 609 |
| 22 | 3-CF₃ | (CH₂)₃SCH₂CF₃ | 594 |
| 23 | 3-Br, 5-CF₃ | CH₂CO₂H | * |
| 24 | 3-CF₃ | (3-(trifluoromethyl)pyrazol-1-yl-propyl group) | 629 |
| 25 | 3-CF₃, 5-CF₃ | CH₂C(=O)ON=C(CH₃)₂ | * |
| 26 | 3-Cl, 5-CF₃ | CH₂CO₂H | * |
| 27 | 3-CF₃, 5-CF₃ | (tetrahydrofuran-2-yl-methyl group) | * |
| 28 | 3-F, 5-F | CH₂CO₂H | 187-190 |
| 29 | 3-F | CH₂CO₂H | 182-184 |
| 30 | 3-Br | CH₂CO₂H | * |
| 31 | 3-CF₃, 5-CF₃ | CH(CH₃)COOH | 118-119 |
| 32 | 3-Cl, 5-CF₃ | (R)-CH(CH₃)COOH | * |
| 34 | 3-Cl, 5-OCF₃ | CH₂CO₂H | * |
| 35 | 3-Cl, 5-OCF₃ | (R)-CH(CH₃)COOH | * |
| 36 | 3-Cl, 5-OCH₂CF₃ | CH₂CO₂H | * |
| 37 | 3-Cl, 5-OCH₂CF₃ | (R)-CH(CH₃)COOH | * |
| 38 | 3-Br, 5-CF₃ | (R)-CH(CH₃)COOH | * |
| 39 | 3-CF₃, 5-CF₃ | (R)-CH(i-Pr)COOH | |
| 40 | 3-F, 5-CF₃ | (R)-CH(CH₃)COOH | * |
| 41 | 3-CF₃, 5-CF₃ | (R)-CH(CH₃)COOH | 593 |
| 88 | 3-Cl, 5-CF₃ | CH(Et)COOH | |

* See Index Table H for ¹H NMR data.

INDEX TABLE B

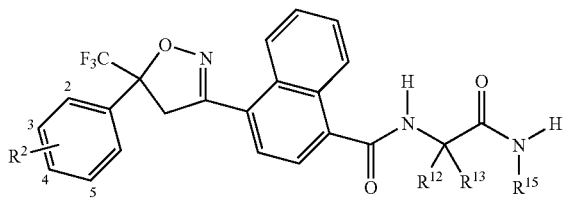

| Cmpd | R² | R¹² | R¹³ | R¹⁵ | m.p. (° C.) |
|---|---|---|---|---|---|
| 42 | 3-Cl, 5-Cl | H | H | (CH₂)₃NHMe | * |
| 43 | 3-Cl, 5-Cl | CH₃ | CH₃ | CH₂-c-Pr | * |
| 44 (Ex. 2) | 3-Cl, 5-Cl | H | H | CH₂-c-Pr | ** |
| 45 | 3-Cl, 5-Cl | H | H | CH₂-2-Py | * |
| 46 | 3-Cl, 5-Cl | H | H | C₆H₄-4-CF₃ | * |
| 47 (Ex. 1) | 3-Cl, 5-Cl | H | H | CH₂CH₂OCH₃ | ** |
| 48 | 3-Cl, 5-Cl | H | H | CH₂CH₂SCH₃ | * |
| 49 | 3-Cl, 4-Cl, 5-Cl | H | H | CH₂CH₂SCH₃ | * |
| 50 | 3-Cl, 5-Cl | H | H | c-Pr | * |
| 51 | 3-Cl, 5-Cl | H | H | c-Hx | * |
| 52 | 3-Cl, 5-Cl | H | H | c-Pn | * |
| 53 | 3-Cl, 5-Cl | H | (R)-CH₃ | c-Pr | * |
| 54 | 3-CF₃ | H | H | c-Pr | * |
| 55 | 3-CF₃, 5-CF₃ | H | H | c-Pr | * |
| 56 | 3-Br | H | H | CH₂-c-Pr | * |
| 57 | 3-Br | H | H | CH₂CH₂SCH₃ | * |
| 58 | 3-OCF₃ | H | H | CH₂COOH | * |
| 59 | 3-OCF₃ | H | H | CH₂-2-Py | * |
| 60 | 3-OCF₃ | H | H | CH₂-c-Pr | * |
| 61 | 3-OCF₃ | H | H | CH₂CH₂SCH₃ | * |
| 62 | 3-F, 5-F | H | H | c-Pr | * |
| 63 | 3-F | H | H | c-Pr | * |
| 64 | 3-CF₃, 5-CF₃ | H | (R)-CH₃ | c-Pr | * |
| 65 | 3-CF₃, 5-CF₃ | H | (R)-CH₃ | H | * |
| 66 | 3-CF₃, 5-CF₃ | H | (R)-CH₃ | CH₂-c-Pr | * |
| 67 | 3-CF₃, 5-CF₃ | H | CH₃ | c-Pr | 115-116 |
| 68 | 3-CF₃, 5-CF₃ | H | CH₃ | CH₂-c-Pr | 114-115 |
| 69 | 3-CF₃, 5-CF₃ | H | CH₃ | H | 113-114 |
| 70 | 3-CF₃, 5-CF₃ | H | H | H | * |
| 71 | 3-CF₃, 5-CF₃ | H | H | CH₂-c-Pr | * |
| 72 | 3-Cl, 5-CF₃ | H | (R)-CH₃ | c-Pr | * |
| 73 | 3-Cl, 5-CF₃ | H | (R)-CH₃ | CH₂-c-Pr | * |
| 74 | 3-Cl, 5-CF₃ | H | (R)-CH₃ | H | * |
| 75 | 3-Cl, 5-CF₃ | H | H | c-Pr | 133-134 |
| 76 | 3-Cl, 5-CF₃ | H | H | CH₂-c-Pr | 92-93 |
| 77 | 3-Cl, 5-CF₃ | H | H | H | 99-100 |
| 78 | 3-Cl, 5-CF₃ | H | CH₃ | c-Pr | 120-121 |
| 79 | 3-Cl, 5-CF₃ | H | CH₃ | CH₂-c-Pr | 94-95 |
| 80 | 3-CF₃, 5-CF₃ | H | (R)-CH₃ | ⸺CH₂-cyclopropyl-CF₂ | * |
| 81 | 3-Cl, 5-OCF₃ | H | H | CH₂-c-Pr | * |
| 82 | 3-Cl, 5-OCF₃ | H | H | c-Pr | * |
| 83 | 3-Br, 5-CF₃ | H | (R)-CH₃ | H | * |
| 84 | 3-Cl, 5-OCH₂CF₃ | H | H | CH₂-c-Pr | * |
| 85 | 3-Cl, 5-OCH₂CF₃ | H | H | c-Pr | * |
| 86 | 3-Cl, 5-CF₃ | H | (R)-Et | H | * |
| 87 | 3-Cl, 5-CF₃ | H | (R)-i-Pr | H | * |

\* See Index Table H for ¹H NMR data.
\*\* See synthesis example for ¹H NMR data.

INDEX TABLE C

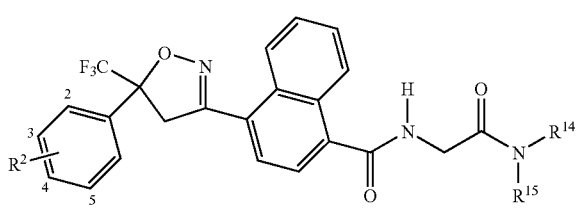

| Cmpd | R² | R¹⁴/R¹⁵ | m.p. (° C.) |
|---|---|---|---|
| 89 | 3-Cl, 5-Cl | —(CH₂)₅— | * |
| 90 | 3-Cl, 5-Cl | —(CH₂CF₂CH₂CH₂)— | * |
| 91 | 3-Cl, 5-Cl | —(CH(CF₃)CH₂CH₂CH₂)— | * |
| 92 | 3-CF₃ | —(CH₂CH₂N(SO₂Et)CH₂CH₂)— | * |

* See Index Table H for ¹H NMR data.

INDEX TABLE D

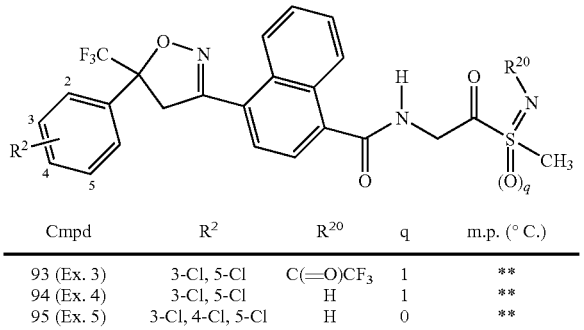

| Cmpd | R² | R²⁰ | q | m.p. (° C.) |
|---|---|---|---|---|
| 93 (Ex. 3) | 3-Cl, 5-Cl | C(=O)CF₃ | 1 | ** |
| 94 (Ex. 4) | 3-Cl, 5-Cl | H | 1 | ** |
| 95 (Ex. 5) | 3-Cl, 4-Cl, 5-Cl | H | 0 | ** |

** See synthesis example for ¹H NMR data.

INDEX TABLE E

| Cmpd | R² | R¹⁶ | R¹⁷ | m.p. (° C.) |
|---|---|---|---|---|
| 96 (Ex. 6) | 3-Cl, 5-Cl | Me | Me | ** |

** See synthesis example for ¹H NMR data.

INDEX TABLE F

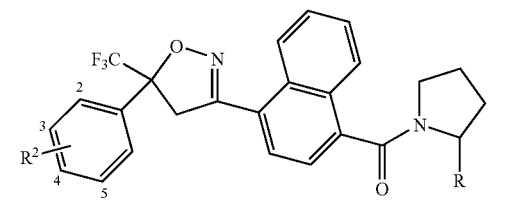

| Cmpd | R² | R | m.p. (° C.) |
|---|---|---|---|
| 97 | 3-Cl, 5-Cl | (S)-CO₂CH₃ | * |
| 98 | 3-Cl, 5-Cl | (R)-CO₂CH₃ | * |
| 99 | 3-Cl, 5-Cl | (S)-CO₂H | * |
| 100 | 3-Cl, 5-Cl | (R)-CO₂H | * |
| 101 | 3-Cl, 5-Cl | (S)-C(=O)NHCH₂CF₃ | * |
| 102 | 3-Cl, 5-Cl | (R)-C(=O)NHCH₂CF₃ | * |
| 103 | 3-Cl, 5-Cl | (S)-C(=O)NHCH₃ | * |
| 104 | 3-Cl, 5-Cl | (R)-C(=O)NHCH₃ | * |
| 105 | 3-Cl, 5-Cl | (S)-C(=O)NHCH₂CH₃ | * |
| 106 | 3-Cl, 5-Cl | (R)-C(=O)NHCH₂CH₃ | * |

* See Index Table H for ¹H NMR data.

INDEX TABLE G

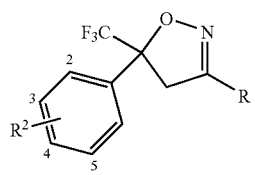

| Cmpd | R² | R | m.p. (° C.) |
|---|---|---|---|
| 107 | 3-Cl, 5-Cl | 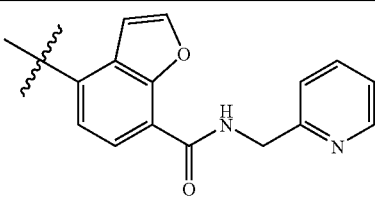 | * |
| 108 | 3-Cl, 5-Cl | 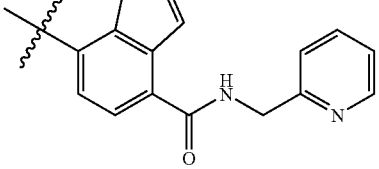 | * |

INDEX TABLE G-continued

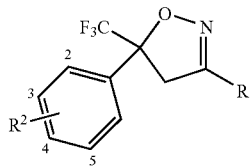

| Cmpd | R² | R | m.p. (° C.) |
|---|---|---|---|
| 109 | 3-Cl, 5-Cl | (1-methylindole-7-yl with 4-C(O)NH-CH₂-2-pyridyl) | * |
| 110 | 3-CF₃, 5-CF₃ | (1H-indazol-7-yl with 4-C(O)NH-CH₂-cyclopropyl) | * |
| 111 | 3-Cl, 5-Cl | (1-methylindole-7-yl with 4-C(O)NH-CH₂CH₂-S(O)CH₃) | * |

* See Index Table H for ¹H NMR data.

INDEX TABLE H

| Compound | ¹H NMR Data (CDCl₃ solution unless indicated otherwise)[a] |
|---|---|
| 1 | δ 8.79 (d, 1H), 8.32 (d, 1H), 7.43-7.65 (m, 7H), 6.90 (br s, 1H), 5.04 (br s, 1H), 4.25 (d, 1H), 3.89 (d, 1H), 3.64 (m, 2H), 3.43 (m, 2H), 1.40 (s, 9H). |
| 2 | δ 8.80 (d, 1H), 8.25 (d, 1H), 7.45-7.66 (m, 7H), 6.31 (br s, 1H), 4.56 (br s, 1H), 4.24 (d, 1H), 3.89 (d, 1H), 3.52 (m, 2H), 3.11 (m, 2H), 1.40-1.69 (m, 8H), 1.40 (s, 9H). |
| 3 | δ 8.80 (d, 1H), 8.35 (d, br., 1H), 7.45-7.65 (m, 8H), 4.25 (d, 1H), 3.90 (d, 1H), 3.50 (m, 2H), 3.38 (m, 2H), 2.86 (s, 3H), 1.84 (m, 2H), 1.37 (s, 9H). |
| 4 | δ 8.81 (d, 1H), 8.36 (d, 1H), 7.44-7.64 (m H), 4.24 (d, 1H), 3.89 (d, 1H), 3.50 (m, 2H), 3.43 (m, 2H), 3.01 (s, 3H), 2.04 (s, 3H), 1.84 (m, 2H). |
| 5 | δ 8.70 (m, 1H), 8.14 (m, 1H), 8.04 (br s, 1H), 7.29-7.55 (m, 12H), 7.17 (m, 1H), 5.81 (d, 1H), 4.15 (d, 1H), 3.80 (d, 1H). |
| 6 | δ (CD₃C(=O)CD₃) 8.89 (d, 1H), 8.42 (d, 1H), 7.99 (br s, 1H), 7.86 (d, 1H), 7.61-7.74 (m, 6H), 4.59 (d, 1H), 4.47 (d, 1H), 1.67 (s, 6H). |
| 7 | δ 8.78 (d, 1H), 8.24 (d, 1H), 7.44-7.64 (m, 7H), 6.61 (t, 1H), 4.23 (d, 1H), 3.87 (d, 1H), 3.80 (q, 2H), 2.77 (m, 1H). |
| 8 | δ 8.76 (d, 1H), 8.27 (d, 1H), 7.68 (s, 2H), 7.59 (m, 2H), 7.54 (d, 1H), 7.40 (d, 1H), 6.74 (t, 1H), 4.32 (d, 2H), 4.22 (d, 1H), 3.85 (d, 1H). |
| 9 | δ 10.41 (br s, 1H), 8.71 (d, 1H), 8.20 (d, 1H), 7.48-7.75 (m, 5H), 7.44 (d, 1H), 7.31 (d, 1H), 6.92 (br s, 1H), 4.26 (d, 2H), 4.17 (d, 1H), 3.83 (d, 1H). |
| 10 | (CD₃S(=O)CD₃) δ 8.80 (d, 1H), 8.35 (dd, 1H), 7.95 (d, 1H), 7.80-7.90 (m, 2H), 7.60-7.75 (m, 4H), 4.56 (s, 2H), 3.37 (s, 3H). |
| 11 | (CD₃C(=O)CD₃) δ 8.86 (d, 1H), 8.32 (d, 1H), 8.08-8.24 (m, 2H), 7.76-7.93 (m, 4H), 7.44-7.76 (m, 6H), 4.57 (d, 1H), 4.45 (d, 1H). |
| 12 | (CD₃S(=O)CD₃) δ 9.02 (t, 1H), 8.81 (d, 1H), 8.37 (d, 1H), 7.92 (d, 1H), 7.83 (t, 1H), 7.65-7.74 (m, 5H), 4.58 (d, 1H), 4.54 (d, 1H), 4.02 (d, 2H). |
| 13 | (CD₃S(=O)CD₃) δ 8.86 (d, 1H), 8.50 (d, 1H), 7.67-7.96 (m, 8H), 4.61 (apparent s, 2H), 3.64 (d, 2H). |
| 14 | δ 8.77 (d, 1H), 8.25 (d, 1H), 7.40-7.64 (m, H), 6.63 (br t, 1H), 4.23 (m, 2H), 4.00 (m, 1H), 3.87 (d, 1H), 3.61 (m, 3H), 1.88-2.12 (m, 4H). |

INDEX TABLE H-continued

| Compound | ¹H NMR Data (CDCl₃ solution unless indicated otherwise)[a] |
|---|---|
| 15 | δ 8.63 (d, 1H), 8.12 (d, 1H), 8.10 (s, 2H), 7.99 (s, 1H), 7.23-7.48 (m, 4H), 6.17 (br s, 2H), 4.20 (d, 1H), 4.19 (s, 2H), 3.83 (d, 1H). |
| 16 | (CD₃C(=O)CD₃) δ 8.80 (m, 1H), 8.35 (m, 1H), 8.05-8.10 (m, 2H), 7.45-7.80 (m, 7H), 4.60 (d, 1H), 4.45 (d, 1H), 4.13 (m, 1H), 4.0 (m, 1H), 3.67-3.72 (m, 2H), 1.77 (m, 1H), 1.60 (m, 1H), 1.04 (t, 3H) |
| 17 | δ 8.82 (d, 1H), 8.21 (d, 1H), 7.83 (s, 1H), 7.85 (m, 1H), 7.45-7.75 (m, 7H), 6.55-6.6 (m, 2H), 4.5 (m, 2H), 4.30 (d, 1H), 4.0 (m, 2H), 3.94 (d, 1H). |
| 18 | δ 8.82 (d, 1H), 8.2 (m, 1H), 8.13 (s, 1H), 7.9-7.95 (m, 2H), 7.85 (m, 1H), 7.48 (m, 1H), 7.45-7.65 (m, 5H), 6.70 (br t, 1H), 4.52 (m, 2H), 4.30 (d, 1H), 3.99 (m, 2H), 3.93 (d, 1H). |
| 19 | (CD₃C(=O)CD₃) δ 8.92 (d, 1H), 8.36 (d, 1H), 8.05 (s, 2H), 7.80-7.90 (m, 4H), 7.6-7.7 (m, 3H), 4.65 (d, 1H), 4.48 (d, 1H), 4.40 (m, 1H), 4.13 (m, 1H), 3.86 (m, 1H), 3.57-3.72 (m, 2H), 1.39 (s, 3H), 1.30 (s, 3H). |
| 20 | (CD₃C(=O)CD₃) δ 8.91 (d, 1H), 8.36 (d, 1H), 8.05 (s, 2H), 7.8-7.9 (m, 3H), 7.6-7.74 (m, 4H), 4.65 (d, 1H), 4.47 (d, 1H), 4.1 (m, 1H), 3.83 (m, 1H), 3.70 (m, 1H), 3.49-3.63 (m, 2H), 2.0-2.1 (m, 1H), 1.85-1.95 (m, 2H), 1.74 (m, 1H). |
| 23 | δ 8.81 (d, 1H), 8.33 (d, 1H), 8.02 (s, 1H), 7.87 (s, 1H), 7.85 (s, 1H), 7.61-7.67 (m, 3H), 7.49 (d, 1H), 6.60 (t, 1H), 4.37 (d, 2H), 4.30 (d, 1H), 3.91 (d, 1H). |
| 25 | δ 8.83 (d, 1H), 8.38 (d, 1H), 8.14 (s, 2H), 8.00 (s, 1H), 7.61-7.69 (m, 3H), 7.51 (d, 1H), 6.68 (br t, 1H), 4.48 (d, 2H), 4.38 (d, 1H), 3.96 (d, 1H), 2.07 (s, 3H), 2.06 (s, 3H). |
| 26 | δ 8.78 (d, 1H), 8.29 (d, 1H), 7.86 (s, 1H), 7.80 (s, 1H), 7.72 (s, 1H), 7.60 (m, 2H), 7.56 (d, 1H), 7.43 (d, 1H), 6.70 (br t, 1H), 4.33 (d, 2H), 4.28 (d, 1H), 3.89 (d, 1H). |
| 27 | δ 8.77 (d, 1H), 8.23 (m, 1H), 8.15 (s, 2H), 8.01 (s, 1H), 7.5-7.6 (m, 2H), 7.35-7.45 (m, 2H), 6.63 (br t, 1H), 4.33 (d, 1H), 4.1 (m, 2H), 3.96 (d, 1H), 3.8 (m, 2H), 3.4 (m, 1H), 2.05 (m, 1H), 1.9 (m, 2H), 1.65 (m, 1H). |
| 30 | (CD₃CN) δ 8.79-8.88 (m, 1H), 8.32-8.41 (m, 1H), 7.89 (s, 1H), 7.61-7.77 (m, 6H), 7.43-7.50 (m, 1H), 7.35 (br s, 1H), 4.43 (d, 1H), 4.14-4.22 (m, 3H). |
| 32 | δ 8.78 (d, 1H), 8.28 (d, 1H), 7.86 (s, 1H), 7.80 (s, 1H), 7.72 (s, 1H), 7.42-7.64 (m, 4H), 6.64 (m, 1H), 4.90 (m, 1H), 4.28 (dd, 1H), 3.89 (dd, 1H), 1.62 (d, 3H). |
| 34 | δ 8.79 (d, 1H), 8.32 (d, 1H), 7.53-7.74 (m, 4H), 7.40-7.51 (m, 2H), 7.34 (s, 1H), 6.64 (br s, 1H), 4.36 (d, 2H), 4.26 (d, 1H), 3.88 (d, 1H). |
| 35 | δ 8.78-8.85 (m, 1H), 8.29-8.36 (m, 1H), 7.59-7.71 (m, 4H), 7.50 (dd, 1H), 7.44 (s, 1H), 7.34 (s, 1H), 6.53 (d, 1H), 4.93 (q, 1H), 4.27 (d, 1 H), 3.89 (d, 1H), 1.65 (d, 3H). |
| 36 | δ 9.58 (br s, 1H), 8.64 (d, 1H), 8.13 (d, 1H), 7.39-7.52 (m, 2H), 7.35 (d, 1H), 7.27 (s, 1H), 7.20 (d, 1H), 7.16 (s, 1H), 7.04-7.11 (m, 1H), 7.01 (t, 1H), 4.40 (q, 2H), 4.19 (d, 2H), 4.11 (d, 1H), 3.78 (d, 1H). |
| 37 | δ 8.79 (s, 1H), 8.31 (d, 1H), 7.55-7.71 (m, 3H), 7.47 (d, 1H), 7.32 (s, 1H), 7.20 (s, 1H), 7.04 (t, 1H), 6.56 (br s, 1H), 4.92 (q, 1H), 4.41 (q, 2H), 4.23 (d, 1H), 3.89 (d, 1H), 1.64 (d, 3H). |
| 38 | δ 8.74 (m, 1H), 8.24 (m, 1H), 8.01 (s, 1H), 7.87 (m, 2H), 7.36-7.60 (m, 4H), 6.75 (m, 1H), 4.87 (m, 1H), 4.24 (m, 1H), 3.86 (m, 1H), 1.59 (d, 3H). |
| 40 | (CD₃C(O)CD₃) δ 11.25 (br s, 1H), 8.90 (d, 1H), 8.45 (d, 1H), 8.00 (br d, 1H), 7.92 (s, 1H), 7.85-7.90 (m, 2H), 7.6-7.75 (m, 4H), 4.76 (m, 1H), 4.66 (d, 1H), 4.52 (d, 1H), 1.56 (d, 3H). |
| 42 | (CD₃OD) δ 8.85 (d, 1H), 8.38 (d, 1H), 7.57-7.78 (m, 7H), 4.44 (d, 1H), 4.19 (d, 1H), 4.08 (s, 2H), 3.38 (m, 2H), 3.06 (m, 2H), 2.68 (s, 3H), 1.92 (m, 2H). |
| 43 | δ 8.82 (d, 1H), 8.29 (d, 1H), 7.46-7.67 (m, 7H), 6.90 (s, 1H), 6.47 (br s, 1H), 4.26 (d, 1H), 3.89 (d, 1H), 3.20 (dd, 2H), 1.79 (s, 6H), 1.01 (m, 1H), 0.55 (m, 2H), 0.25 (m, 2H). |
| 44 | * |
| 45 | δ 8.82 (d, 1H), 8.52 (d, 1H), 8.34 (d, 1H), 7.20-7.69 (m, 11H), 6.98 (br s, 1H), 4.61 (d, 1H), 4.32 (d, 2H), 4.26 (d, 1H), 3.89 (d, 1H). |
| 46 | δ 9.35 (br s, 1H), 8.87 (d, 1H), 8.34 (d, 1H), 7.44-7.71 (m, 11H), 7.35 (br s, 1H), 4.56 (d, 2H), 4.25 (d, 1H), 3.89 (d, 1H). |
| 47 | * |
| 48 | δ 8.83 (d, 1H), 8.33 (d, 1H), 7.46-7.68 (m, 7H), 6.96 (br s, 1H), 6.57 (br s, 1H), 4.26 (d, 1H), 4.23 (d, 2H), 3.90 (d, 1H), 3.53 (q, 2H), 2.67 (t, 2H), 2.11 (s, 3H). |
| 49 | δ 8.82 (d, 1H), 8.33 (d, 1H), 7.70 (s, 2H), 7.60-7.68 (m, 3H), 7.48 (d, 1H), 6.97 (br s, 1H), 6.57 (br s, 1H), 4.26 (d, 1H), 4.22 (d, 2H), 3.89 (d, 1H), 3.52 (q, 2H), 2.66 (t, 2H), 2.11 (s, 3H). |
| 50 | (CD₃C(=O)CD₃) δ 8.91 (d, 1H), 8.49 (d, 1H), 7.63-7.88 (m, 8H), 7.41 (br s, 1H), 4.60 (d, 1H), 4.48 (d, 1H), 2.76 (m, 1H), 0.67 (m, 2H), 0.49 (m, 2H). |
| 51 | δ 8.83 (d, 1H), 8.30 (d, 1H), 7.46-7.66 (m, 7H), 7.12 (t, 1H), 6.25 (d, 1H), 4.25 (d, 1H), 4.18 (d, 2H), 3.89 (d, 1H), 3.79 (m, 1H), 1.91 (m, 2H), 1.70 (m, 2H), 1.60 (m, 1H), 1.12-1.38 (m, 5H). |
| 52 | δ 8.83 (d, 1H), 8.29 (d, 1H), 7.45-7.65 (m, 7H), 7.13 (t, 1H), 6.40 (d, 1H), 4.25 (d, 1H), 4.21 (m, 1H), 4.19 (d, 2H), 3.88 (d, 1H), 1.97 (m, 2H), 1.57-1.68 (m, 4H), 1.43 (m, 2H). |
| 53 | δ 8.82 (d, 1H), 8.24 (d, 1H), 7.42-7.66 (m, 7H), 6.99 (br t, 1H), 6.73 (br s, 1H), 4.76 (m, 1H), 4.24 (d, 1H), 3.88 (d, 1H), 2.76 (m, 1H), 1.53 (d, 3H), 0.77 (m, 2H), 0.53 (m, 2H). |
| 54 | (CD₃C(=O)CD₃) δ 8.92 (d, 1H), 8.50 (d, 1H), 8.06 (br s, 2H), 7.62-7.902 (m, 7H), 7.42 (br s, 1H), 4.65 (d, 1H), 4.49 (d, 1H), 4.08 (d, 2H), 2.76 (m, 1H), 0.69 (m, 2H), 0.50 (m, 2H). |
| 55 | (CD₃C(=O)CD₃) δ 8.92 (d, 1H), 8.50 (d, 1H), 8.38 (s, 2H), 8.26 (s, 1H), 7.88 (d, 1H), 7.85 (br s, 1H), 7.75 (d, 1H), 7.64-7.72 (m, 2H), 7.40 (br s, 1H), 4.74 (d, 1H), 4.65 (d, 1H), 4.08 (d, 2H), 2.76 (m, 1H), 0.69 (m, 2H), 0.50 (m, 2H). |
| 56 | d 8.73-8.91 (m, 1H), 8.21-8.36 (m, 1H), 7.82 (s, 1H), 7.53-7.67 (m, 5H), 7.46 (d, 1H), 7.29-7.41 (m, 1H), 7.17 (t, 1H), 6.50 (br s, 1H), 4.24 (d, 1H), 4.20 (d, 2H), 3.90 (d, 1H), 3.15 (dd, 2H), 0.90-1.01 (m, 1H), 0.50 (dt, 2H), 0.20 (dt, 2 H). |
| 57 | δ 8.83 (d, 1H), 8.32 (d, 1H), 7.82 (s, 1H), 7.53-7.68 (m, 5H), 7.48 (d, 1H), 7.30-7.41 (m, 1H), 7.04 (br s, 1H), 6.67 (br s, 1H), 4.25 (d, 1H), 4.21 (d, 2H), 3.92 (d, 1H), 3.51 (dt, 2H), 2.65 (t, 2H), 2.10 (s, 3H). |
| 58 | (CD₃OD) δ 8.79-8.87 (m, 1H), 8.34-8.40 (m, 1H), 7.57-7.77 (m, 7H), 7.38-7.45 (m, 1H), 4.46 (d, 1H), 4.18 (d, 2H), 4.17 (d, 1H). |
| 59 | δ 8.79 (d, 1H), 8.48 (d, 1H) 8.28-8.33 (m, 1H), 7.48-7.68 (m, 8H), 7.44 (d, 1H), 7.29-7.35 (m, 1H), 7.14-7.26 (m, 3H), 4.56 (d, 2H), 4.22-4.31 (m, 3H), 3.90 (d, 1H). |

INDEX TABLE H-continued

| Compound | ¹H NMR Data (CDCl₃ solution unless indicated otherwise)[a] |
|---|---|
| 60 | δ 8.81 (d, 1H), 8.24-8.31 (m, 1H), 7.48-7.64 (m, 6H), 7.44 (d, 1H), 7.28-7.37 (m, 2H), 6.68 (t, 1H), 4.26 (d, 1H), 4.20 (d, 2H), 3.90 (d, 1H), 3.13 (dd, 2H), 0.87-1.00 (m, 1H), 0.48 (dt, 2H), 0.18 (dt, 2H). |
| 61 | δ 8.83 (d, 1H), 8.25-8.42 (m, 1H), 7.47-7.77 (m, 6H), 7.32 (d, 1H), 6.95 (br s, 1H), 6.57 (br s, 1H), 4.28 (d, 1H), 4.22 (d, 2H), 3.92 (d, 1H), 3.46-3.59 (m, 2H), 2.67 (d, 2H), 2.11 (s, 3H). |
| 62 | δ 8.84 (d, 1H), 8.39 and 8.33 (2 d, 1H), 7.68-7.62 (m, 3H), 7.51 (d, 1H), 7.23 (d, 2H), 6.99 and 6.82 (2 br s, 1H), 6.91 (t, 1H), 6.09 and 5.82 (2 br s, 1H), 4.52 and 4.16 (2 d, 2H), 4.27 (d, 1H), 3.89 (d, 1H), 2.77 and 2.68 (2 m, 1H), 0.83 (m, 2H), 0.71 and 0.58 (2 m 2H). |
| 63 | δ 8.85 (d, 1H), 8.38 and 8.33 (2 d, 1H), 7.68-7.61 (m, 3H), 7.54-7.40 (m, 4H), 7.15 (t, 1H), 6.99 and 6.83 (2 t, 1H), 6.13 and 5.82 (2 br s, 1H), 4.52 and 4.16 (2 d, 2H), 4.27 (d, 1H), 3.93 (d, 1H), 2.77 and 2.63 (2 m, 1H), 0.83 (m, 2H), 0.71 and 0.58 (2 m 2H). |
| 64 | δ 8.82 (m, 1H), 8.23 (m, 1H), 8.14 (s, 2H), 8.00 (s, 1H), 7.40-7.66 (m, 4H), 7.08 (t, 1H), 6.81 (br s, 1H), 4.78 (m, 1H), 4.34 (d, 1H), 3.92 (d, 1H), 2.76 (m, 1H), 1.53 (d, 3H), 0.77 (m, 2H), 0.53 (m, 2H). |
| 65 | δ 8.81 (d, 1H), 8.25 (d, 1H), 8.14 (s, 2H), 8.00 (s, 1H), 7.63 (m, 2H), 7.52 (d, 1H), 7.44 (dd, 1H), 6.95 (m, 1H), 6.44 (br s, 1H), 5.65 (br s, 1H), 4.85 (m, 1H), 4.35 (d, 1H), 3.93 (d, 1H), 1.57 (d, 3H). |
| 66 | δ 8.82 (d, 1H), 8.27 (d, 1H), 8.14 (s, 2H), 8.00 (s, 1H), 7.42-7.66 (m, 4H), 7.02 (br s, 1H), 6.55 (br s, 1H), 4.81 (m, 1H), 4.35 (d, 1H), 3.93 (d, 1H), 3.16 (m, 2H), 1.56 (d, 3H), 0.98 (m, 1H), 0.50 (m, 2H), 0.21 (m, 2H). |
| 70 | δ 8.83 (d, 1H), 8.31 (d, 1H), 8.13 (s, 2H), 7.99 (s, 1H), 7.68-7.61 (m, 3H), 7.49 (m, 1H), 6.85 (br s, 1H), 5.99 (br s, 1H), 5.59 (br s, 1H), 4.37 (d, 1H), 4.25 (d, 2H), 3.92 (d, 1H). |
| 71 | δ 8.85 (d, 1H), 8.34 (d, 1H), 8.14 (s, 2H), 8.00 (s, 1H), 7.69-7.61 (m, 3H), 7.52 (d, 1H), 6.93 (br t, 1H), 6.15 (br t, 1H), 4.38 (d, 1H), 4.22 (d, 2H), 3.95 (d, 1H), 3.19 (dd, 1H), 0.99 (m, 1H), 0.55 (m, 2H), 0.23 (m, 2H). |
| 72 | δ 8.82 (d, 1H), 8.24 (d, 1H), 7.87 (s, 1H), 7.82 (s, 1H), 7.72 (s, 1H), 7.62 (m, 2H), 7.50 (d, 1H), 7.43 (d, 1H), 7.00 (br t, 1H), 6.73 (br s, 1H), 4.76 (m, 1H), 4.29 (d, 1H), 3.90 (d, 1H), 2.76 (m, 1H), 0.77 (m, 2H), 0.53 (m, 2H). |
| 73 | δ 8.81 (d, 1H), 8.25 (d, 1H), 7.87 (s, 1H), 7.82 (s, 1H), 7.72 (s, 1H), 7.41-7.65 (m, 4H), 7.08 (br t, 1H), 6.67 (br s, 1H), 4.83 (m, 1H), 4.29 (d, 1H), 3.90 (d, 1H), 3.14 (m, 2H), 1.56 (d, 3H), 0.95 (m, 1H), 0.48 (m, 2H), 0.20 (m, 2H). |
| 74 | δ 8.78 (d, 1H), 8.20 (d, 1H), 7.86 (s, 1H), 7.81 (s, 1H), 7.72 (s, 1H), 7.59 (m, 2H), 7.45 (d, 1H), 7.38 (d, 1H), 7.07 (m, 1H), 6.61 (br s, 1H), 5.80 (s, br. 1H), 4.84 (m, 1H), 4.27 (dd, 1H), 3.88 (dd, 1H), 1.54 (d, 3H). |
| 80 | δ 8.81 (d, 1H), 8.24 (d, 1H), 8.13 (s, 2H), 7.99 (s, 1H), 7.43-7.67 (m, 4H), 6.94 (m, 1H), 6.80 (m, 1H), 4.82 (m, 1H), 4.35 (d, 1H), 3.93 (d, 1H), 3.62 (m, 1H), 3.20 (m, 1H), 1.84 (m, 1H), 1.56 (dd, 3H), 1.43 (m, 1H), 1.13 (m, 1H). |
| 81 | δ 8.77-8.88 (m, 1H), 8.25-8.36 (m, 1H), 7.53-7.70 (m, 4H), 7.47 (d, 1H), 7.45 (br s, 1H), 7.34 (s, 1H), 7.13 (t, 1H), 6.44 (br s, 1H), 4.27 (d, 1H), 4.21 (d, 2H), 3.89 (d, 1H), 3.16 (dd, 2H), 0.89-1.02 (m, 1H), 0.51 (dt, 2H), 0.21 (dt, 2H). |
| 82 | (CD₃OD) δ 8.78-8.87 (m, 1H), 8.31-8.40 (m, 1H), 7.76 (s, 1H), 7.56-7.73 (m, 5H), 7.50 (s, 1H), 4.45 (d, 1H), 4.19 (d, 1H), 4.05 (s, 2H), 2.65-2.75 (m, 1H), 0.70-0.78 (m, 2H), 0.50-0.58 (m, 2H). |
| 83 | δ 8.73 (d, 1H), 8.15 (d, 1H), 8.01 (s, 1H), 7.85 (m, 2H), 7.22-7.57 (m, 5H), 6.80 (br s, 1H), 6.03 (br s, 1H), 4.82 (m, 1H), 4.23 (m, 1H), 3.85 (m, 1H), 1.50 (d, 3H). |
| 84 | δ 8.80 (d, 1H), 8.26 (d, 1H), 7.49-7.66 (m, 3H), 7.40 (d, 1H), 7.36 (t, 1H), 7.31 (s, 1H), 7.16-7.23 (m, 1H), 7.03 (t, 1H), 6.72 (t, 1H), 4.42 (q, 2H), 4.14-4.26 (m, 3H), 3.88 (d, 1H), 3.12 (dd, 2H), 0.86-0.99 (m, 1H), 0.42-0.51 (m, 2H), 0.13-0.21 (m, 2H). |
| 85 | δ 8.77-8.85 (m, 1H), 8.22-8.29 (m, 1H), 7.52-7.67 (m, 3H), 7.43 (d, 1H), 7.22-7.29 (m, 1H), 7.20 (s, 1H), 7.03 (t, 1H), 6.76-6.85 (m, 1H), 4.42 (q, 3H), 4.23 (d, 1H), 4.14 (d, 2H), 3.89 (d, 1H), 2.72 (dt, 1H), 0.71-0.79 (m, 2H) 0.48-0.55 (m, 2H). |
| 86 | δ 8.80 (d, 1H), 8.23 (d, 1H), 7.87 (s, 1H), 7.81 (s, 1H), 7.72 (s, 1H), 7.60 (m, 2H), 7.49 (d, 1H), 7.42 (d, 1H), 6.97 (br d, 1H), 6.49 (br s, 1H), 5.76 (br s, 1H), 4.77 (q, 1H), 4.28 (dd, 1H), 3.90 (d, 1H), 2.05 (m, 1H), 1.84 (m, 1H), 1.06 (t, 3H). |
| 87 | δ 8.79 (d, 1H), 8.23 (d, 1H), 7.87 (s, 1H), 7.81 (s, 1H), 7.72 (s, 1H), 7.60 (m, 2H), 7.50 (d, 1H), 7.41 (dd, 1H), 6.99 (br d, 1H), 6.51 (br s, 1H), 5.86 (br s, 1H), 4.70 (dd, 1H), 4.27 (dd, 1H), 3.88 (d, 1H), 2.23 (m, 1H), 1.10 (d, 3H), 1.06 (d, 3H). |
| 89 | δ 8.86 (m, 1H), 8.38 (m, 1H), 7.24-7.70 (m, 8H), 4.35 (br s, 2H), 4.28 (d, 1H), 3.92 (d, 1H), 3.61 (m, 2H), 3.43 (m, 2H), 1.59-1.72 (m, 6H). |
| 90 | δ 8.85 (d, 1H), 8.36 (d, 1H), 7.46-7.68 (m, 7H), 7.04 (m, 1H), 4.27 (m, 2H), 3.75-3.93 (m, 4H), 2.36-2.57 (m, 2H). |
| 91 | δ 8.84 (d, 1H), 8.36 (d, 1H), 7.46-7.68 (m, 7H), 7.04 (br s, 1H), 4.82 (m, 1H), 4.49 (dd, 1H), 4.27 (d, 2H), 3.90 (d, 1H), 3.65 (m, 2H), 2.05-2.31 (m, 4H). |
| 92 | (CD₃C(O)CD₃) δ 9.00 (m, 1H), 8.03-8.10 (m, 2H), 7.75-8.0 (m, 4H), 7.60-7.73 (m, 2H), 7.54 (d, 1H), 4.65 (d, 1H), 4.48 (d, 1H), 3.9-4.05 (m, 2H), 3.45 (m, 2H), 3.1-3.4 (m, 4H), 2.95-3.1 (m, 2H), 1.28 (m, 3H). |
| 93 | * |
| 94 | * |
| 95 | * |
| 96 | * |
| 97 | δ 8.88 and 8.86 (2 d, 1H), 8.20 (br s, 1H), 7.67 (m, 2H), 7.57-7.45 (m, 5H), 4.82 (dd, 1H), 4.28 and 4.27 (2 d, 1H), 3.91 (d, 1H), 3.87 (s, 3H), 3.30 (m, 1H), 3.17 (m, 1H), 2.37, (m, 1H), 2.11 (m, 1H), 1.97 (m, 1H), 1.88 (m, 1H). |
| 98 | δ 8.88 and 8.86 (2 d, 1H), 8.20 (br s, 1H), 7.67 (m, 2H), 7.57-7.45 (m, 5H), 4.82 (dd, 1H), 4.28 and 4.27 (2 d, 1H), 3.91 (d, 1H), 3.87 (s, 3H), 3.30 (m, 1H), 3.17 (m, 1H), 2.37, (m, 1H), 2.11 (m, 1H), 1.97 (m, 1H), 1.88 (m, 1H). |

INDEX TABLE H-continued

| Compound | $^1$H NMR Data (CDCl$_3$ solution unless indicated otherwise)$^a$ |
|---|---|
| 99 | δ 8.89 (d, 1H), 8.06 (br s, 1H), 7.70-7.62 (m, 2H), 7.58-7.42 (m, 5H), 4.89 (dd, 1H), 4.8 (br s, 1H), 4.27 and 4.26 (2 d, 1H), 3.91 (d, 1H), 3.27 (m, 1H), 3.18 (m, 1H), 2.34, (m, 2H), 1.99 (m, 1H), 1.88 (m, 1H). |
| 100 | δ 8.89 (d, 1H), 8.06 (br s, 1H), 7.70-7.62 (m, 2H), 7.58-7.42 (m, 5H), 4.89 (dd, 1H), 4.3 (br s, 1H), 4.27 and 4.26 (2 d, 1H), 3.91 (d, 1H), 3.27 (m, 1H), 3.18 (m, 1H), 2.34, (m, 2H), 1.99 (m, 1H), 1.88 (m, 1H). |
| 101 | δ 8.89 (d, 1H), 7.86 (d, 1H), 7.80 (t, 1H), 7.71-7.62 (m, 2H), 7.56 (m, 3H), 7.46-7.43 (m, 2H), 4.94 (dd, 1H), 4.28 and 4.27 (2 d, 1H), 4.13 (m, 1H), 3.93 (m, 1H), 3.91 (d, 1H), 3.21 (m, 1H), 3.13 (m, 1H), 2.61, (m, 1H), 2.05 (m, 2H), 1.86 (m, 1H). |
| 102 | δ 8.89 (d, 1H), 7.86 (d, 1H), 7.80 (t, 1H), 7.71-7.62 (m, 2H), 7.56 (m, 3H), 7.46-7.43 (m, 2H), 4.94 (dd, 1H), 4.28 and 4.27 (2 d, 1H), 4.13 (m, 1H), 3.93 (m, 1H), 3.91 (d, 1H), 3.21 (m, 1H), 3.13 (m, 1H), 2.61, (m, 1H), 2.05 (m, 2H), 1.86 (m, 1H). |
| 103 | δ 8.89 (d, 1H), 7.94 (d, 1H), 7.70-7.63 (m, 2H), 7.57-7.54 (m, 3H), 7.48-7.45 (m, 2H), 7.03 (br s, 1H), 4.82 (dd, 1H), 4.29 and 4.28 (2 d, 1H), 3.91 (d, 1H), 3.24 (m, 1H), 3.10 (m, 1H), 2.92 (d, 3H), 2.48, (m, 1H), 2.06 (m, 2H), 1.82 (m, 1H). |
| 104 | δ 8.89 (d, 1H), 7.94 (d, 1H), 7.70-7.63 (m, 2H), 7.57-7.54 (m, 3H), 7.48-7.45 (m, 2H), 7.02 (br s, 1H), 4.82 (dd, 1H), 4.29 and 4.28 (2 d, 1H), 3.91 (d, 1H), 3.24 (m, 1H), 3.10 (m, 1H), 2.92 (d, 3H), 2.48, (m, 1H), 2.06 (m, 2H), 1.82 (m, 1H). |
| 105 | δ 8.89 (d, 1H), 7.94 (d, 1H), 7.70-7.62 (m, 2H), 7.57-7.54 (m, 3H), 7.48-7.45 (m, 2H), 7.01 (br s, 1H), 4.82 (dd, 1H), 4.28 and 4.27 (2 d, 1H), 3.91 (d, 1H), 3.40 (m, 2H), 3.23 (m, 1H), 3.10 (m, 1H), 2.51, (m, 1H), 2.06 (m, 2H), 1.82 (m, 1H), 1.23 (t, 3H). |
| 106 | δ 8.89 (d, 1H), 7.94 (d, 1H), 7.70-7.62 (m, 2H), 7.57-7.54 (m, 3H), 7.48-7.45 (m, 2H), 7.01 (br s, 1H), 4.82 (dd, 1H), 4.28 and 4.27 (2 d, 1H), 3.91 (d, 1H), 3.40 (m, 2H), 3.23 (m, 1H), 3.10 (m, 1H), 2.51, (m, 1H), 2.06 (m, 2H), 1.82 (m, 1H), 1.23 (t, 3H). |
| 107 | δ 8.66 (br t, 1H), 8.62 (d, 1H), 8.18 (d, 1H), 7.87 (d, 1H), 7.70 (dt, 1H), 7.22-7.55 (m, 7H), 4.90 (d, 2H), 4.24 (d, 1H), 3.86 (d, 1H). |
| 108 | δ 8.60 (d, 1H), 7.70-7.85 (m, 5H), 7.57 (d, 2H), 7.50 (d, 1H), 7.43 (t, 1H), 7.36 (d, 1H), 7.25 (dd, 1H), 4.82 (d, 2H), 4.43 (d, 1H), 4.03 (d, 1H). |
| 109 | δ 8.48 (d, 1H), 7.68 (t, 1H), 7.52 (s, 2H), 7.46 (s, 1H), 7.18-7.38 (m, 6H), 7.10 (s, 1H), 4.82 (d, 2H), 4.14 (d, 1H), 3.84 (d, 1H), 3.76 (s, 3H). |
| 110 | δ 11.36 (s, 1H), 8.55 (s, 1H), 8.12 (s, 2H), 8.00 (s, 1H), 7.58 (d, 1H), 7.43 (d, 1H), 6.32 (t, 1H), 4.39 (d, 1H), 3.94 (d, 1H), 3.41 (m, 2H), 1.14 (m, 1H), 0.62 (m, 2H), 0.34 (m, 2H). |
| 111 | δ 7.45-7.54 (m, 4H), 7.14-7.19 (m, 3H), 7.02 (d, 1H), 4.06-4.19 (m, 3H), 3.86-3.91 (m, 1H), 3.82 & 3.77 (s, 3H), 3.27 (m, 1H), 2.98 (m, 1H), 2.71 & 2.69 (s, 3H). |

* See synthesis example for $^1$H NMR data.
$^a$$^1$H NMR data are in ppm downfield from tetramethylsilane. Couplings are designated by (s)—singlet, (d)—doublet, (t)—triplet, (q)—quartet, (dd)—doublet of doublets, (dt)—doublet of triplets, (br)—broad peaks, (m)—multiplet.

BIOLOGICAL EXAMPLES OF THE INVENTION

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-G for compound descriptions.

Test A

For evaluating control of diamondback moth (*Plutella xylostella*) the test unit consisted of a small open container with a 12-14-day-old radish plant inside. This was pre-infested with about 50 neonate larvae that were dispensed into the test unit via corn-cob grits using a bazooka inoculator. The larvae moved onto the test plant after being dispensed into the test unit.

Test compounds were formulated using a solution containing 10% acetone, 90% water and 300 ppm X-77™ Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. All experimental compounds in these tests were sprayed at 50 ppm, and the test was replicated three times. After spraying of the formulated test compound, each test unit was allowed to dry for 1 h and then a black, screened cap was placed on top. The test units were held for 6 days in a growth chamber at 25° C. and 70% relative humidity. Plant feeding damage was then visually assessed based on foliage consumed and a pest mortality rating was also counted and calculated for each test unit.

Of the compounds of Formula 1 tested the following provided very good to excellent levels of control efficacy (20% or less feeding damage or 80% or more mortality): 3, 4, 5, 6, 7, 8, 10, 12, 13, 14, 15, 16, 17, 18, 19, 20, 21, 22, 23, 24, 25, 26, 27, 31, 32, 33, 34, 35, 37, 38, 39, 43, 44, 45, 46, 47, 48, 49, 50, 51, 52, 53, 54, 55, 56, 57, 59, 60, 62, 63, 64, 65, 66, 67, 68, 69, 70, 71, 72, 73, 74, 76, 78, 79, 80, 81, 82, 83, 84, 85, 86, 87, 89, 90, 91, 92, 93, 94, 97, 98, 99, 102, 103, 104, 105, 106 and 111.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet. Test compounds were formulated and sprayed at 50 ppm as described for Test A and replicated three times. After spraying, the test units were maintained in a growth chamber and then the control efficacy was rated for each test unit as described for Test A.

Of the compounds of Formula 1 tested the following provided very good to excellent levels of control efficacy (20% or less feeding damage or 80% or more mortality): 4, 14, 15, 16, 17, 18, 19, 20, 21, 22, 27, 31, 32, 33, 38, 44, 47, 49, 50, 51, 52, 53, 54, 55, 56, 60, 64, 65, 66, 67, 68, 69, 70, 71, 72, 73, 74, 76, 78, 79, 80, 81, 82, 83, 84, 85, 86, 87, 90, 91, 93, 94, 102, 104 and 111.

Test C

For evaluating control of potato leafhopper (*Empoasca fabae*) through contact and/or systemic means, the test unit consisted of a small open container with a 5-6 day old Soleil bean plant (primary leaves emerged) inside. White sand was added to the top of the soil and one of the primary leaves was excised prior to application. Test compounds were formulated and sprayed as described for Test A. All experimental compounds in these tests were sprayed at 250 or 50 ppm as noted, and the test was replicated three times. After spraying, the test units were allowed to dry for 1 hour before they were post-infested with 5 potato leafhoppers (18- to 21-day old adults). A black, screened cap was placed on the top of the cylinder. The test units were held for 6 days in a growth chamber at 19-21° C. and 50-70% relative humidity. The control efficacy of each test unit was then visually assessed by the insect mortality.

Of the compounds of Formula 1 tested at 250 ppm, the following provided very good to excellent levels of control efficacy (80% or more mortality): 3, 4, 5, 6, 14, 19, 21, 22, 27, 31, 32, 43, 44, 45, 47, 48, 49, 50, 53, 54, 55, 60, 64, 65, 66, 67, 68, 69, 70, 71, 72, 73, 74, 76, 78, 79, 80, 90, 91, 93, 94, 103, 104 and 106.

Of the compounds of Formula 1 tested at 50 ppm, the following provided very good to excellent levels of control efficacy (80% or more mortality): 4, 5, 6, 14, 22, 27, 31, 32, 39, 43, 44, 45, 48, 49, 50, 53, 54, 55, 64, 65, 66, 67, 68, 69, 70, 71, 72, 73, 74, 76, 78, 79, 80, 81, 82, 83, 86, 87, 90, 91, 93, 94, 103, 104 and 106.

Test D

For evaluating control of corn planthopper (Peregrinus maidis) through contact and/or systemic means, the test unit consisted of a small open container with a 3-4-day-old maize plant (spike) inside. White sand was added to the top of the soil prior to application. Test compounds were formulated and sprayed at 250 ppm and replicated three times as described for Test A. After spraying, the test units were allowed to dry for 1 h before they were post-infested with 10-20 corn planthoppers (18- to 20-day-old nymphs) by sprinkling them onto the sand with a salt shaker. A black, screened cap was placed on the top of the cylinder. The test units were held for 6 days in a growth chamber at 19-21° C. and 50-70% relative humidity. Each test unit was then visually assessed for insect mortality.

Of the compounds tested, the following resulted in at least 80% mortality: 27, 53, 72, 74, 78, 83, 86 and 91.

Test E

For evaluating control of the western flower thrips (*Frankliniella occidentalis*) through contact and/or systemic means, the test unit consisted of a small open container with a 5-7 day old Soleil Bean plant inside. Test compounds were formulated and sprayed as described for Test A. All experimental compounds in these tests were sprayed at 250 or 50 ppm as noted, and the test was replicated three times. After spraying, the test units were allowed to dry for 1 hour and then 22-27 adult thrips were added to each unit and then a black, screened cap was placed on top. The test units were held for 6 days at 25° C. and 45-55% relative humidity. A mortality rating was assessed along with a plant damage rating for each test unit.

Of the compounds of Formula 1 tested at 250 ppm, the following provided very good to excellent levels of control efficacy (20% or less feeding damage or 80% or more mortality): 3, 4, 6, 8, 22, 26, 31, 33, 43, 44, 45, 47, 48, 49, 50, 53, 55, 64, 66, 67, 68, 72, 73, 74, 76, 78, 79, 80, 89, 90, 93, 94, 98, 104 and 106.

Of the compounds of Formula 1 tested at 50 ppm, the following provided very good to excellent levels of control efficacy (20% or less feeding damage or 80% or more mortality): 3, 4, 6, 22, 43, 44, 47, 50, 53, 55, 64, 65, 66, 67, 68, 69, 70, 71, 72, 73, 74, 76, 78, 79, 80, 81, 82, 83, 84, 85, 86, 87, 90, 93, 94, 104 and 106.

Test F

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated and sprayed as described for Test A. All experimental compounds in these tests were sprayed at 250 ppm, and the test was replicated three times. After spraying of the formulated test compound, each test unit was allowed to dry for 1 h and then a black, screened cap was placed on top. The test units were held for 6 days in a growth chamber at 19-21° C. and 50-70% relative humidity. Each test unit was then visually assessed for insect mortality.

Of the compounds of Formula 1 tested, the following resulted in at least 80% mortality: 4, 27, 38, 43, 44, 47, 50, 51, 53, 55, 65, 66, 67, 69, 71, 72, 73, 74, 76, 78, 79, 80, 81, 82, 83, 86, 87, 90 and 93.

Test G

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test F, and the soil of the test unit was covered with a layer of sand.

Test compounds were formulated and sprayed at 250 ppm and the test was replicated three times. After spraying, the test units were maintained in a growth chamber and then visually rated assessed for insect mortality.

Of the compounds tested, the following resulted in at least 80% mortality: 27, 53, 65, 71, 72, 74, 78, 82 and 83.

Test H

For evaluating control of silverleaf whitefly (*Bemisia tabaci*), the test unit consisted of a 14-21-day-old cotton plant grown in Redi-earth® media (Scotts Co.) with at least two true leaves infested with 2nd and 3rd instar nymphs on the underside of the leaves.

Test compounds were formulated in no more than 2 mL of acetone and then diluted with water to 25-30 mL. The formulated compounds were applied using a flat fan air-assisted nozzle (Spraying Systems 122440) at 10 psi (69 kPa). Plants were sprayed to run-off on a turntable sprayer (patent publication EP-1110617-A1). All experimental compounds in this screen were sprayed at 250 ppm and replicated three times. After spraying of the test compound, the test units were held for 6 days in a growth chamber at 50-60% relative humidity and 28° C. daytime and 24° C. nighttime temperature. Then the leaves were removed and then dead and live nymphs were counted to calculate percent mortality.

Of the compounds of Formula 1 tested, the following resulted in at least 80% mortality: 5, 27, 39, 73, 76, 86 and 91.

Test I

For evaluating control of the cat flea (*Ctenocephalides felis*), a CD-1® mouse (about 30 g, male, obtained from Charles River Laboratories, Wilmington, Mass.) was orally dosed with a test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

Of the compounds of Formula 1 tested, the following compounds caused 50% or more mortality: 4, 21, 22, 43, 44, 47, 50, 54, 55, 64, 65, 66, 67, 68, 69, 70, 71, 72, 73, 74, 75, 76, 77, 78, 79, 80, 81, 82, 83, 93 and 107.

TEST J

For evaluating control of the cat flea (*Ctenocephalides felis* Bouche), a test compound was solubilized in acetone/water (75:25) to provide a final test concentration of 500 ppm. Then 20 µL of the 500 ppm solution was applied to filter paper in the bottom of a tube. The tube is allowed to dry for 3 hours. Then approximately 10 adult fleas were added to the tube and the tube was capped. The fleas were evaluated for mortality 48 hours later.

Of the compounds of Formula 1 tested, the following compounds caused 50% or more mortality: 1, 3, 4, 43, 44, 47, 49, 50, 52, 65, 89 and 90.

Test K

For evaluating control of the relapsing fever tick (*Ornithodoros turicata*), a test compound was solubilized in propylene glycol/glycerol formal (60:40) and then diluted in bovine blood to provide a final test concentration of 30 ppm. The treated blood was placed in a tube, and the top of the tube was covered with a membrane. Approximately 5 *O. turicata* nymphs were placed on the membrane and allowed to feed on the treated blood until fully engorged. The ticks were then evaluated for mortality 48 hours later.

Of the compounds of Formula 1 tested, the following compounds caused 50% or more mortality: 43, 44, 45, 47 and 48.

What is claimed is:

1. A compound selected from Formula 1, N-oxides and salts thereof,

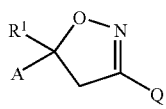

wherein

A is a 6-membered aromatic ring containing carbon atoms and 0-3 nitrogen atoms as ring members, said ring optionally substituted with 1-5 substituents independently selected from $R^2$;

Q is 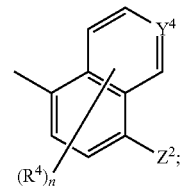

$Y^4$ is $CR^4$ or N;

$Z^2$ is 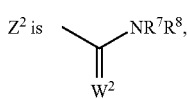

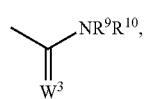

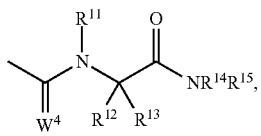

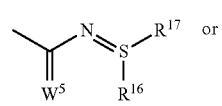

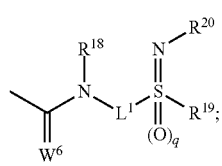

each $W^2$, $W^3$, $W^4$, $W^5$ and $W^6$ is independently O or S;

$L^1$ is $C_2$-$C_6$ alkylene optionally substituted with one or more substituents independently selected from $R^{22}$;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^{21}$;

each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

each $R^3$ and $R^4$ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

$R^7$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^8$ is $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{18}$ alkylcycloalkyl or $C_4$-$C_{18}$ cycloalkylalkyl, each substituted with one or more substituents independently selected from $R^{34}$ and optionally substituted with one or more substituents independently selected from $R^{35}$; or R$^7$ and R$^8$ are taken together with the nitrogen atom to which they are attached to form a ring containing as ring members in addition to the attaching nitrogen atom from 2 to 6 carbon atoms and optionally one additional ring member selected from the group consisting of O, N and S(=O)$_u$, said ring optionally substituted with 1 to 4 substituents independently selected from the group consisting of halogen, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C(=O)R$^{23}$, CO$_2$R$^{24}$ and C(=O)NR$^{25}$R$^{26}$;

each R$^9$ and R$^{18}$ is independently H; or C$_1$-C$_{12}$ alkyl, C$_2$-C$_{12}$ alkenyl, C$_2$-C$_{12}$ alkynyl, C$_3$-C$_{12}$ cycloalkyl, C$_4$-C$_{12}$ alkylcycloalkyl or C$_4$-C$_{12}$ cycloalkylalkyl, each optionally substituted with one or more substituents independently selected from R$^{35}$;

R$^{10}$ is C$_1$-C$_{12}$ alkyl substituted with one or more R$^{35}$; or CN, SCN, S(=O)$_u$R$^{37}$, SO$_2$NR$^{37}$R$^{38}$, N=CR$^{38}$R$^{39}$, N=CR$^{38}$OR$^{39}$, NR$^{37}$C(=O)OR$^{38}$, NR$^{37}$C(=O)R$^{38}$, SiR$^{41}$R$^{42}$R$^{43}$, CO$_2$R$^{36}$, C(=O)R$^{36}$, C(=O)NR$^{37}$R$^{38}$, C(=S)SR$^{39}$, C(=S)OR$^{39}$, C(=S)R$^{38}$, C(=S)NR$^{37}$R$^{38}$, P(=O)(OR$^{39}$)$_2$ or P(=S)(OR$^{39}$)$_2$; provided that when R$^9$ is H or an unsubstituted group of C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, then R$^{10}$ is CN, SCN, S(=O)$_u$R$^{37}$, SO$_2$NR$^{37}$R$^{38}$, N=CR$^{38}$R$^{39}$, N=CR$^{38}$OR$^{39}$, SiR$^{41}$R$^{42}$R$^{43}$, CO$_2$R$^{36}$, C(=O)R$^{36}$, C(=O)NR$^{37}$R$^{38}$, C(=S)SR$^{39}$, C(=S)OR$^{39}$, C(=S)R$^{38}$, C(=S)NR$^{37}$R$^{38}$, P(=O)(OR$^{39}$)$_2$ or P(=S)(OR$^{39}$)$_2$;

R$^{11}$ is H; or C$_1$-C$_{12}$ alkyl, C$_2$-C$_{12}$ alkenyl, C$_2$-C$_{12}$ alkynyl, C$_3$-C$_{12}$ cycloalkyl, C$_4$-C$_{12}$ alkylcycloalkyl or C$_4$-C$_{12}$ cycloalkylalkyl, each optionally substituted with one or more substituents independently selected from R$^{35}$; or CN, C(=O)R$^{23}$, CO$_2$R$^{24}$, C(=O)NR$^{25}$R$^{26}$, OR$^{27}$, SR$^{28}$, S(=O)R$^{29}$, SO$_2$R$^{30}$, NR$^{31}$R$^{32}$, C(=S)SR$^{37}$, C(=S)OR$^{37}$, C(=S)R$^{37}$, C(=S)NR$^{37}$R$^{38}$, SO$_2$NR$^{37}$R$^{38}$, NR$^{37}$C(=O)R$^{38}$, NR$^{37}$SO$_2$R$^{29}$ or Q$^1$;

R$^{12}$ is H; or C$_1$-C$_{12}$ alkyl, C$_3$-C$_7$ cycloalkyl, C$_4$-C$_{12}$ alkylcycloalkyl, C$_4$-C$_{12}$ cycloalkylalkyl, each optionally substituted with one or more substituents independently selected from R$^{35}$; or Q$^1$;

R$^{13}$ is H; or C$_1$-C$_{12}$ alkyl, C$_3$-C$_7$ cycloalkyl, C$_4$-C$_{12}$ alkylcycloalkyl or C$_4$-C$_{12}$ cycloalkylalkyl, each optionally substituted with one or more substituents independently selected from R$^{35}$; or CN, C(=O)R$^{36}$, C(=O)OR$^{37}$, C(=S)SR$^{37}$, C(=S)OR$^{37}$, C(=S)R$^{37}$, C(=S)NR$^{37}$R$^{38}$ or Q$^1$; or R$^{12}$ and R$^{13}$ are taken together with the carbon atom to which they are attached to form a carbocyclic ring containing as ring members from 3 to 6 carbon atoms, said ring optionally substituted with one or more substituents independently selected from R$^{35}$;

R$^{14}$ and R$^{15}$ are independently H; or C$_1$-C$_{12}$ alkyl, C$_2$-C$_{12}$ alkenyl, C$_2$-C$_{12}$ alkynyl, C$_3$-C$_{12}$ cycloalkyl, C$_4$-C$_{12}$ alkylcycloalkyl or C$_4$-C$_{12}$ cycloalkylalkyl, each optionally substituted with one or more substituents independently selected from R$^{35}$; or CN, C(=O)R$^{23}$, CO$_2$R$^{24}$, C(=O)NR$^{25}$R$^{26}$, OR$^{27}$, SR$^{28}$, S(=O)R$^{29}$, SO$_2$R$^{30}$, NR$^{31}$R$^{32}$, C(=S)SR$^{37}$, C(=S)OR$^{37}$, C(=S)R$^{37}$, C(=S)NR$^{37}$R$^{38}$, SO$_2$NR$^{37}$R$^{38}$, NR$^{37}$C(=O)R$^{38}$, NR$^{37}$SO$_2$R$^{29}$ or Q$^1$; or R$^{14}$ and R$^{15}$ are taken together with the nitrogen atom to which they are attached to form a ring containing as ring members in addition to the attaching nitrogen atom from 2 to 6 carbon atoms and optionally one additional ring member selected from the group consisting of O, N and S(=O)$_u$, said ring optionally substituted with 1 to 4 substituents independently selected from the group consisting of halogen, C$_1$-C$_6$ alkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C(=O)R$^{23}$, CO$_2$R$^{24}$, C(=O)NR$^{25}$R$^{26}$, CN and NO$_2$; provided that R$^{14}$ and R$^{15}$ are other than C$_1$-C$_6$ alkyl or C$_1$-C$_6$ haloalkyl when R$^{11}$ is H, C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl;

each R$^{16}$ and R$^{17}$ is independently C$_1$-C$_6$ alkyl optionally substituted with one or more substituents independently selected from R$^{35}$; or R$^{16}$ and R$^{17}$ are taken together with the sulfur atom to which they are attached to form a ring containing as ring members in addition to the attaching sulfur atom from 3 to 6 carbon atoms, said ring optionally substituted with one or more substituents independently selected from R$^{35}$;

R$^{19}$ is C$_1$-C$_6$ alkyl optionally substituted with one or more substituents independently selected from R$^{35}$;

R$^{20}$ is H; or C$_1$-C$_6$ alkyl optionally substituted with one or more substituents independently selected from R$^{35}$; or CN, C(=O)R$^{24}$, CO$_2$R$^{24}$ or NO$_2$;

R$^{21}$ is independently H, halogen, C$_1$-C$_6$ alkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, CN or NO$_2$;

each R$^{35}$ is independently H, halogen, C$_1$-C$_6$ alkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, CN, NO$_2$, SCN, C(=O)R$^{37}$, CO$_2$R$^{37}$, C(=S)SR$^{37}$, C(=S)OR$^{37}$, C(=S)R$^{37}$, C(=O)NR$^{37}$R$^{38}$, C(=S)NR$^{37}$R$^{38}$, SO$_2$NR$^{37}$R$^{38}$, NR$^{37}$R$^{38}$, SiR$^{41}$R$^{42}$R$^{43}$ or Q$^1$;

each R$^{23}$, R$^{25}$, R$^{26}$, R$^{27}$, R$^{28}$, R$^{31}$ and R$^{32}$ is independently H; or C$_1$-C$_{18}$ alkyl, C$_2$-C$_8$ alkenyl, C$_2$-C$_8$ alkynyl, C$_3$-C$_9$ cycloalkyl, C$_4$-C$_{10}$ alkylcycloalkyl or C$_4$-C$_{10}$ cycloalkylalkyl, each optionally substituted with one or more substituents independently selected from R$^{35}$; or Q$^1$;

each R$^{24}$, R$^{29}$ and R$^{30}$ is independently H; or C$_1$-C$_{18}$ alkyl, C$_2$-C$_8$ alkenyl, C$_2$-C$_8$ alkynyl, C$_3$-C$_9$ cycloalkyl, C$_4$-C$_{10}$ alkylcycloalkyl or C$_4$-C$_{10}$ cycloalkylalkyl, each optionally substituted with one or more substituents independently selected from R$^{35}$; or Q$^1$;

R$^{34}$ is OR$^{36}$, OC(=O)R$^{37}$, OC(=O)NR$^{37}$R$^{38}$, OCO$_2$R$^{37}$, OSO$_2$R$^{39}$, SH, SR$^{36}$, S(=O)R$^{36}$, SO$_2$R$^{36}$, SO$_2$NR$^{37}$R$^{38}$, NR$^{36}$R$^{37}$, N=CR$^{37}$R$^{40}$, N=CR$^{40}$OR$^{37}$, NR$^{37}$C(=O)R$^{38}$, SCN, SiR$^{41}$R$^{42}$R$^{43}$, CO$_2$H, CO$_2$R$^{46}$, C(=O)R$^{46}$, C(=S)SR$^{40}$, C(=S)OR$^{40}$, C(=O)SR$^{40}$, C(=S)R$^{37}$, C(=S)NR$^{37}$R$^{38}$, P(=O)(OR$^{37}$)$_2$ or P(=S)(OR$^{37}$)$_2$;

R$^{36}$ is Q$^1$; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl, each substituted with one or more substituents independently selected from halogen, CN, NO$_2$, OR$^{44}$, SR$^{44}$, S(=O)R$^{44}$, SO$_2$R$^{44}$, CO$_2$R$^{44}$ and C(=O)NR$^{44}$R$^{45}$;

each R$^{37}$ and R$^{38}$ is independently H; or Q$^1$; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl, each optionally substituted with one of more substituents independently selected from the group consisting of halogen, CN, $NO_2$, $OR^{44}$, $SR^{44}$, $S(=O)R^{44}$, $SO_2R^{44}$, $CO_2R^{44}$, $C(=O)NR^{44}R^{45}$ and $Q^1$;

$R^{39}$ is $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each optionally substituted with one or more substituents independently selected from the group consisting of halogen, CN, $NO_2$, $OR^{44}$, $SR^{44}$, $S(=O)R^{44}$, $SO_2R^{44}$, $CO_2R^{44}$, $C(=O)NR^{44}R^{45}$ and $Q^1$;

$R^{40}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl, $C_2$-$C_7$ alkoxycarbonyl or a phenyl ring, each optionally substituted with one of more substituents independently selected from the group consisting of halogen, $C_1$-$C_6$ alkoxy, $C_1$-$C_6$ haloalkoxy, CN and $NO_2$;

each $R^{41}$, $R^{42}$ and $R^{43}$ is independently $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or a phenyl ring, each optionally substituted with one of more substituents selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN and $NO_2$;

each $R^{44}$ and $R^{45}$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more substituents selected from $R^{35}$; or $Q^1$;

$R^{46}$ is $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each substituted with one or more substituents selected from CN, $NO_2$, $OR^{44}$, $SR^{44}$, $S(=O)R^{44}$, $SO_2R^{44}$, $CO_2R^{44}$ and $C(=O)NR^{44}R^{45}$;

each $Q^1$ is a 3- to 10-membered ring or 7- to 10-membered bicyclic ring system containing as ring members from 2 to 10 carbon atoms and from 0 to 5 heteroatoms selected from the group consisting of carbon, sulfur and nitrogen atoms, of which up to two of the carbon or sulfur atoms are present as $C(=O)$, $S(=O)$ or $SO_2$, said ring or ring system optionally substituted with one or more substituents independently selected from $R^2$;

n is an integer from 0 to 4;

q is 0 or 1; and u is 0, 1 or 2.

2. A compound of claim 1 wherein $R^7$ and $R^8$ are taken together with the nitrogen atom to which they are attached to form a ring containing as ring members in addition to the attaching nitrogen atom from 2 to 6 carbon atoms and optionally one additional ring member selected from the group consisting of O, N and $S(=O)_u$, said ring substituted with 1 substituent selected from the group consisting of $CO_2R^{24}$ and $C(=O)NR^{25}R^{26}$.

3. A composition for controlling an invertebrate pest comprising a compound of claim 1 and at least one additional component selected from the group consisting of surfactants, solid diluents and liquid diluents, said composition optionally further comprising at least one biologically active compound or agent in addition to said compound of claim 1.

4. The composition of claim 3 wherein the at least one biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

5. The composition of claim 4 wherein the at least one biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

6. A composition for controlling an invertebrate pest comprising a compound of claim 2 and at least one additional component selected from the group consisting of surfactants, solid diluents and liquid diluents, said composition optionally further comprising at least one biologically active compound or agent in addition to said compound of claim 2.

7. The composition of claim 6 wherein the at least one biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

8. The composition of claim 7 wherein the at least one biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino) carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

9. A compound selected from Formula 1, N-oxides and salts thereof, wherein:

Q is $Z^2$ is $W^4$ is O or S;

A is a phenyl ring substituted with 1 to 3 substituents independently selected from the group consisting of halogen, $C_1$-$C_3$ alkyl, $C_1$-$C_3$ haloalkyl, $C_1$-$C_3$ haloalkoxy and CN;

$R^1$ is $C_1$-$C_3$ haloalkyl;

each $R^2$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

each $R^4$ is independently H, halogen, $C_1$-$C_6$ alkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

$R^{11}$ is H;

$R^{12}$ is H or $C_1$-$C_3$ alkyl;

$R^{13}$ is H or $C_1$-$C_3$ alkyl;

$R^{14}$ is $C_1$-$C_6$ alkyl, $C_3$-$C_6$ cycloalkyl or $C_4$-$C_7$ alkylcycloalkyl optionally substituted with one or more substituents independently selected from $R^{35}$;

$R^{15}$ is H; or $C_1$-$C_{12}$ alkyl, $C_2$-$C_{12}$ alkenyl, $C_2$-$C_{12}$ alkynyl, $C_3$-$C_{12}$ cycloalkyl, $C_4$-$C_{12}$ alkylcycloalkyl or $C_4$-$C_{12}$ cycloalkylalkyl, each optionally substituted with one or more substituents independently selected from $R^{35}$; or CN, $C(=O)R^{23}$, $CO_2R^{24}$, $C(=O)NR^{25}R^{26}$, $OR^{27}$, $SR^{28}$, $S(=O)R^{29}$, $SO_2R^{30}$, $NR^{31}R^{32}$, $C(=S)SR37$, $C(=S)OR^{37}$, $C(=S)R^{37}$, $C(=S)NR^{37}R^{38}$, $SO_2NR^{37}R^{38}$, $NR^{37}C(=O)R^{38}$, $NR^{37}SO_2R^{29}$ or $Q^1$;

$R^{35}$ is H, halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, CN or $NO_2$;

$Y^4$ is CH;

each $R^{23}$, $R^{25}$, $R^{26}$, $R^{27}$, $R^{28}$, $R^{31}$ and $R^{32}$ is independently H; or $C_1$-$C_{18}$ alkyl, $C_2$-$C_8$ alkenyl, $C_2$-$C_8$ alkynyl, $C_3$-$C_9$ cycloalkyl, $C_4$-$C_{10}$ alkylcycloalkyl or $C_4$-$C_{10}$ cycloalkylalkyl, each optionally substituted with one or more substituents independently selected from $R^{35}$; or $Q^1$;

each $R^{24}$, $R^{29}$ and $R^{30}$ is independently H; or $C_1$-$C_{18}$ alkyl, $C_2$-$C_8$ alkenyl, $C_2$-$C_8$ alkynyl, $C_3$-$C_9$ cycloalkyl, $C_4$-$C_{10}$ alkylcycloalkyl or $C_4$-$C_{10}$ cycloalkylalkyl, each optionally substituted with one or more substituents independently selected from $R^{35}$; or $Q^1$;

each $R^{37}$ and $R^{38}$ is independently H; or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl, each optionally substituted with one of more substituents independently selected from the group consisting of halogen, CN, $NO_2$, $OR^{44}$, $SR^{44}$, $S(=O)R^{44}$, $SO_2R^{44}$, $CO_2R^{44}$, $C(=O)NR^{44}R^{45}$ and $Q^1$;

each $R^{41}$, $R^{42}$ and $R^{43}$ is independently $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl or a phenyl ring, each optionally substituted with one of more substituents selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, CN and $NO_2$;

each $R^{44}$ and $R^{45}$ is independently H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more substituents selected from $R^{35}$; or $Q^1$;

each $Q^1$ is a 3- to 10-membered ring or 7- to 10-membered bicyclic ring system containing as ring members from 2 to 10 carbon atoms and from 0 to 5 heteroatoms selected from the group consisting of carbon, sulfur and nitrogen atoms, of which up to two of the carbon or sulfur atoms are present as $C(=O)$, $S(=O)$ or $SO_2$, said ring or ring system optionally substituted with one or more substituents independently selected from $R^2$; and n is an integer from 0 to 4.

10. A compound of claim 9 wherein:

A is a phenyl ring substituted with 2 substituents independently selected from the group consisting of halogen, $C_1$-$C_2$ haloalkyl and $C_1$-$C_2$ haloalkoxy;

$R^1$ is $CF_3$;

$R^{12}$ is H;

$R^{13}$ is H or $CH_3$;

$R^{14}$ is cyclopropyl or methylcyclopropyl optionally substituted with one or more substituents independently selected from $R^{35}$;

$R^{15}$ is H;

$R^{35}$ is H or halogen.

11. A composition for controlling an invertebrate pest comprising a compound of claim 9 and at least one additional component selected from the group consisting of surfactants, solid diluents and liquid diluents, said composition optionally further comprising at least one biologically active compound or agent in addition to said compound of claim 9.

12. The composition of claim 11 wherein the at least one biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

13. The composition of claim 12 wherein the at least one biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

14. A composition for controlling an invertebrate pest comprising a compound of claim 10 and at least one additional component selected from the group consisting of surfactants, solid diluents and liquid diluents, said composition optionally further comprising at least one biologically active compound or agent in addition said compound of claim 10.

15. The composition of claim 14 wherein the at least one biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

16. The composition of claim 15 wherein the at least one biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

17. N-[2-[(cyclopropylmethyl)amino]-2-oxoethyl]-4-[5-(3,5-dichlorophenyl)-4,5-dihydro-5-(trifluoromethyl)-3-isoxazolyl]-1-Naphthalenecarboxamide.

18. A composition for controlling an invertebrate pest comprising a compound of claim 17 and at least one additional component selected from the group consisting of surfactants, solid diluents and liquid diluents, said composition optionally further comprising at least one biologically active compound or agent in addition to said compound of claim 17.

19. The composition of claim 18 wherein the at least one biologically active compound or agent is selected from the group consisting of abamectin, acephate, acequinocyl, acetamiprid, acrinathrin, amidoflumet, amitraz, avermectin, azadirachtin, azinphos-methyl, bifenthrin, bifenazate, bistrifluron, borate, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, carbofuran, cartap, chlorantraniliprole, chlorfenapyr, chlorfluazuron, chlorpyrifos, chlorpyrifos-methyl, chromafenozide, clofentezin, clothianidin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

20. The composition of claim 19 wherein the at least one biologically active compound or agent is selected from the group consisting of abamectin, acetamiprid, acrinathrin, amitraz, avermectin, azadirachtin, bifenthrin, 3-bromo-1-(3-chloro-2-pyridinyl)-N-[4-cyano-2-methyl-6-[(methylamino)carbonyl]phenyl]-1H-pyrazole-5-carboxamide, buprofezin, cadusafos, carbaryl, cartap, chlorantraniliprole, chlorfenapyr, chlorpyrifos, clothianidin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

21. A method for controlling an invertebrate pest comprising contacting the invertebrate pest or its environment with a biologically effective amount of a compound of claim 1.

22. A method for controlling an invertebrate pest comprising contacting the invertebrate pest or its environment with a biologically effective amount of a compound of claim 2.

23. A method for controlling an invertebrate pest comprising contacting the invertebrate pest or its environment with a biologically effective amount of a compound of claim 9.

24. A method for controlling an invertebrate pest comprising contacting the invertebrate pest or its environment with a biologically effective amount of a compound of claim 10.

25. A method for controlling an invertebrate pest comprising contacting the invertebrate pest or its environment with a biologically effective amount of a compound of claim 17.

* * * * *